(12) United States Patent
Ott et al.

(10) Patent No.: US 6,720,329 B2
(45) Date of Patent: Apr. 13, 2004

(54) SPIRO-CYCLIC β-AMINO ACID DERIVATIVES AS INHIBITORS OF MATRIX METALLOPROTEASES AND TNF-α CONVERTING ENZYME (TACE)

(75) Inventors: Gregory R. Ott, Media, PA (US); Xiao Tao Chen, Newark, DE (US); Jingwu Duan, Newark, DE (US); Matthew E. Voss, Lincoln University, PA (US)

(73) Assignee: Bristol-Myers Squibb Pharma, Princeton, NJ (US)

( * ) Notice: Subject to any disclaimer, the term of this patent is extended or adjusted under 35 U.S.C. 154(b) by 0 days.

(21) Appl. No.: 10/096,804

(22) Filed: Mar. 12, 2002

(65) Prior Publication Data

US 2003/0087882 A1 May 8, 2003

Related U.S. Application Data

(60) Provisional application No. 60/275,898, filed on Mar. 15, 2001.

(51) Int. Cl.⁷ .................. A61K 31/443; A61K 31/4439; A61K 31/4409; A61K 31/4747; C07D 221/20
(52) U.S. Cl. .................. 514/278; 514/342; 514/339; 514/336; 546/15; 546/152; 546/268.1; 546/276.4; 546/279.7; 546/281.7
(58) Field of Search ................ 546/169, 278.4, 546/279.1, 279.7, 281.7, 283.4, 284.1, 15; 514/278, 279, 314, 336, 338, 339, 342

(56) References Cited

U.S. PATENT DOCUMENTS 4,261,990 A  4/1981  Bowman 6,489,316 B2  12/2002  Sandanayaka et al.

FOREIGN PATENT DOCUMENTS

| EP | 780386 A | 6/1997 |
| EP | 818442 A | 1/1998 |
| WO | WO 9720824 A | 6/1997 |
| WO | WO01/70673 | * 9/2001 |

* cited by examiner

Primary Examiner—Rita Desai
(74) Attorney, Agent, or Firm—David H. Vance; Jing S. Belfield

(57) ABSTRACT

The present application describes novel spiro-cyclic β-amino acid derivatives of formula I:

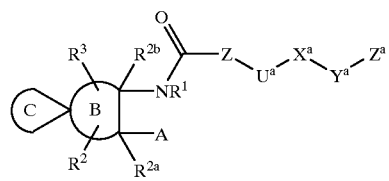

or pharmaceutically acceptable salt forms thereof, wherein ring B is a 3–13 membered carbocycle or heterocycle, ring C forms a 3–11 membered spiro-carbocycle or spiro-heterocycleon ring B, and the other variables are defined in the present specification, which are useful as as matrix metalloproteinases (MMP), TNF-α converting enzyme (TACE), and/or aggrecanase inhibitors.

28 Claims, No Drawings

SPIRO-CYCLIC β-AMINO ACID DERIVATIVES AS INHIBITORS OF MATRIX METALLOPROTEASES AND TNF-α CONVERTING ENZYME (TACE)

CROSS-REFERENCE TO RELATED APPLICATIONS

This application claims the benefit of U.S. Provisional App. Ser. No. 60/275,898, filed Mar. 15, 2001.

FIELD OF THE INVENTION

This invention relates generally to novel spiro-cyclic β-amino acid derivatives as matrix metalloproteinases (MMP), TNF-α converting enzyme (TACE), and/or aggrecanase inhibitors, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA. Increased activities of collagenases and stromelysin have been found in OA cartilage and the activity correlates with severity of the lesion (Mankin et al. *Arthritis Rheum.* 1978, 21, 761–766, Woessner et al. *Arthritis Rheum.* 1983, 26, 63–68 and Woessner et al. *Arthritis Rheum.* 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al. *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

EP 0,780,286 describes MMP inhibitors of formula A:

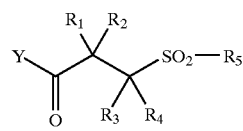

wherein Y can be NHOH, $R^1$ and $R^2$ can combine to form a cycloalkyl or heterocyclo alkyl group, $R^3$ and $R^4$ can be a variety of groups including H, and $R^5$ can be substituted aryl.

WO 97/20824 depicts MMP inhibitors of formula B:

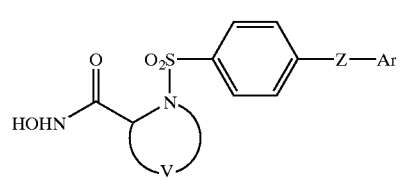

wherein ring V contains six atoms, Z is O or S, and Ar is an aryl or heteroaryl group. Ar is preferably a monocyclic aryl group with an optional para substituent or an unsubstituted monocyclic heteroaryl group.

EP 0,818,442 illustrates MMP inhibitors of formula C:

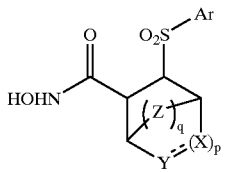

wherein Ar is optionally substituted phenyl or naphthyl, Z can be absent and X and Y can be a variety of substituents. Compounds of this sort are not considered to be part of the present invention.

The compounds of the present invention act as inhibitors of MPs, in particular TACE, MMPs, and/or aggrecanase. These novel molecules are provided as anti-inflammatory compounds and cartilage protecting therapeutics. The inhibition of aggrecanase, TACE, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, one object of the present invention is to provide novel spiro-cyclic hydroxamic acids useful as MMP, TACE, and/or aggrecanase inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders, comprising: administering to a host, in need of such treatment, a therapeutically effective amount of at least one of the compounds of the present invention or a pharmaceutically acceptable salt or prodrug form thereof.

It is another object of the present invention to provide a method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt or prodrug form thereof.

It is another object of the present invention to provide a method comprising: administering a compound of the present invention or a pharmaceutically acceptable salt or prodrug form thereof in an amount effective to treat a condition or disease mediated by MMPs, TACE, aggrecanase, or a combination thereof.

It is another object of the present invention to provide novel compounds of the present invention for use in therapy.

It is another object of the present invention to provide the use of novel compounds of the present invention for the manufacture of a medicament for the treatment of a condition or disease mediated by MMPS, TACE, aggrecanase, or a combination thereof.

These and other objects, which will become apparent during the following detailed description, have been achieved by the inventors' discovery that compounds of formula (I):

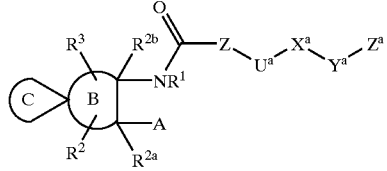

or pharmaceutically acceptable salt or prodrug forms thereof, wherein A, B, C, $R^1$, $R^2$, $R^{2a}$, $R^{2b}$, $R^3$, Z, $U^a$, $X^a$, $Y^a$, and $Z^a$ are defined below, are effective metalloprotease inhibitors.

DETAILED DESCRIPTION OF PREFERRED EMBODIMENTS

[1] Thus, in an embodiment, the present invention provides a novel compound of formula I:

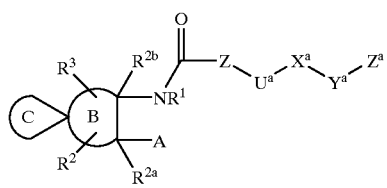

or a stereoisomer or pharmaceutically acceptable salt form thereof, wherein;

A is selected from —$COR^5$, —$CO_2H$, $CH_2CO_2H$, —$CO_2R^6$, —CONHOH, —$CONHOR^5$, —$CONHOR^6$, —N(OH)$COR^5$, —N(OH)CHO, —SH, —$CH_2SH$, —S(O)(=NH)$R^a$, —$SN_2H_2R^a$, —$PO(OH)_2$, and —$PO(OH)NHR^a$;

ring B is a 3–13 membered non-aromatic carbocycle or heterocycle comprising: carbon atoms, 0–3 carbonyl groups, 0–4 double bonds, and from 0–2 ring heteroatoms selected from O, N, $NR^2$, and $S(O)_p$, provided that ring B contains other than a S—S, O—O, or S—O bond;

ring C forms a spiro ring on Ring B and is a 3–13 membered carbocycle or heterocycle comprising: carbon atoms, 0–3 carbonyl groups, 0–4 double bonds, and from 0–5 ring heteroatoms selected from O, N, $NR^2$, and $S(O)_p$ and substituted with 0–6 $R^e$, provided that ring C contains other than a S—S, O—O, or S—O bond;

Z is absent or selected from a $C_{3-13}$ carbocycle substituted with 0–5 $R^b$ and a 5–14 membered heterocycle comprising: carbon atoms and 1–4 heteroatoms selected from the group consisting of N, O, and $S(O)_p$ and substituted with 0–5 $R^b$;

$U^a$ is absent or is selected from: O, $NR^{a1}$, C(O), C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, and $NR^{a1}SO_2NR^{a1}$;

$X^a$ is absent or selected from $C_{1-10}$ alkylene, $C_{2-10}$ alkenylene, and $C_{2-10}$ alkynylene;

$Y^a$ is absent or selected from O, $NR^{a1}$, $S(O)_p$, and C(O);

$Z^a$ is selected from H, a $C_{3-13}$ carbocycle substituted with 0–5 $R^c$ and a 5–14 membered heterocycle comprising: carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^1$ is selected from H, $C_{1-4}$ alkyl, phenyl, and benzyl;

$R^2$ is selected from Q, Cl, F, ($C_{1-10}$ alkylene substituted with 0–3 $R^{b1}$)—Q, ($C_{2-10}$ alkenylene substituted with 0–3 $R^{b1}$)—Q, ($C_{2-10}$ alkynylene substituted with 0–3 $R^{b1}$)—Q, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_{r1}C(O)O$—$C_{2-5}$ alkenylene, $(CR^aR^{a1})_{r1}C(O)O$—$C_{2-5}$ alkynylene, $(CR^aR^{a1})_{r1}OC(O)(CR^aR^{a1})_r$—Q, $(CR^aR^{a1})_{r1}C(O)NR^aR^{a1}$, $(CR^aR^{a1})_{r1}C(O)NR^a(CR^aR^{a1})_r$—Q, $(CR^aR^{a1})_{r1}NR^aC(O)(CR^aR^{a1})_r$—Q, $(CR^aR^{a1})_{r1}OC(O)(CR^aR^{a1})_r$—Q, $(CR^aR^{a1})_{r1}OC(O)NR^a(CR^aR^{a1})_r$—Q, $(CR^aR^{a1})_{r1}NR^aC(O)O(CR^aR^{a1})_r$—Q, $(CR^aR^{a1})_{r1}NR^aC(O)NR^a(CR^aR^{a1})_r$—Q, $(CR^aR^{a1})_{r1}S(O)_p(CR^aR^{a1})_r$—Q, $(CR^aR^{a1})_{r1}SO_2NR^a(CR^aR^{a1})_r$—Q, $(CR^aR^{a1})_{r1}NR^aSO_2(CR^aR^{a1})_r$—Q, and $(CR^aR^{a1})_{r1}NR^aSO_2NR^a(CR^aR^{a1})_r$—Q;

$R^{2a}$ is selected from H, $C_{1-6}$ alkyl, $OR^a$, $NR^aR^{a1}$, and $S(O)_pR^a$;

$R^{2b}$ is H or $C_{1-6}$ alkyl;

Q is selected from H, a $C_{3-13}$ carbocycle substituted with 0–5 $R^d$ and a 5–14 membered heterocycle comprising: carbon atoms and 1–4 heteroatoms selected from the group consisting of N, O, and $S(O)_p$ and substituted with 0–5 $R^d$;

$R^3$ is selected from $Q^1$, Cl, F, $C_{1-6}$ alkylene-$Q^1$, $C_{2-6}$ alkenylene-$Q^1$, $C_{2-6}$ alkynylene-$Q^1$, $(CR^aR^{a1})_{r1}O(CR^aR^{a1})_r$—$Q^1$, $(CR^aR^{a1})_{r1}NR^a(CR^aR^{a1})_r$—$Q^1$, $(CR^aR^{a1})_{r1}NR^aC(O)(CR^aR^{a1})_r$—$Q^1$, $(CR^aR^{a1})_{r1}C(O)NR^a(CR^aR^{a1})_r$—$Q^1$, $(CR^aR^{a1})_{r1}C(O)(CR^aR^{a1})_r$—$Q^1$, $(CR^aR^{a1})_{r1}C(O)O(CR^aR^{a1})_r$—$Q^1$, $(CR^aR^{a1}_2)_{r1}S(O)_p(CR^aR^{a1})_r$—$Q^1$, and $(CR^aR^{a1})_{r1}SO_2NR^a(CR^aR^{a1})_r$—$Q^1$;

$Q^1$ is selected from H, phenyl substituted with 0–3 $R^d$, naphthyl substituted with 0–3 $R^d$ and a 5–10 membered heteroaryl comprising: carbon atoms and 1–4 heteroatoms selected from the group consisting of N, O, and $S(O)_p$ and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, and $CF_2CF_3$;

$R^{b1}$, at each occurrence, is independently selected from $OR^a$, Cl, F, Br, I, =O, —CN, $NO_2$, and $NR^aR^{a1}$;

$R^c$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $CH_2F$, $CHF_2$, $CF_2CH_3$, $C(CH_3)_2$ F, $OCF_3$, $C_{3-10}$ carbocycle substituted with 0–3 $R^{c1}$ and a 5–14 membered heterocycle comprising: carbon atoms and 1–4 heteroatoms selected from the group consisting of N, O, and $S(O)_p$ and substituted with 0–3 $R^{c1}$;

alternatively, when two $R^c$ groups are attached to the same carbon atom, they form a spiro ring D that is a 3–11 membered carbocycle substituted with 0–2 $R^{c1}$ or a 3–13 membered heterocycle comprising: carbon atoms and from 1–4 ring heteroatoms selected from O, N, and $S(O)_p$ and substituted with 0–2 $R^{c1}$, provided that ring D contains other than a S—S, O—O, or S—O bond;

alternatively, when two $R^c$ groups are attached to adjacent carbon atoms, together with the carbon atoms to which they are attached they form a 5–7 membered saturated, partially saturated or unsaturated ring consisting of: carbon atoms and 0–2 heteroatoms selected from the group consisting of N, O, and $S(O)_p$; this ring is substituted with 0–2 $R^{c1}$;

$R^{c1}$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $CH_2F$, and $CHF_2$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle and a 5–14 membered heterocycle comprising: carbon atoms and 1–4 heteroatoms selected from the group consisting of N, O, and $S(O)_p$;

$R^e$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–2 $R^{c1}$, $(CR^aR^{a1})_{r1}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r1}$—5–14 membered heterocycle comprising carbon atoms and 1–4 heteroatoms selected from the group consisting of N, O, and $S(O)_p$ and substituted with 0–2 $R^{c1}$;

$R^5$, at each occurrence, is selected from $C_{1-10}$ alkyl substituted with 0–2 $R^b$, and $C_{1-8}$ alkyl substituted with 0–2 $R^f$;

$R^f$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$alkyl)-1,3-dioxa-cyclopenten-2-one-yl] methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^g$, $C_{3-8}$ cycloalkyl substituted with 1–2 $R^g$, and phenyl substituted with 0–2 $R^b$;

$R^g$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;
r, at each occurrence, is selected from 0, 1, 2, 3, and 4; and,
r1, at each occurrence, is selected from 0, 1, 2, 3, and 4.

[2] In a preferred embodiment, the present invention provides a novel compound of formula II:

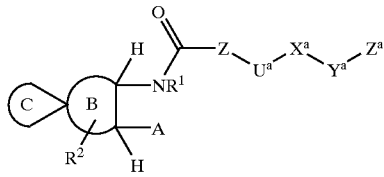

II or a stereoisomer or pharmaceutically acceptable salt form thereof, wherein;

A is selected from —$CO_2H$, $CH_2CO_2H$, —CONHOH, —$CONHOR^5$, —$CONHOR^6$, —$N(OH)COR^5$, —N(OH)CHO, —SH, and —$CH_2SH$;

ring B is a 4–7 membered non-aromatic carbocyclic or heterocyclic ring comprising: carbon atoms, 0–1 carbonyl groups, 0–1 double bonds, and from 0–2 ring heteroatoms selected from O, N, and $NR^2$, provided that ring B contains other than a O—O bond;

ring C forms a spiro ring on Ring B and is a 4–10 membered carbocycle substituted with 0–3 $R^e$ or a 4–10 membered heterocycle comprising: carbon atoms, 0–3 carbonyl groups, 0–4 double bonds, and from 0–4 ring heteroatoms selected from O, N, $NR^2$, and $S(O)_p$ and substituted with 0–3 $R^e$, provided that ring C contains other than a S—S, O—O, or S—O bond;

Z is absent or selected from a $C_{3-11}$ carbocycle substituted with 0–4 $R^b$ and a 5–11 membered heterocycle comprising: carbon atoms and 1–4 heteroatoms selected from the group consisting of N, O, and $S(O)_p$ and substituted with 0–3 $R^b$;

$U^a$ is absent or is selected from: O, $NR^{a1}$, C(O), C(O)O, $C(O)NR^{a1}$, $NR^{a1}C(O)$, $S(O)_p$, and $S(O)_pNR^{a1}$;

$X^a$ is absent or selected from $C_{1-4}$ alkylene, $C_{2-4}$ alkenylene, and $C_{2-4}$ alkynylene;

$Y^a$ is absent or selected from O and $NR^{a1}$;

$Z^a$ is selected from H, a $C_{3-10}$ carbocycle substituted with 0–5 $R^c$ and a 5–10 membered heterocycle comprising: carbon atoms and 1–4 heteroatoms selected from the group consisting of N, O, and $S(O)_p$ and substituted with 0–5 $R^c$;

provided that Z, $U^a$, $Y^a$, and $Z^a$ do not combine to form a N—N, N—O, O—N, O—O, $S(O)_p$—O, O—$S(O)_p$, or $S(O)_p$—$S(O)_p$ group;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_rC(O)NR^aR^{a1}$, $(CR^aR^{a1})_{r1}C(O)NR^a(CR^aR^{a1})_r$—Q, $(CR^aR^{a1})_{r1}S(O)_p(CR^aR^{a1})_r$—Q, and $(CR^aR^{a1})_{r1}SO_2NR^a(CR^aR^{a1})_r$—Q;

Q is selected from H, a $C_{3-6}$ carbocycle substituted with 0–5 $R^d$, and a 5–10 membered heterocycle comprising: carbon atoms and 1–4 heteroatoms selected from the group consisting of N, O, and $S(O)_p$ and substituted with 0–5 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

alternatively, $R^a$ and $R^{a1}$ when attached to a nitrogen are taken together with the nitrogen to which they are attached to form a 5 or 6 membered ring comprising carbon atoms and from 0–1 additional heteroatoms selected from the group consisting of N, O, and $S(O)_p$;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $CH_2F$, $CHF_2$, $CF_2CH_3$, $C(CH_3)_2F$, $OCF_3$, $C_{3-6}$ carbocycle substituted with 0–2 $R^{c1}$ and a 5–6 membered heterocycle comprising: carbon atoms and 1–4 heteroatoms selected from the group consisting of N, O, and $S(O)_p$ and substituted with 0–2 $R^{c1}$;

alternatively, when two $R^c$ groups are attached to adjacent carbon atoms, together with the carbon atoms to which they are attached they form a 5–6 membered saturated, partially saturated or unsaturated ring consisting of: carbon atoms and 0–2 heteroatoms selected from the group consisting of N, O, and $S(O)_p$;

$R^{c1}$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $CH_2F$, and $CHF_2$;

$R^d$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $C_{3-6}$ carbocycle and a 5–6 membered heterocycle comprising: carbon atoms and 1–4 heteroatoms selected from the group consisting of N, O, and $S(O)_p$;

$R^e$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–2 $R^{c1}$, $(CR^aR^{a1})_{r1}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r1}$-5–14 membered heterocycle comprising carbon atoms and 1–4 heteroatoms selected from the group consisting of N, O, and $S(O)_p$ and substituted with 0–2 $R^{c1}$;

$R^5$, at each occurrence, is selected from $C_{1-6}$ alkyl substituted with 0–2 $R^b$, and $C_{1-4}$ alkyl substituted with 0–2 $R^f$;

$R^f$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^g$, $C_{3-6}$ cycloalkyl substituted with 1–2 $R^g$, and phenyl substituted with 0–2 $R^b$;

$R^g$, at each occurrence, is selected from $C_{1-4}$ alkyl, $C_{3-6}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and, r1, at each occurrence, is selected from 0, 1, 2, 3, and 4.

[3] In another preferred embodiment, the present invention provides a novel compound of formula IIIa or IIIb:

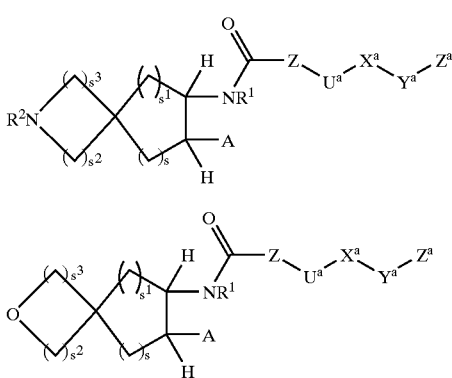

or a stereoisomer or pharmaceutically acceptable salt form thereof, wherein;

A is selected from —$CO_2H$, $CH_2CO_2H$, —CONHOH, —$CONHOR^5$, —N(OH)CHO, and —N(OH)$COR^5$;

Z is absent or selected from a $C_{5-6}$ carbocycle substituted with 0–3 $R^b$ and a 5–6 membered heteroaryl comprising carbon atoms and from 1–4 heteroatoms selected from the group consisting of N, O, and S(O)$_p$ and substituted with 0–3 $R^b$;

$U^a$ is absent or is selected from: O, $NR^{a1}$, C(O), C(O)$NR^{a1}$, S(O)$_p$, and S(O)$_p NR^{a1}$;

$X^a$ is absent or selected from $C_{1-4}$ alkylene, $C_{2-4}$ alkenylene, and $C_{2-4}$ alkynylene $Y^a$ is absent or selected from O and $NR^{a1}$;

$Z^a$ is selected from H, a $C_{5-10}$ carbocycle substituted with 0–3 $R^c$ and a 5–10 membered heterocycle comprising carbon atoms and from 1–4 heteroatoms selected from the group consisting of N, O, and S(O)$_p$ and substituted with 0–3 $R^c$;

provided that Z, $U^a$, $Y^a$, and $Z^a$ do not combine to form a N—N, N—O, O—N, O—O, S(O)$_p$—O, O—S(O)$_p$ or S(O)$_p$—S(O)$_p$ group;

$R^1$ is selected from H, $C_{1-4}$ alkyl, phenyl, and benzyl;

$R^2$ is selected from Q, $C_{1-6}$ alkylene-Q, $C_{2-6}$ alkenylene-Q, $C_{2-6}$ alkynylene-Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a2})_{r1}C(O)NR^aR^{a1}$, $(CR^aR^{a2})_{r1}C(O)NR^a(CR^aR^{a1})_r$—Q, and $(CR^aR^{a1})_{r1}S(O)_p(CR^aR^{a1})_r$—Q;

Q is selected from H, a $C_{3-6}$ carbocycle substituted with 0–3 $R^d$ and a 5–10 membered heterocycle comprising: carbon atoms and 1–4 heteroatoms selected from the group consisting of N, O, and S(O)$_p$ and substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl, and benzyl;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, $CH_2F$, $CHF_2$, $CF_2CH_3$, $C(CH_3)_2F$, cyclopropyl, 1-methylcyclopropyl, and cyclobutyl;

alternatively, when two $R^c$ groups are attached to adjacent carbon atoms, together with the carbon atoms to which they are attached they form a 5–6 membered saturated ring consisting of: carbon atoms and 0–2 heteroatoms selected from the group consisting of N, O, and S(O)$_p$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl;

$R^e$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–2 $R^{c1}$, $(CR^aR^{a1})_{r1}$—$C_{3-10}$ carbocycle substituted with 0–2 $R^{c1}$, a 5–14 membered heterocycle comprising carbon atoms and 1–4 heteroatoms selected from the group consisting of N, O, and S(O)$_p$ and substituted with 0–2 $R^{c1}$, and $(CR^aR^{a1})_{r1}$-5–14 membered heterocycle comprising carbon atoms and 1–4 heteroatoms selected from the group consisting of N, O, and S(O)$_p$ and substituted with 0–2 $R^{c1}$;

$R^5$, at each occurrence, is selected from $C_{1-4}$ alkyl substituted with 0–2 $R^b$, and $C_{1-4}$ alkyl substituted with 0–2 $R^f$;

$R^f$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4;

r1, at each occurrence, is selected from 0, 1, 2, 3, and 4;

s and $s^1$ combine to total 2, 3, or 4; and $s^2$ and $s^3$ combine to total 2, 3, 4, or 5.

[4] In another preferred embodiment, the present invention provides a novel compound of formula IVa or IVb:

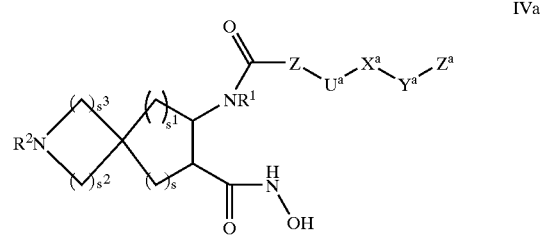

-continued

IVb

[structure diagram showing a spirocyclic compound with oxetane ring, NR¹ group connected to Z-Uᵃ-Xᵃ-Yᵃ-Zᵃ chain, and hydroxamic acid C(O)NHOH group, with ring size parameters s, s¹, s², s³]

or a stereoisomer or pharmaceutically acceptable salt form thereof, wherein;

Z is absent or selected from phenyl substituted with 0–3 $R^b$, pyridyl substituted with 0–3 $R^b$, thiazolyl substituted with 0–3 $R^b$, thienyl substituted with 0–3 $R^b$, and isoxazolyl substituted with 0–3 $R^b$;

$U^a$ is absent or is O;

$X^a$ is absent or is $CH_2$ or $CH_2CH_2$;

$Y^a$ is absent or is O;

$Z^a$ is selected from H, phenyl substituted with 0–3 $R^c$, and a 5–10 membered heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolyl;

provided that Z, $U^a$, $Y^a$, and $Z^a$ do not combine to form a N—N, N—O, O—N, or O—O group;

$R^1$ is selected from H, $CH_3$, and $CH_2CH_3$;

$R^2$ is selected from Q, $C_{1-6}$ alkylene-Q, $C_{2-6}$ alkynylene-Q, $C(O)(CR^aR^{a1})_r$—Q, $C(O)O(CR^aR^{a1})_r$—Q, $C(O)NR^a(CR^aR^{a1})_r$—Q, and $S(O)_p(CR^aR^{a1})_r$—Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$ and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, $CH_2F$, $CHF_2$, $CF_2CH_3$, $C(CH_3)_2F$, cyclopropyl, 1-methylcyclopropyl, and cyclobutyl;

alternatively, when two $R^c$ groups are attached to adjacent carbon atoms, together with the carbon atoms to which they are attached they form a 5–6 membered saturated ring consisting of: carbon atoms and 0–1 heteroatoms selected from the group consisting of N, O, and $S(O)_p$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

$R^e$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–2 $R^{c1}$, $(CR^aR^{a1})_{r1}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r1}$-5–14 membered heterocycle comprising carbon atoms and 1–4 heteroatoms selected from the group consisting of N, O, and $S(O)_p$ and substituted with 0–2 $R^{c1}$;

p, at each occurrence, is selected from 0, 1, and 2;

r, at each occurrence, is selected from 0, 1, 2, and 3;

r1, at each occurrence, is selected from 0, 1, 2, and 3;

s and $s^1$ combine to total 2, 3, or 4; and $s^2$ and $s^3$ combine to total 2, 3, 4, or 5.

[5] In another preferred embodiment, the present invention provides a novel compound of formula IVa or IVb, wherein;

Z is absent or selected from phenyl substituted with 0–3 $R^b$ and pyridyl substituted with 0–3 $R^b$;

$U^a$ is absent or is O;

$X^a$ is absent or is $CH_2$ or $CH_2CH_2$;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that Z, $U^a$, $Y^a$, and $Z^a$ do not combine to form a N—N, N—O, O—N, or O—O group;

$R^1$ is selected from H, $CH_3$, and $CH_2CH_3$;

$R^2$ is selected from Q, $C_{1-6}$ alkylene-Q, $C_{2-6}$ alkynylene-Q, $C(O)(CR^aR^{a1})_r$—Q, $C(O)O(CR^aR^{a1})_r$—Q, $C(O)NR^a(CR^aR^{a1})_r$—Q, and $S(O)_p(CR^aR^{a1})_r$—Q;

Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H, $CH_3$, and $CH_2CH_3$;

$R^{a1}$, at each occurrence, is independently selected from H, $CH_3$, and $CH_2CH_3$;

$R^{a2}$, at each occurrence, is independently selected from H, $CH_3$, and $CH_2CH_3$;

$R^b$, at each occurrence, is independently selected from $C_{1-4}$ alkyl, $OR^a$, Cl, F, =O, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, and $CF_3$;

$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$ and phenyl;

$R^e$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2$ $R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–2 $R^{c1}$, $(CR^aR^{a1})_{r1}$—$C_{3-10}$ carbocycle substituted with 0–2 $R^{c1}$, a 5–14 membered heterocycle comprising carbon atoms and 1–4 heteroatoms selected from the group consisting of N, O, and $S(O)_p$ and substituted with 0–2 $R^{c1}$, and $(CR^aR^{a1})_{r1}$-5–14 membered heterocycle comprising carbon atoms and 1–4 heteroatoms selected from the group consisting of N, O, and S(O)$_p$ and substituted with 0–2 R$^{c1}$;
p, at each occurrence, is selected from 0, 1, and 2;
r, at each occurrence, is selected from 0, 1, 2, and 3;
r1, at each occurrence, is selected from 0, 1, 2, and 3;
s and s$^1$ combine to total 2, 3, or 4; and
s$^2$ and s$^3$ combine to total 2, 3, 4, or 5.

[6] In another preferred embodiment, the present invention provides a novel compound of formula IVa or IVb, wherein;

Z is phenyl, thiazolyl, thienyl or isoxazolyl;
U$^a$ is absent or is O;
X$^a$ is absent or is CH$_2$ or CH$_2$CH$_2$;
Y$^a$ is absent or is O;
Z$^a$ is a 5–10 membered heterocycle substituted with 0–2 R$^c$ and selected from the group: 4-pyridyl, 4-quinolinyl, 1H-benzimidazol-1-yl, 1H-indol-1-yl, and 1H-indol-3-yl, 1,1-dioxido-2,3-dihydro-4H-1,4-benzothiazin-4-yl;
R$^1$ is H;
R$^c$, at each occurrence, is independently selected from methyl, ethyl, propyl, isopropyl, butyl, t-butyl, CF$_3$, CHF$_2$, CH$_2$F, CF$_2$CH$_3$, C(CH$_3$)$_2$F, NH$_2$, NH(CH$_3$), N(CH$_3$)$_2$, cyclopropyl, 1-methylcyclopropyl, and cyclobutyl;
s and s$^1$ combine to total 2, 3, or 4; and
s$^2$ and s$^3$ combine to total 2, 3, 4, or 5.

[7] In another preferred embodiment, the present invention provides a compound selected from the group:

(7S,8R)-N-hydroxy-8-({4-[(2-methyl-4-quinolinyl)methoxy]benzoyl}amino)-1,4-dioxaspiro[4.4]nonane-7-carboxamide;
(5R,7S,8R)-N-hydroxy-8-({4-[(2-methyl-4-quinolinyl)methoxy]benzoyl}amino)-1-oxaspiro[4.4]nonane-7-carboxamide;
(5S,7S,8R)-N-hydroxy-8-({4-[(2-methyl-4-quinolinyl)methoxy]benzoyl}amino)-1-oxaspiro[4.4]nonane-7-carboxamide;
(2S,3R)-N-hydroxy-3-({4-[(2-methyl-4-quinolinyl)methoxy]benzoyl}amino)-6,10-dioxaspiro[4.5]decane-2-carboxamide;
(7S,8R)-N-hydroxy-8-({4-[(2-methyl-4-quinolinyl)methoxy]benzoyl}amino)-1,4-dithiaspiro[4.4]nonane-7-carboxamide;
(5R,7S,8R)-8-{[4-(2-butynyloxy)benzoyl]amino}-N-hydroxy-1-oxaspiro[4.4]nonane-7-carboxamide;
(5R,7S,8R)-N-hydroxy-8-({4-[(2-methyl-1H-benzimidazol-1-yl)methyl]benzoyl}amino)-1-oxaspiro[4.4]nonane-7-carboxamide;
(5R,7S,8R)-N-hydroxy-8-({4-[(2-isopropyl-1H-benzimidazol-1-yl)methyl]benzoyl}amino)-1-oxaspiro[4.4]nonane-7-carboxamide;
(5R,7S,8R)-N-hydroxy-8-[(4-{[2-(trifluoromethyl)-1H-benzimidazol-1-yl]methyl}benzoyl)amino]-1-oxaspiro[4.4]nonane-7-carboxamide;
(5R,7S,8R)-8-({4-[(2-tert-butyl-1H-benzimidazol-1-yl)methyl]benzoyl}amino)-N-hydroxy-1-oxaspiro[4.4]nonane-7-carboxamide;
(5R,7S,8R)-N-hydroxy-8-({4-[(2-methyl-1H-indol-3-yl)methyl]benzoyl}amino)-1-oxaspiro[4.4]nonane-7-carboxamide;
(5R,7S,8R)-8-[(4-{[2-(difluoromethyl)-1H-benzimidazol-1-yl]methyl}benzoyl)amino]-N-hydroxy-1-oxaspiro[4.4]nonane-7-carboxamide;
(5R,7S,8R)-8-({4-[(2-cyclopropyl-1H-benzimidazol-1-yl)methyl]benzoyl}amino)-N-hydroxy-1-oxaspiro[4.4]nonane-7-carboxamide;
(5R,7S,8R)-8-({4-[(2-cyclobutyl-1-H-benzimidazol-1-yl)methyl]benzoyl}amino)-N-hydroxy-1-oxaspiro[4.4]nonane-7-carboxamide;
(5R,7S,8R)-N-hydroxy-8-({4-[(2-isopropyl-1H-imidazol-1-yl)methyl]benzoyl}amino)-1-oxaspiro[4.4]nonane-7-carboxamide;
(5R,7S,8R)-N-hydroxy-8-({4-[(2-methyl-1H-indol-1-yl)methyl]benzoyl}amino)-1-oxaspiro[4.4]nonane-7-carboxamide;
(5R,7S,8R)-N-hydroxy-8-[(4-{[2-(1-methylcyclopropyl)-1H-benzimidazol-1-yl]methyl}benzoyl)amino]-1-oxaspiro[4.4]nonane-7-carboxamide;
(5R,7S,8R)-8-[(4-{[2-(fluoromethyl)-1H-benzimidazol-1-yl]methyl}benzoyl)amino]-N-hydroxy-1-oxaspiro[4.4]nonane-7-carboxamide;
(5R,7S,8R)-8-[(4-{[2-(1-fluoro-1-methylethyl)-1H-benzimidazol-1-yl]methyl}benzoyl)amino]-N-hydroxy-1-oxaspiro[4.4]nonane-7-carboxamide;
(5R,7S,8R)-N-hydroxy-8-{[4-(1H-indol-3-ylmethyl)benzoyl]amino}-1-oxaspiro[4.4]nonane-7-carboxamide;
(5R,7S,8R)-8-[(4-{[2-(1,1-difluoroethyl)-1H-benzimidazol-1-yl]methyl}benzoyl)amino]-N-hydroxy-1-oxaspiro[4.4]nonane-7-carboxamide;
(5R,7S,8R)-8-({4-[(2,3-dimethyl-1H-indol-1-yl)methyl]benzoyl}amino)-N-hydroxy-1-oxaspiro[4.4]nonane-7-carboxamide;
(5R,7S,8R)-8-({4-[(2-ethyl-1H-indol-3-yl)methyl]benzoyl}amino)-N-hydroxy-1-oxaspiro[4.4]nonane-7-carboxamide;
(5R,7S,8R)-N-hydroxy-8-[(4-{[2-(trifluoromethyl)-1H-indol-1-yl]methyl}benzoyl)amino]-1-oxaspiro[4.4]nonane-7-carboxamide;
(5R,7S,8R)-8-{[4-(1,1-dioxido-3,4-dihydro-2H-1-benzothiopyran-4-yl)benzoyl]amino}-N-hydroxy-1-oxaspiro[4.4]nonane-7-carboxamide;
(5R,7S,8R)-8-{[4-(3,4-dihydro-2H-chromen-4-yl)benzoyl]amino}-N-hydroxy-1-oxaspiro[4.4]nonane-7-carboxamide;
(5R,7S,8R)-8-{[4-(2H-chromen-4-yl)benzoyl]amino}-N-hydroxy-1-oxaspiro[4.4]nonane-7-carboxamide;
N-{(5R,7R,8S)-8-[(hydroxyamino)carbonyl]-1-oxaspiro[4.4]non-7-yl}-2-[(2-isopropyl-1H-benzimidazol-1-yl)methyl]-1,3-thiazole-4-carboxamide;
(5R,7S,8R)-8-({4-[(3,5-dimethyl-1H-pyrazol-4-yl)methyl]benzoyl}amino)-N-hydroxy-1-oxaspiro[4.4]nonane-7-carboxamide;
(5R,7S,8R)-N-hydroxy-8-({4-[(1,3,5-trimethyl-1H-pyrazol-4-yl)methyl]benzoyl}amino)-1-oxaspiro[4.4]nonane-7-carboxamide;
(5R,7S,8R)-8-({4-[(1,1-dioxido-2,3-dihydro-4H-1,4-benzothiazin-4-yl)methyl]benzoyl}amino)-N-hydroxy-1-oxaspiro[4.4]nonane-7-carboxamide;
(5R,7S,8R)-8-({4-[(2,2-dimethyl-1,1-dioxido-2,3-dihydro-4H-1,4-benzothiazin-4-yl)methyl]benzoyl}amino)-N-hydroxy-1-oxaspiro[4.4]nonane-7-carboxamide;
(5R,7S,8R)-N-hydroxy-8-({4-[(2-methyl-4-quinolinyl)methyl]benzoyl}amino)-1-oxaspiro[4.4]nonane-7-carboxamide;
(5R,7S,8R)-N-hydroxy-8-[(4-{[2-(trifluoromethyl)-4-quinolinyl]methyl}benzoyl)amino]-1-oxaspiro[4.4]nonane-7-carboxamide;
(5R,7S,8R)-8-({4-[(2-ethyl-4-quinolinyl)methyl]benzoyl}amino)-N-hydroxy-1-oxaspiro[4.4]nonane-7-carboxamide;
(5R,7S,8R)-N-hydroxy-8-({4-[(2-isopropyl-4-quinolinyl)methyl]benzoyl}amino)-1-oxaspiro[4.4]nonane-7-carboxamide
(5R,7S,8R)-8-[(4-{[2-(dimethylamino)-4-quinolinyl]methyl}benzoyl)amino]-N-hydroxy-1-oxaspiro[4.4]nonane-7-carboxamide;
(5R,7S,8R)-8-({4-[(2-cyclopropyl-4-quinolinyl)methyl]benzoyl}amino)-N-hydroxy-1-oxaspiro[4.4]nonane-7-carboxamide;

(5R,7S,8R)-8-{[4-(1,3-dihydrofuro[3,4-b]quinolin-9-ylmethyl)benzoyl]amino}-N-hydroxy-1-oxaspiro[4.4]nonane-7-carboxamide;
(5R,7S,8R)-8-({4-[(2,3-dimethyl-4-quinolinyl)methyl]benzoyl}amino)-N-hydroxy-1-oxaspiro[4.4]nonane-7-carboxamide;
(5R,7S,8R)-N-hydroxy-8-[(4-{[2-methyl-8-(trifluoromethyl)-4-quinolinyl]methyl}benzoyl)amino]-1-oxaspiro[4.4]nonane-7-carboxamide;
(5R,7S,8R)-8-({4-[(3-ethyl-2-methyl-4-quinolinyl)methyl]benzoyl}amino)-N-hydroxy-1-oxaspiro[4.4]nonane-7-carboxamide;
(5R,7S,8R)-8-({4-[(2,6-dimethyl-4-quinolinyl)methyl]benzoyl}amino)-N-hydroxy-1-oxaspiro[4.4]nonane-7-carboxamide;
(5R,7S,8R)-8-({4-[(6-chloro-2-methyl-4-quinolinyl)methyl]benzoyl}amino)-N-hydroxy-1-oxaspiro[4.4]nonane-7-carboxamide;
(5R,7S,8R)-8-({4-[(6-fluoro-2-methyl-4-quinolinyl)methyl]benzoyl}amino)-N-hydroxy-1-oxaspiro[4.4]nonane-7-carboxamide;
(5R,7S,8R)-8-({4-[(7-chloro-2-methyl-4-quinolinyl)methyl]benzoyl}amino)-N-hydroxy-1-oxaspiro[4.4]nonane-7-carboxamide; and
(5R,7S,8R)-8-({4-[(2,6-dimethyl-4-pyridinyl)methyl]benzoyl}amino)-N-hydroxy-1-oxaspiro[4.4]nonane-7-carboxamide; or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating or preventing an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, aggrecanase, or a combination thereof.

In another embodiment, the present invention provides a novel method of treating a disease or condition, wherein the disease or condition is referred to as acute infection, acute phase response, age related macular degeneration, alcoholism, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "independently selected from", "independently, at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2, 3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, and 3,4-dihydro-2H-chromen-4-yl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased increased anti-inflammatory effect, or some other beneficial effect of the combination compared with the individual components.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A variety of compounds of formula (I) wherein A is hydroxamic acid group are prepared from the corresponding esters via several routes known in the literature (Scheme 1). The methyl ester of 1 ($R^{11}$=Me) is directly converted to hydroxamic acid 2 by treatment with hydroxylamine under basic conditions such as KOH or NaOMe in solvents such as methanol. The methyl ester of 1 ($R^{11}$=Me) can also be converted to O-benzyl protected hydroxamic acid with O-benzylhydroxylamine under similar conditions or using Weinreb's trimethylaluminum conditions (Levin, J. I.; Turos, E.; Weinreb, S. M. *Syn. Commun.* 1982, 12, 989) or Roskamp's bis[bis(trimethylsilyl)amido]tin reagent (Wang, W.-B.; Roskamp, E. J. *J. Org. Chem.* 1992, 57, 6101). The benzyl ether is removed by methods well known in the literature such as hydrogenation using palladium on barium sulfate in hydrogen, to give compound 2. Alternatively, 2 can be prepared through the carboxylic intermediate 3. Carboxylic acid 3 is converted to 2 via coupling with hydroxylamine, or O-benzylhydroxylamine followed by deprotection.

Scheme 1

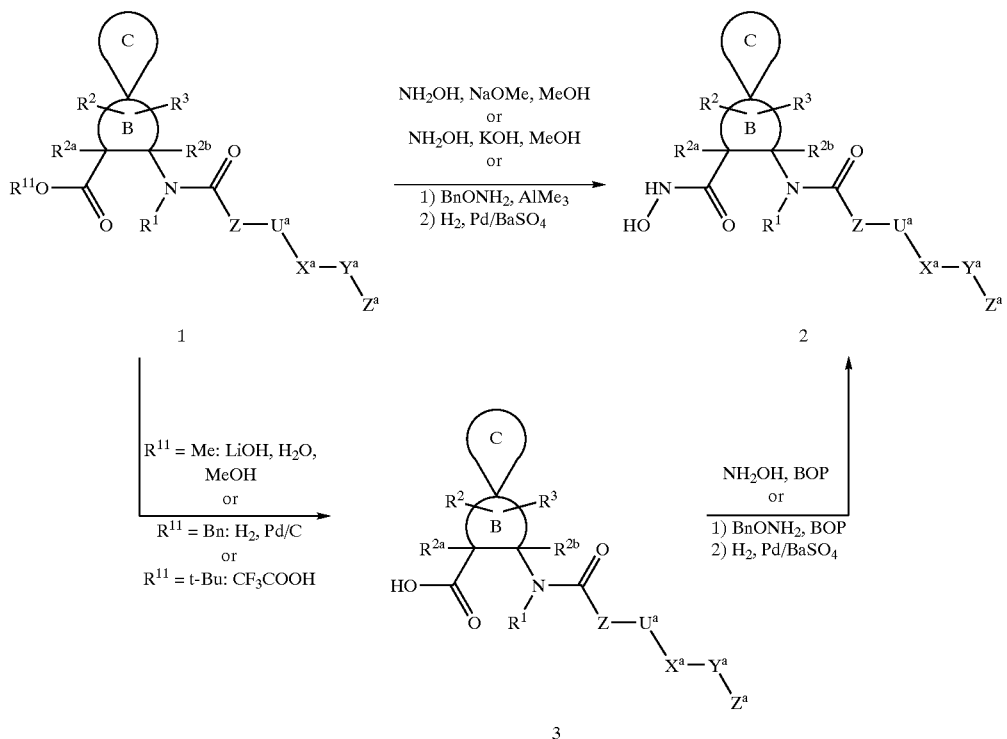

The β-amino acid moiety in formula (I) can be synthesized following a variety of literature routes as reviewed in "Enantioselective Synthesis of β-Amino Acids" (E. Juaristi, Ed. Wiley-VCH, 1997). One representative approach using Davies protocol is summarized in Scheme 2 (*J. Chem. Soc. Perkin Trans I*, 1994, 1411). Michael addition of lithium amide 5 to 4 gives cis product 6. The stereochemical configuration of 6 is governed by the chirality of 5. De-benzylation of 6 provides cis-β-amino acid 7. The trans-β-amino acid 9 can be prepared by epimerization of 6 followed by de-benzylation. Since both amine enantiomers of 5 are commercially available, this approach provides ready access to both cis and trans isomers (7 and 9), as well as their antipodes.

Scheme 2

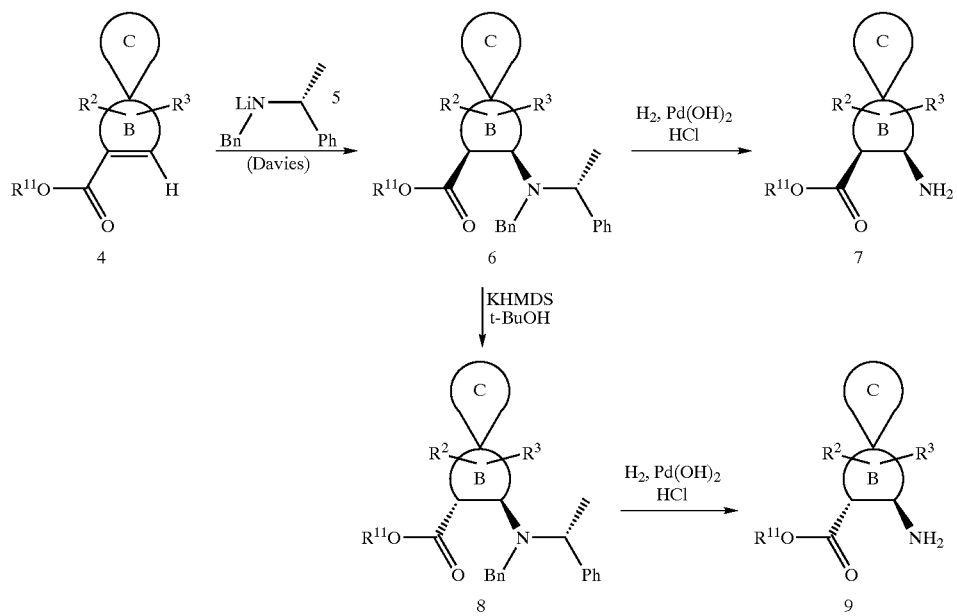

Alternatively, these β-amino acids can be prepared from the corresponding dicarboxylate derivatives (Scheme 3). The dicarboxylate derivatives can be de-symmetrized through enzymatic resolution (for an example with lipase, see Gais, H.-J. et al, *J. Am. Chem. Soc.* 1989, 54, 5115), or through chemical resolution (for an example with TADOLates, see Seebach, D. et al. *Angew. Chem. Int. Ed. Engl.* 1995, 34, 2395). The optically pure mono-ester 11 is converted to Cbz protected β-amino acid ester 12 through Curtius rearrangement (for a related example, see Kobayashi, S. et al. *Tetrahedron Lett.* 1984, 25, 2557). Removal of Cbz protecting group provides cis-amino acid ester 13. The corresponding trans analogue of 13 can be prepared from the ester of trans di-carboxylic acid of 10 following same sequence.

Hydrogenolysis gives amino acid ester 21. 21 is coupled with acid 22 to provide 23. Which is converted to the hydroxamic acid 24.

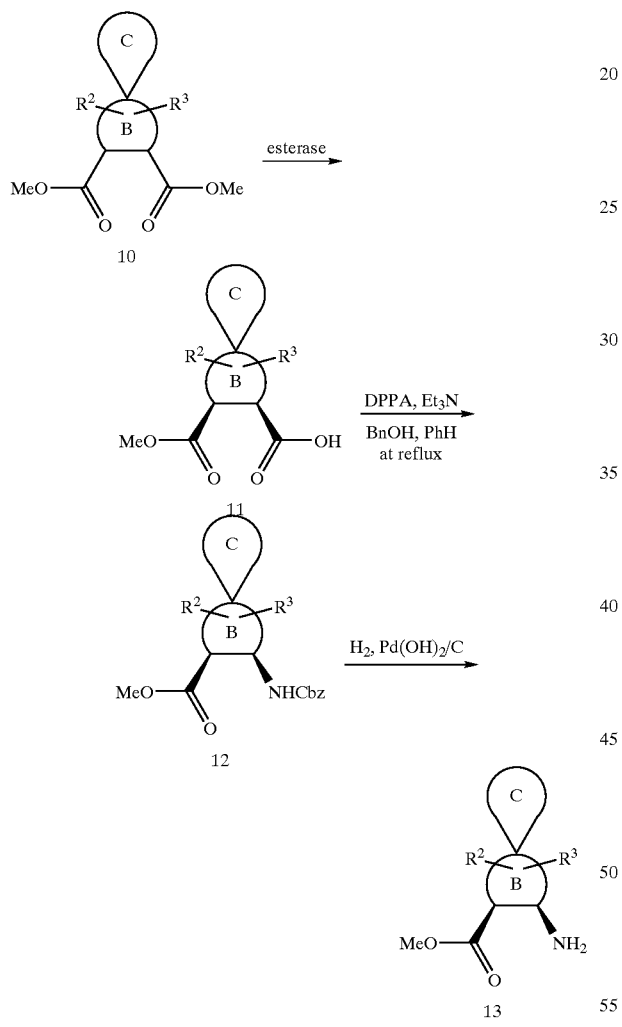

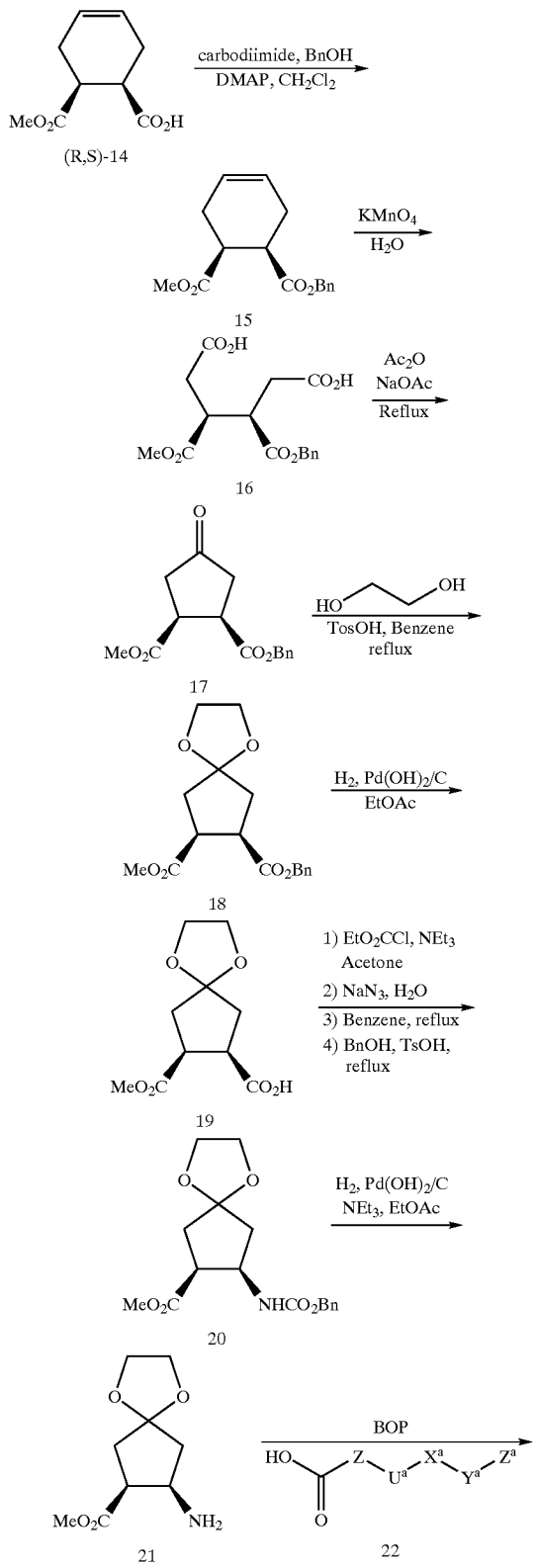

A series of compounds of formula (I) wherein ring B is a cyclopentane and ring C is a dioxolane are prepared following the sequence outlined in Scheme 4. The acid of compound 14 can be protected as the benzyl ester and the cyclohexene 15 is oxidized to the bis-acid and cyclized to the ketone 17 (for a related example see: Gais et al. *J. Org. Chem.* 1989, 54, 5115). The ketone is converted to the ethylene ketal 18. Protecting group manipulations and Curtius rearrangement (for a related example, see Kobayashi, S. et al, *Tetrahedron Lett.* 1984, 25, 2557) give intermediate 20.

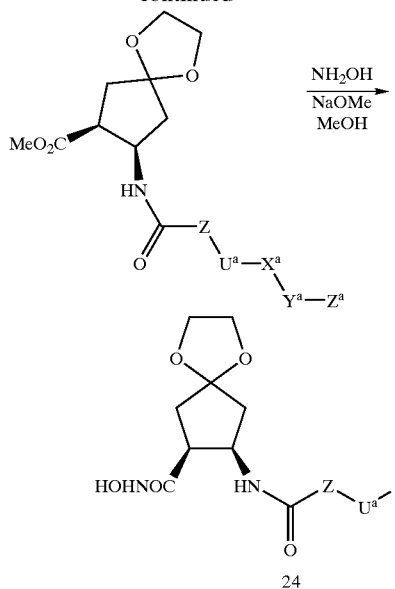

A series of compounds of formula (I) wherein ring B is cyclopentane and ring C is a tetrahydrofuran are prepared following the sequence outlined in Scheme 6. Ketone 17 is treated with allyltrimethylsilane in the presence of titanium tetrachloride to give 28, hydroboration/oxidation yields the primary alcohol which is cyclized to the the tetrahydrofuran 30. Conversion of 30 to the desired amine 33 and then amide and finally hydroxamic acid 34 proceeds through the steps as previously described.

Scheme 6

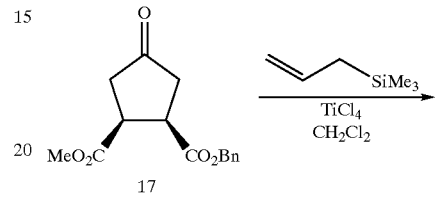

A series of compounds of formula (I) wherein ring B is cyclopentane and ring C is a dioxane, dioxepane, dithialane, dithiane, or dithiepane are prepared following the sequence outlined in Scheme 5. The ethylene ketal 23 deketalized with HCl and the resultant ketone reketalized with the appropriate diol or thiol to give 25 and 26 respectively, which can be converted as previously described to the desired hydroxamic acid.

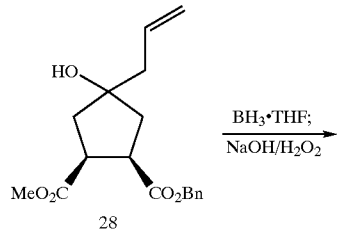

Scheme 5

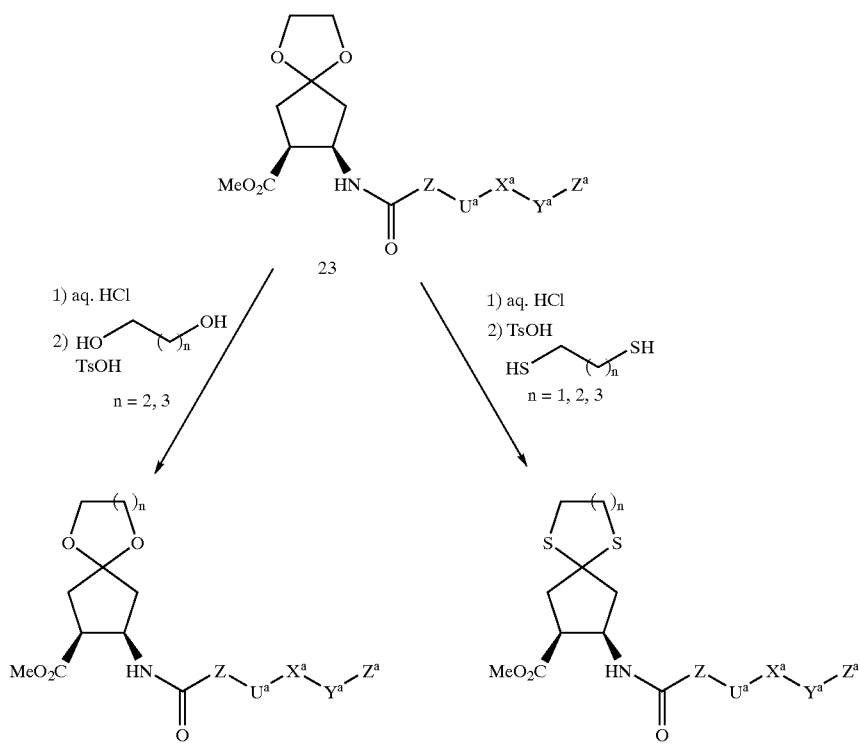

nylphosphorane followed by a hydroboration/oxidation sequence to deliver diol 35. Cyclization followed by a similar sequece as described earlier delivers 40.

Scheme 7

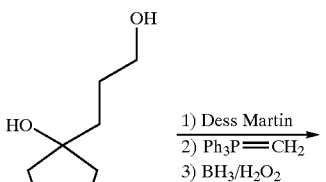

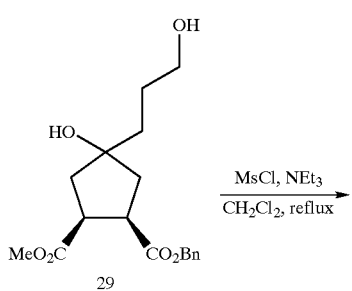

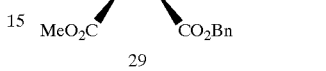

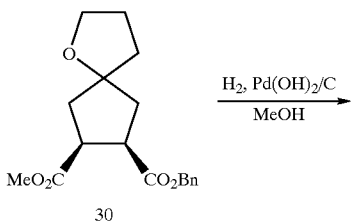

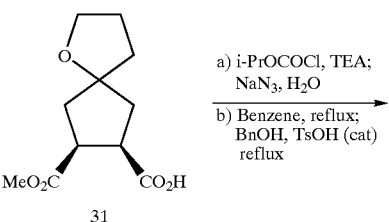

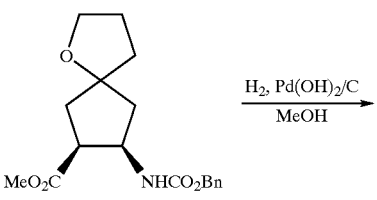

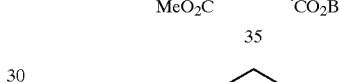

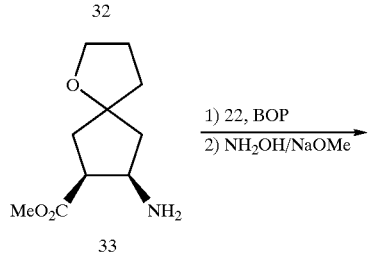

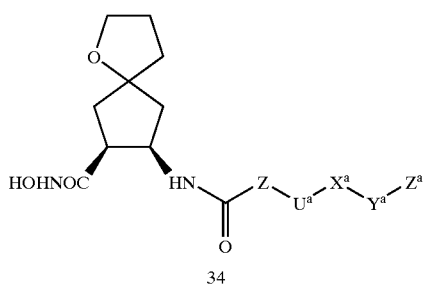

A series of compounds of formula (I) wherein ring B is cyclopentane and ring C is a tetrahydropyran are prepared following the sequence outlined in Scheme 7. Alcohol 29 is oxidized and converted to the olefin using methylene trphe-

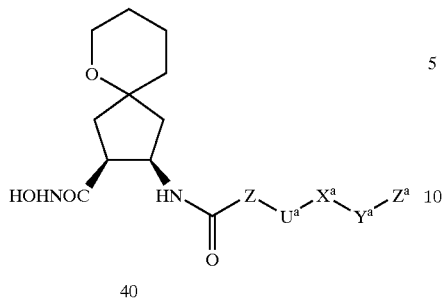

40

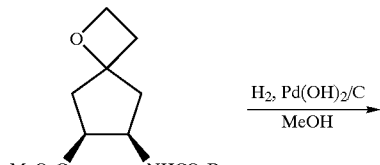

45

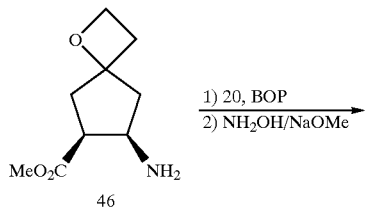

46

A series of compounds of formula (I) wherein ring B is cyclopentane and ring C is an oxetane are prepared following the sequence outlined in Scheme 8. Olefin 28 is ozonized and reduced the diol 41. Conversion to the primary bromide followed by cycliztion (NaH, DMF) delivers the oxetane 43. Following a similar sequence as described earlier delivers 47.

Scheme 8

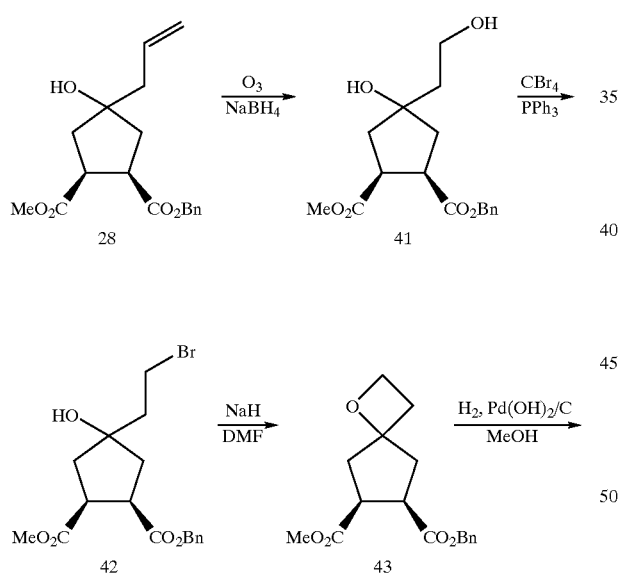

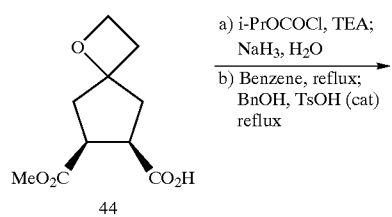

A series of compounds of formula (I) wherein ring B is a cyclopentane and ring C is an azetidine, pyrrolidine or a piperidine are prepared following the sequence outlined in Scheme 9. The benzylimine of ketone 17 is treated with Grignard reagent 58 (for a related example see: Berthe et. al. *Tetrahedron Letters*, 1997, 38, 1393–1396). The olefin 49 is then oxidized to the aldehyde 50. For azetidine formation (n=1) aldehyde 50 is reduced to the alcohol and cyclized using Mitsunobu conditions (for azetidine formation of benzyl amines using Mitsunobu conditions, see: Sammes and Smith, *J. Chem. Soc. Chem Commun.* 1983, 682). For pyrrolidine and piperidine formation (n=5,6), the aldehyde is converted to the desired ring by hydrogenolysis (for formation of 5 or 6-membered rings by reductive amination, see: Lubell, et al: *J. Org. Chem.* 1996, 61, 9447 and Watanabe, et al: *J. Org. Chem*, 1989, 54, 4088). Appropriate protection of the nitrogen is followed by conversion of the acid to a protected amine through a Curtius rearrangement to give 53. Protecting group manipulation and coupling to 22 yields 55. The BOC protecting group can be removed (TFA) and the nitrogen functionalized by amidation, alkylation, reductive amination, sulfonylation, etc. Conversion to the hydroxamate 57 proceeds as previously described.

Scheme 9

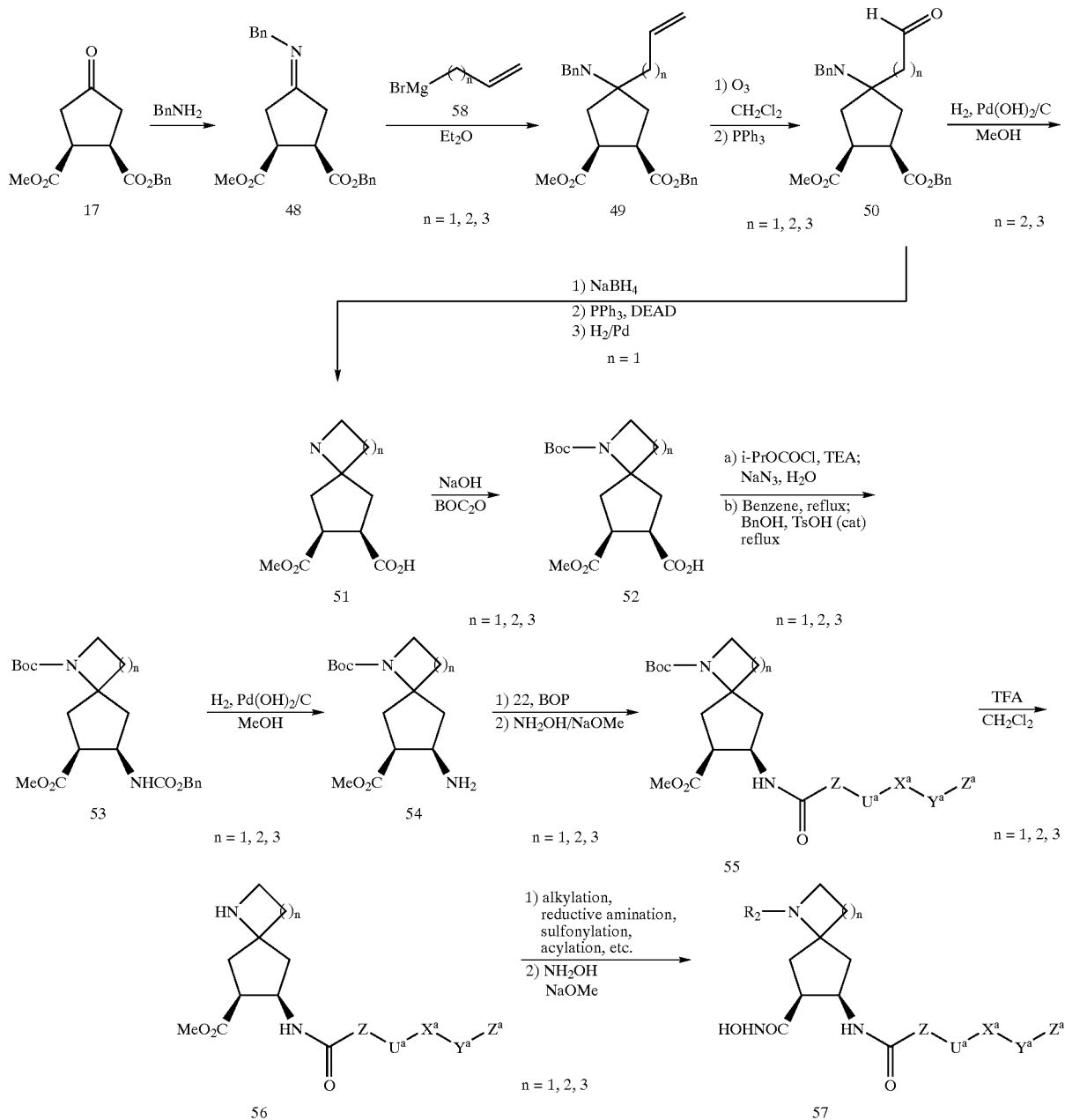

A series of compounds of formula (I) wherein A is N-formylhydroxylamino group are prepared following the sequence outlined in Scheme 10. Starting from trans-hydroxy ester 58, Wenreib or Roskamp amide formation with O-t-butylhydroxylamine gives 59 (Levin, J. I.; Turos, E.; Weinreb, S. M. *Syn. Commun.* 1982, 12, 989 and Wang, W.-B.; Roskamp, E. J. *J. Org. Chem.* 1992, 57, 6101). β-Lactam is formed under Mitsunobu conditions (Mitsunobu, O. *Synthesis*, 1981, 1). Opening of lactam 60 with methylamine followed by N-formylation provide 62. The N-methyl amide moiety of 62 is converted to carboxylic acid by nitrosation with N2O4 or NaNO2, and hydrolysis with LiOOH (Evans, D. A.; Carter, P. H.; Dinsmore, C. J.; Barrow, J. C.; Katz, J. L.; Kung, D. W. *Tetrahedron Lett.* 1997, 38, 4535). Acid 63 is converted to 66 as described previously. Acid hydrolysis of t-Butyl group in 66 completes the synthesis.

Scheme 10

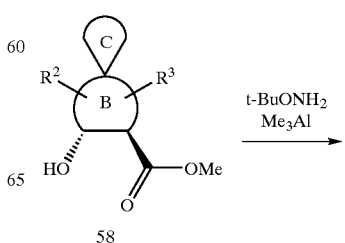

-continued
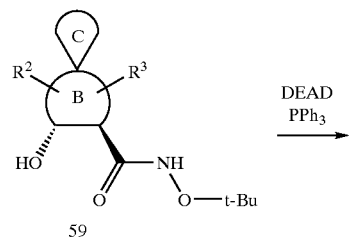
59
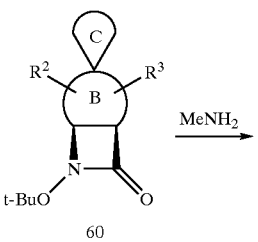
60
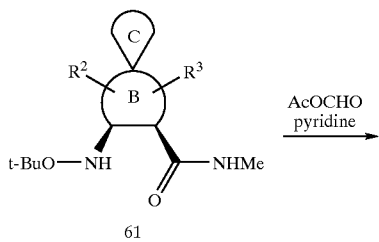
61
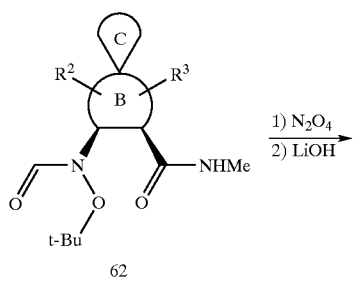
62
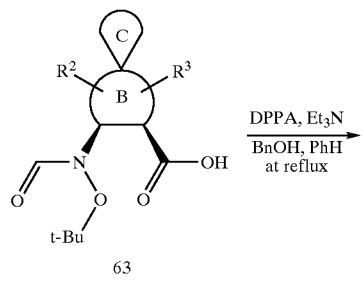
63
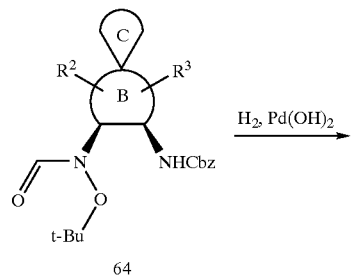
64
-continued
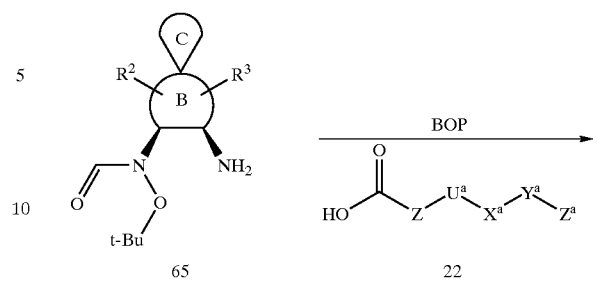
65
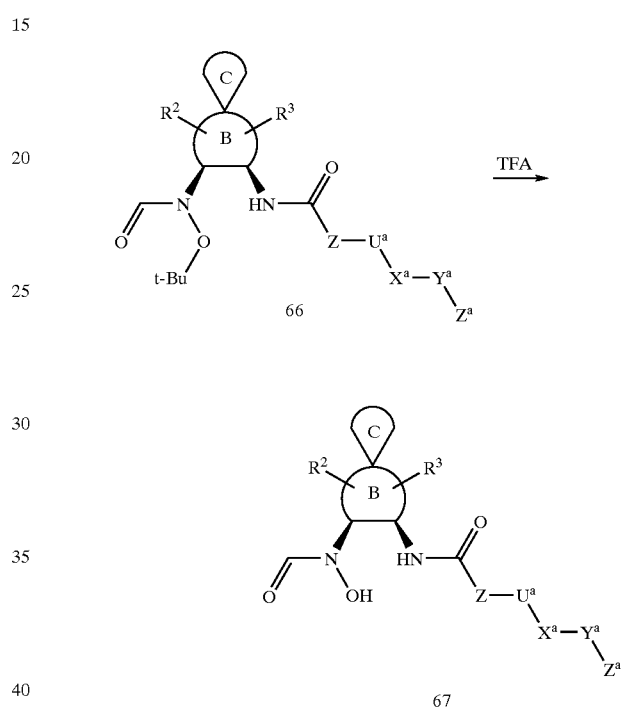
66
67
A series of compounds of formula (I) wherein A is mercaptomethyl group are prepared following the sequence outlined in Scheme 11. Saponification and hydroboration of 68 give alcohol 70. Mitsunobu reaction with thioacetic acid followed by lithium hydroxide hydrolysis provides the desired thiol 72.
Scheme 11
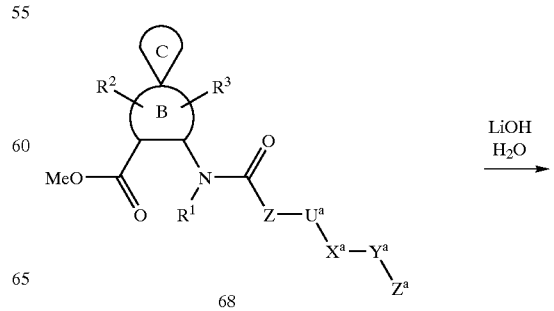
68

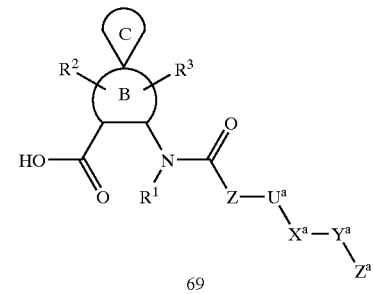

69

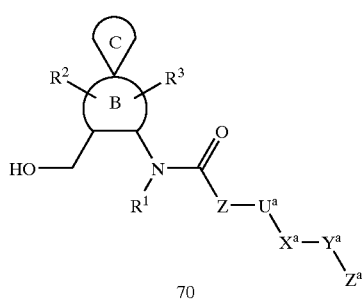

70

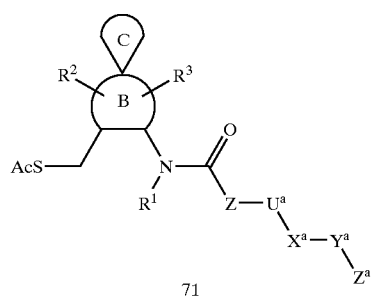

71

BH₃ →

MeCOSH
DEAD, PPh₃ →

LiOH →

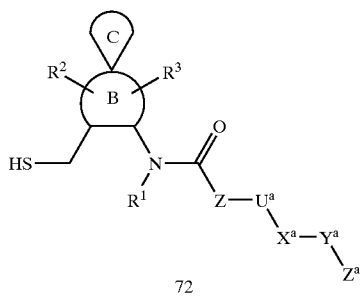

72

A variety of compounds of formula (I) wherein Z—U$^a$—X$^a$—Y$^a$—Z$^a$ is a functionalized phenyl group can be prepared by methods described in Scheme 12. Intermediate 73, available from schemes described previously, is converted to phenol 74 by hydrogenolysis. Phenol 74 is used as common intermediates for structure diversification. Reaction of 74 with R$^{10}$—X provides 75, an alternative is the reaction of 74 with R$^{10}$—OH under Mitsunobu conditions to produce 75. R$^{10}$ can be appended directly to the aromatic ring by converting 74 to an aryl triflate then reaction with an organometallic in the presence of a palladium (0) catalyst to give 76. 74 can also be reacted with acyl halides or isocyanates to afford 79. Biaryl ethers 78 can be produced by treatment of 74 with aryl boronic acids in the presence of a copper catalyst. Esters 74–76 and 78–79 are converted to the hydroxamic acids following the sequences outlined in Scheme 1.

Scheme 12

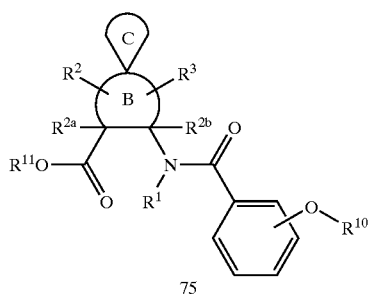

75

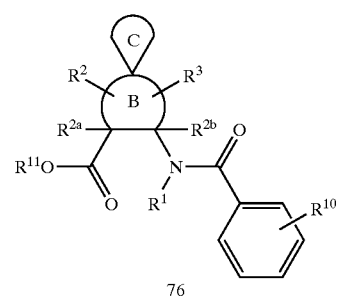

76

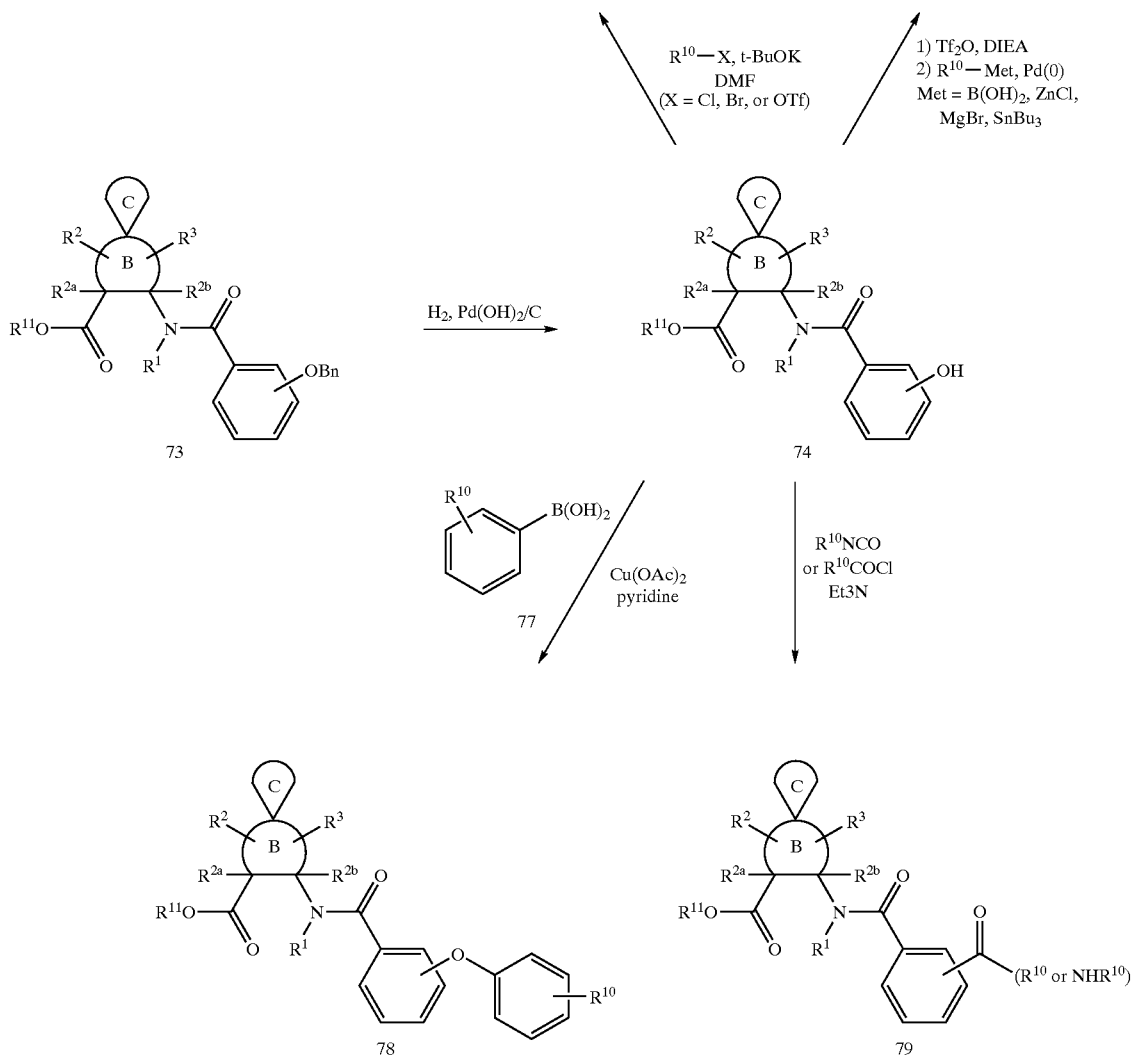

Another procedure for the synthesis of cyclic β-amino acids useful for the preparation of compounds of formula I uses the well documented [2+2] cycloaddition of chlorosulfonylisocyanate with olefins (Scheme 13, Dhar, D. N.; Murthy, K. S. K. *Synthesis* 1986, 437–449). When 80 is reacted with chlorosulfonylisocyanate the resulting β-lactam intermediate 81 can be opened to afford cyclic β-amino acids using a variety of conditions, but most conveniently with chlorotrimethylsilane/methanol. The methyl ester 13 can then be converted to compounds of formula I followed our usual procedure of attaching carboxcylic acid 20 to provide 82 then hydroxamic acid 83 is formed by our standard conditions. The trans β-amino acids 84 are available by equilibration of cis amide ester 82 under basic conditions.

Scheme 13

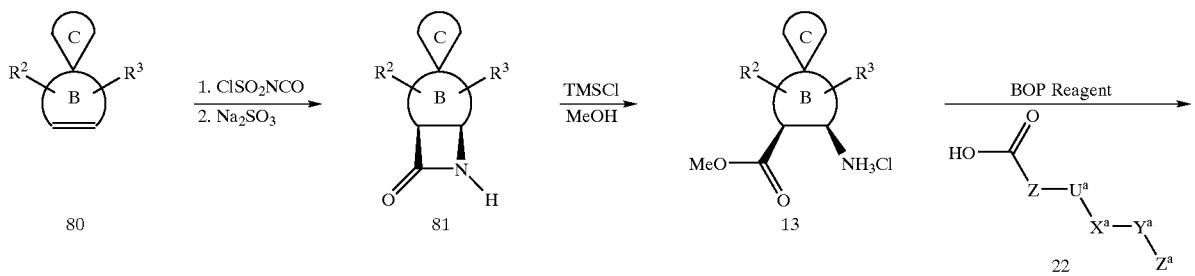

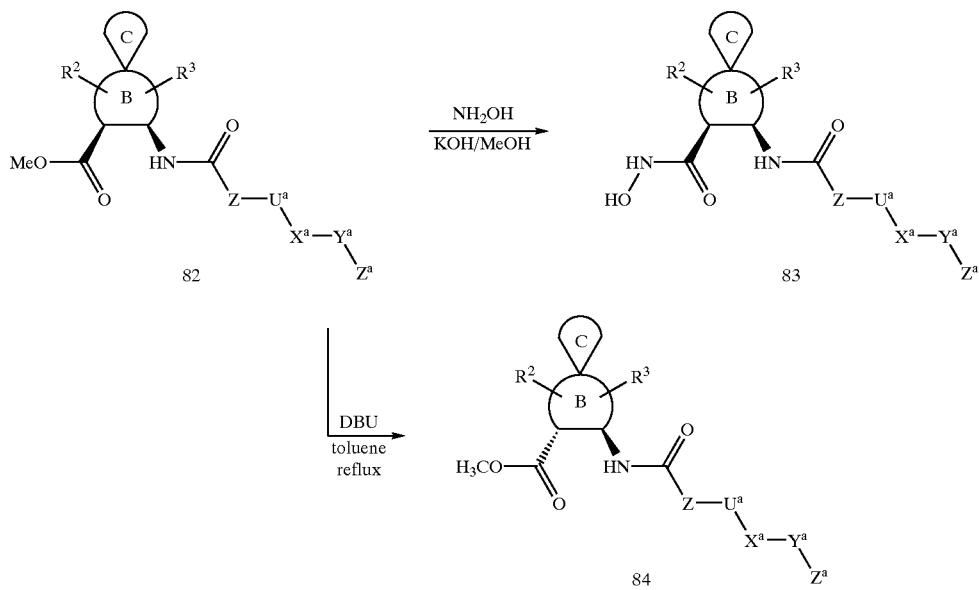

An alternative synthesis of 83 begins with formation of benzyl hydroxamate 86 from trans β-hydroxy carboxylate 85 (Scheme 14). Intramolecular cyclization of 86 under Mitsunobu conditions (Bellettini, J. R.; Miller, M. J. Tetrahedron Letters 1997, 38, 167–168) then affords benzyl protected hydroxy β-lactam 87. Removal of the benzyl group by hydrogenolysis and reduction of the intermediate N-hydroxy β-lactam provides 81, which can be converted to final products as shown in the previous scheme.

Scheme 14

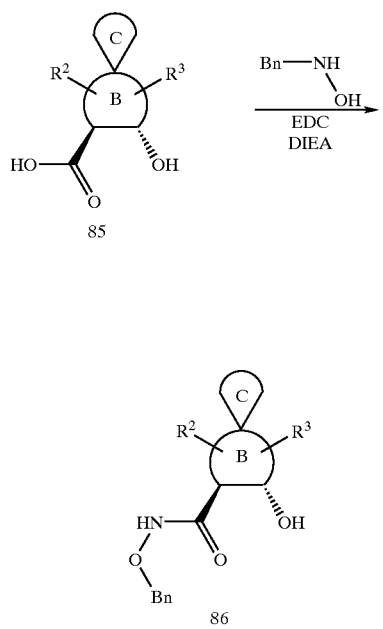

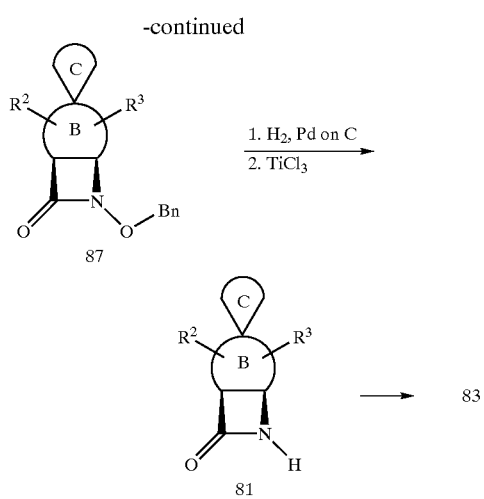

Outlined in Scheme 15 are compounds of Formula I wherein ring B is a cyclohexane. The regioisomeric ketones 88 and 89 are available from 15 via Wacker oxidation. The alcohols 90 and 91 are then available from previously described methods.

Scheme 15

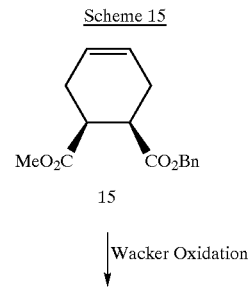

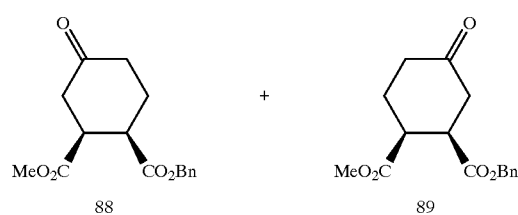
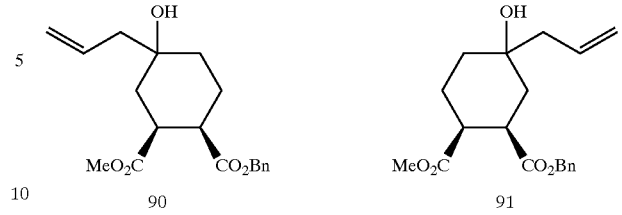
Alcohols 90 (Scheme 16) and 91 (Scheme 17) can then be converted to 4-, 5-, and 6-membered spirocyclic ethers following chemistry that was outlined in the previously noted schemes.
Scheme 16
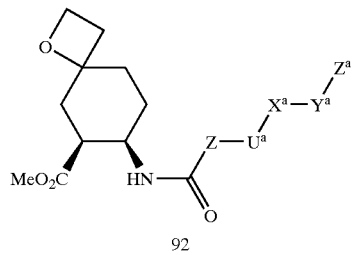
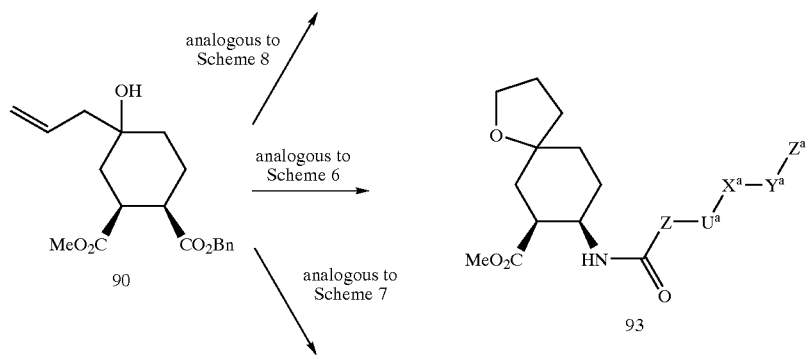
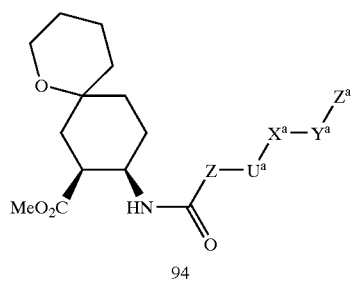

Scheme 17

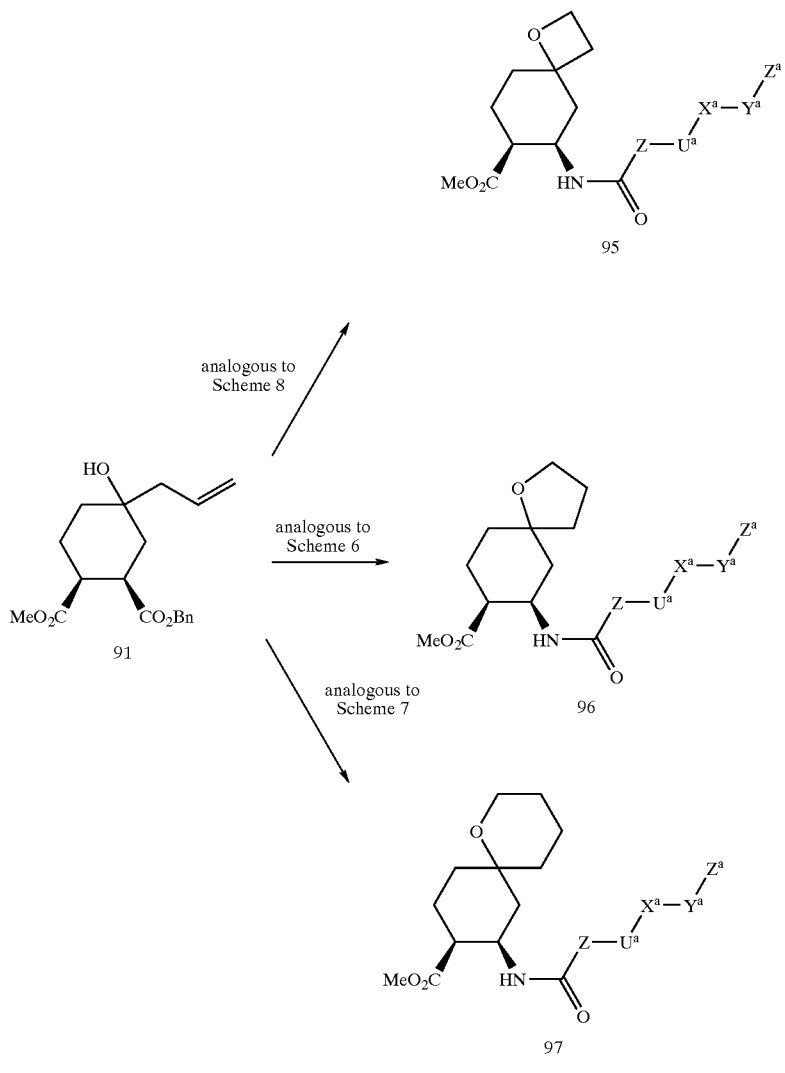

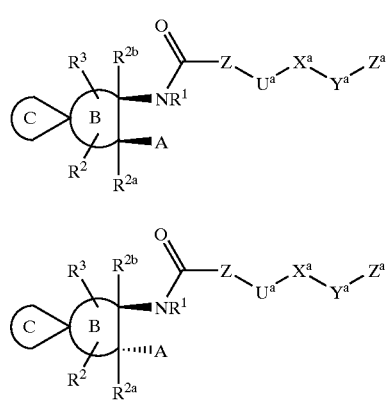

One diastereomer of a compound of Formula I may display superior activity compared with the others. Thus, the following stereochemistries are considered to be a part of the present invention.

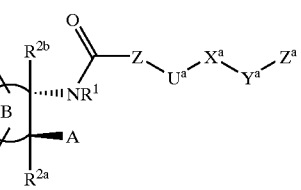

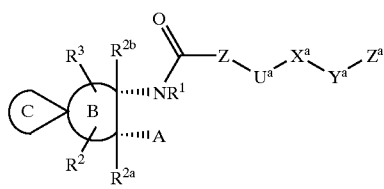

When required, separation of the racemic material can be achieved by HPLC using a chiral column or by a resolution using a resolving agent such as camphonic chloride as in Steven D. Young, et al. *Antimicrobial Agents and Chemotheraphy*, 1995, 2602–2605. A chiral compound of Formula I may also be directly synthesized using a chiral catalyst or a chiral ligand, e.g., Andrew S. Thompson, et al. *Tetrahedron Lett*. 1995, 36, 8937–8940.

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

(7S,8R)-N-hydroxy-8-({4-[(2-methyl-4-quinolinyl) methoxy]benzoyl}amino)-1,4-dioxaspiro[4.4] nonane-7-carboxamide (1a) 1-(3-Dimethylaminopropyl)-3-ethylcarbodiimide hydrochloride (73.0 g, 1.5 eq) was added to a mixture of (1S,2R)-1-methyl cis-1,2,3,6-tetrahydrophthalate (46.8 g, 254.2 mmol), benzyl alcohol (30.2 g, 1.1 eq) and 4-dimethylaminopyridine (3.0 g, 0.1 eq) in dichloromethane (470 mL) at 0° C. and let warm to room temperature. After 3 h, the solution was cooled to 0° C. and 1N HCl (300 mL) was added. The mixture was extracted with dichloromethane (2×300 mL). The organic layer was washed successively with brine (200 mL), dried (MgSO$_4$) and concentrated. The crude product (70 g) was purified by silica gel column chromatography (ethyl acetate-hexane, 1:10). The desired compound was obtained as colorless oil (68.8 g, 99%). MS found: (M+H)$^+$=275.

(1b) The olefin from reaction (1a) (68.8 g, 251 mmol) was added dropwise to a solution of potassium permanganate (125 g, 3.2 eq) in water (400 mL) at 0° C. After 20 min stirring at 0° C., TLC showed the presence of starting olefin. Another portion of water (400 mL) and potassium permanganate (125 g) were added. After 20 min the reaction was complete (by TLC). Sulfur dioxide was bubbled through the mixture at 0° C. until the color of the solution turned pink from purple (2 h). The mixture was filtered and the filtrate was acidified by adding concentrated HCl to pH=1. The reaction was extracted with ethyl acetate (5×500 mL) and the combined organic layers were dried over sodium sulfate. After filtration and concentration, the target diacid was obtained (74 g, 87% yield) and taken on without further purification. MS found (M+H)$^+$=339.

(1c) Sodium acetate (11.4 g, 138 mmol) was added to a solution of the dicarboxylic acid from reaction (1b) (57 g, 169 mmol) in acetic anhydride (43 g, 421 mmol) at rt. The reaction was refluxed for 2 h, and cooled to rt. Acetic anhydride was removed by rotary evaporation under reduced pressure. Water (600 mL) was added and the residue was extracted with ethyl acetate (1 L×2). The combined organic layers were dried over MgSO$_4$. After filtration and concentration, the crude ketone was obtained. Purification by silica gel column chromatography (Ethyl acetate 33% in hexane) furnished the target ketone (21 g, 45% yield). MS found: (M)$^+$=276.

(1d) The ketone from reaction (1c) (7 g, 25.3 mmol), ethylene glycol (15.7 g, 253.3 mmol) and p-toluenesulfonic acid monohydrate (481 mg, 2.5 mmol) were refluxed in benzene (507 mL) using Dean-Stark conditions for 1 h. After cooling, the reaction was quenched with saturated sodium bicarbonate solution (80 mL) and extracted with ethyl acetate (2×100 mL). The combined organic layers were washed with brine (80 mL), dried over magnesium sulfate, filtered and concentrated. The purification by silica gel column chromatography (Ethyl acetate 33% in hexane) furnished the target ketal (7.8 g, 97% yield). MS found: (M+H)$^+$=321.

(1e) The ketal from reaction (1d) (7.1 g, 22.3 mmol) and palladium hydroxide on carbon (20 wt %, 780 mg, 0.1 eq) were stirred in ethyl acetate (11 mL) under hydrogen (balloon) at rt for 45 min. After filtration and concentration, the target carboxylic acid (5.1 g, 99% yield) was obtained. MS found: (M+H)$^+$=231.

(1f) To a solution of the carboxylic acid from reaction (1e) (447 mg, 1.9 mmol) in acetone was added triethylamine (393 mg, 3.9 mmol) and ethyl chloroformate (316 mg, 2.9 mmol) at −25° C. under nitrogen. After stirring at rt for 10 min, sodium azide (316 mg, 4.9 mmol) dissolved in water (0.5 mL) was added to the mixture at −10° C. The reaction was stirred at rt for 1 h, and quenched with water (20 mL). It was extracted with CH$_2$Cl$_2$ (2×50 mL), washed with brine (30 mL), dried over MgSO$_4$, filtered, and concentrated. The crude azide was dissolved in benzene (2.6 mL) and refluxed for 1 h. Benzyl alcohol (210 mg, 1.9 mmol) and p-toluenesulfonic acid (18 mg, 0.1 mmol) were added and the mixture was refluxed for 1 h. After cooling to rt, the reaction was quenched with water and extracted with CH$_2$Cl$_2$ (2×50 mL). The combined organic layer was washed with brine (50 mL), dried over MgSO$_4$, filtered, and concentrated. The crude was purified by silica gel column chromatography (33% EtOAc in hexane). The target amide (393 mg, 60% yield) was obtained. MS found: (M+H)$^+$=236.

(1g) The Cbz protected amine from reaction (1f) (3.8 g, 11.3 mmol), triethylamine (1.1 g, 11.3 mmol) and palladium hydrooxide on carbon (20 wt %, 400 mg, 0.56 mmol) were stirred in EtOAc (57 mL) under hydrogen (50 psi) at rt for 2 h. After filtration and concentration, the target amine was obtained (2.2 g, 96% yield). MS found: (M+H)$^+$=202.

(1h) To the solution of the amine from reaction (1g) (2.2 g, 11.3 mmol), 4-[(2-methyl-4-quinolinyl)methoxy]benzoic acid (3.49 g, 11.9 mmol) and diisopropylethylamine (3.7 g, 28.3 mmol) in DMF (57 mL) was added BOP reagent (6 g, 13.6 mmol) at 0° C. After stirring at rt for 3 h, the reaction was quenched with NH$_4$Cl (100 mL) at 0° C., extracted with EtOAc (300 mL×2), washed with brine (100 mL), dried over Na$_2$SO$_4$, filtered and concentrated. The crude (14 g) was purified by silica gel column chromatography (Gradient elution ethyl acetate/hexane, 1:1 to ethyl acetate) to give the target compound amide (5.4 g, 99% yield). MS found: (M+H)$^+$=477.

(1i) Preparation of hydroxylamine/sodium methoxide solution: hydroxylamine hydrochloride (2.4 g, 34.5 mmol) and MeOH (9 mL) were heated to 55° C. Sodium methoxide (25% wt in MeOH, 11.85 mL, 1.5 eq) was added, the mixture stirred at 55° C. for 5 minutes and cooled to room temperature then 0° C. Filtration afforded a clear solution assumed to be ca. 1.64 M. The solution is prepared and used fresh.

A solution of 1.64 M hydroxylamine solution (4 mL, 20 eq) was added to the amine from reaction (36a) (300 mg, 0.63 mmol) in MeOH (3 mL) then stirred for 1 h. The mixture was adjusted to pH 7 with 1 N hydrochloric acid (3 mL) providing a white precipitate. Filtration and drying provided the hydroxamic acid (220 mg, 73%, 2 steps). MS Found: (M+H)$^+$=478.

Example 2

(5R,7S,8R)-N-hydroxy-8-({4-[(2-methyl-4-quinolinyl)methoxy]benzoyl}amino)-1-oxaspiro[4.4]nonane-7-carboxamide trifluoroacetate (2a) The ketone from reaction (1c) (3 g, 10.9 mmol) in dichloromethane (129 mL) was treated with allyltrimethyl silane (20 eq) and cooled to 0° C. TiCl$_4$ (5 eq) was added dropwise over 30 min and the reaction allowed to warm to room temperature. The reaction was quenched by addition of ice and water and then extracted with dichloromethane, washed with water and brine, dried (MgSO$_4$), filtered and concentrated. Flash chromatography afforded the major diastereomer (943 mg, 29%) MS found: (M+H)$^+$=319 and the minor diastereomer (236 mg, 7%) MS found: (M+H)$^+$= 319.

(2b). The major diastereomer from reaction (2a) (100 mg, 0.31 mmole) in tetrahydrofuran (1 mL) at 0° C. was treated with a solution of diborane (1M, 2 eq) and stirred for 30 min. The solution was quenched with hydrogen peroxide/sodium hydroxide (1:1, 3 eq ea) and then extracted with ethyl acetate. The organic layers were washed with water and brine, dried (MgSO$_4$) filtered and concentrated. Flash chromatography yielded the desired alcohol (60 mg, 57%). MS found: (M+H)$^+$=337.

(2c) The alcohol from reaction (2b) (60 mg, 0.18 mmole) in dichloromethane (1 mL) was treated with triethyamine (2 eq) and methanesulfonylchloride (1.0 eq). The reaction was heated to reflux for 12 h and then partitioned between water and dichloromethane. The organic layer was washed with brine, dried (MgSO$_4$) and concentrated. Flash chromatography yielded the desired ester (34 mg, 60%). MS found: (M+H)$^+$=319.

(2d) Using procedures analogous to (1e)–(1g) and the ester from reaction (2c) (2.35 mg, 7.4 mmol) was converted to the desired acid, carbamate then amine (1.23 g, 85%, 3 Steps). MS found: (M+H)$^+$=200.

(2e) Using procedures analogous to (1h)–(1i) and the ester from reaction (2d) (1.2 g, 6.0 mmol) was converted to the desired hydroxamic acid (1.06 g, 30% yield, 2 steps). MS found: (M+H)$^+$=476.

Example 3

(5S,7S,8R)-N-hydroxy-8-({4-[(2-methyl-4-quinolinyl)methoxy]benzoyl}amino)-1-oxaspiro[4.4]nonane-7-carboxamide trifluoroacetate (3a) Using procedures analogous to (2b–e) the minor diastereomer from reaction (2a) (236 mg, 0.74 mmol) was converted to the desired hydroxamate (20 mg, 4% yield). MS found: (M+H)$^+$=476.

Example 4

(2S,3R)-N-hydroxy-3-({4-[(2-methyl-4-quinolinyl)methoxy]benzoyl}amino)-6,10-dioxaspiro[4.5]decane-2-carboxamide (4a) The ketal from reaction (1h) (47 mg, 0.1 mmol) in THF (0.4 mL) was treated with HCl (3N solution, 0.4 mL) at rt for 3 h. The reaction was quenched with saturated NaHCO3 to basic solution at 0° C. The mixture was extracted with ethyl acetate (20 mL×2), washed with brine (10 mL), dried over Na$_2$SO$_4$, filtered, and concentrated. Silica gel chromatography (dichloromethane/methanol, 20:1) provided the desired ketone (25 mg, 59% yield). MS found: (M+H)$^+$=231.

(4b) The ketone from reaction (4a) (50 mg, 0.11 mmol) in benzene was treated with 1,3-propylene glycol and heated under Dean-Stark conditions to afford the desired ester (49 mg, 86 mmol). MS found: (M+H)$^+$=491.

(4c) Using conditions analogous to (1i), the ester from reaction (4ba) was converted to the desired hydroxamate (7 mg, 14% yield). MS found: (M+H)$^+$=492.

Example 5

(7S,8R)-N-hydroxy-8-({4-[(2-methyl-4-quinolinyl)methoxy]benzoyl}amino)-1,4-dithiaspiro[4.4]nonane-7-carboxamide trifluoroacetate (5a) Using conditions analogous to (4b–c) the ketone from reaction (4a) (50 mg, 0.11 mmol) and 1,2-ethanedithiol were converted to the thiaketal and then the desired hydroxamic acid. MS found: (M+H)$^+$=510.

Example 6

(5R,7S,8R)-8-{[4-(2-butynyloxy)benzoyl]amino}-N-hydroxy-1-oxaspiro[4.4]nonane-7-carboxamide (6a) Using analogous procedures to (1h–i) the amine from reaction (1g) (14 mg, 0.07 mmol) and 4-(2-butynyloxy) benzoic acid (15 mg, 1.1 eq) were converted to the desired amide and then hydroxamate. MS found: (M+H)$^+$=373.

Example 7

(5R,7S,8R)-N-hydroxy-8-({4-[(2-methyl-1H-benzimidazol-1-yl)methyl]benzoyl}amino)-1-oxaspiro[4.4]nonane-7-carboxamide (7a) 2-methylbenzimidazole (0.58 g, 4.36 mmol), methyl 4-(bromomethyl)-benzoate (1 g, 1 eq), cesium carbonate (2.13 g, 1.5 eq) in dimethylsulfoxide (4.4 mL) were stirred at room temperature for ca. 12 h. The mixture was partitioned between ethyl acetate and water. The layers were separated and the organic layer washed with brine, dried (MgSO$_4$), filtered and concentrated. The crude material was purified on silica gel (ethyl acetate/methanol, 9:1) to give the desired ester as a white solid (0.77 g, 63%). MS found: (M+H)$^+$=281.

(7b) The ester from reaction (7a) (0.77 g, 2.75 mmol) in methanol (6.9 mL) was treated with lithium hydroxide (2N, 6.9 mL, 13.75 mmol) and stirred at rt for 2 h. The reaction was quenched with 1 N HCl (14 mL). The reaction was concentrated and extracted with ethyl acetate (2×), dried (MgSO$_4$), filtered and concentrated to give the desired acid (230 mg, 31%). MS found: (M+H)$^+$=267.

(7c) Using analogous procedures to (1h)–(1i) the amine from reaction (2d) (50 mg, 0.25 mmol) and the acid from reaction (7b) (80 mg, 1.2 eq) were converted to the desired amide then hydroxamate (67 mg, 48% 2 steps). MS found: (M+H)$^+$=449.

Example 8

(5R,7S,8R)-N-hydroxy-8-({4-[(2-isopropyl-1H-benzimidazol-1-yl)methyl]benzoyl}amino)-1-oxaspiro[4.4]nonane-7-carboxamide (8a) Using analogous procedures to (7a)–(7b) 2-isopropylbenzimidazole (698 mg, 4.36 mmol) and methyl 4-(bromomethyl)-benzoate (1 eq) were converted to the desired acid (446 mg, 28% yield, 2 steps). MS found: (M+H)⁺=295.

(8b) Using analogous procedures to (1h)–(1i) the amine from reaction (2d) (54 mg, 0.27 mmol) and the acid from reaction (8a) (95 mg, 1.2 eq) were converted to the desired amide then hydroxamate (50 mg, 50% 2 steps). MS found: (M+H)⁺=477.

Example 9

(5R,7S,8R)-N-hydroxy-8-[(4-{[2-(trifluoromethyl)-1H-benzimidazol-1-yl]methyl}benzoyl)amino]-1-oxaspiro[4.4]nonane-7-carboxamide (9a) Using analogous procedures to (7a)–(7b), 2-trifluormethylbenzimidazole (685 mg, 2.99 mmol) and methyl 4-(bromomethyl)-benzoate (1 eq) were converted to the desired acid (1 g, 99% yield, 2 steps). MS found: (M+H)⁺=321.

(9b) Using analogous procedures to (1h)–(1i) the amine from reaction (2d) (49 mg, 0.25 mmol) and the acid from reaction (9a) (86 mg, 1.1 eq) were converted to the desired amide then hydroxamate (47 mg, 38% 2 steps). MS found: (M+H)⁺=503.

Example 10

(5R,7S,8R)-8-({4-[(2-tert-butyl-1H-benzimidazol-1-yl)methyl]benzoyl}amino)-N-hydroxy-1-oxaspiro[4.4]nonane-7-carboxamide (10a) Using analogous procedures to (7a)–(7b), 2-t-butylbenzimidazole (1.6 g, 9.3 mmol) and methyl 4-(bromomethyl) benzoate (1 eq) were converted to the desired acid (1.9 g, 66% yield, 2 steps). MS found: (M+H)⁺=309.

(10b) Using analogous procedures to (1h)–(1i) the amine from reaction (2d) (64 mg, 0.32 mmol) and the acid from reaction (10a) (120 mg, 1.2 eq) were converted to the desired amide then hydroxamate (93 mg, 40% 2 steps). MS found: (M+H)⁺=492.

Example 11

(5R,7S,8R)-N-hydroxy-8-({4-[(2-methyl-1H-indol-3-yl)methyl]benzoyl}amino)-1-oxaspiro[4.4]nonane-7-carboxamide (11a) To a solution of trifluoroacetic acid (TFA) (1.16 mL, 15 mmol) in CH₂Cl₂ and triethylsilane (4.79 mL, 30 mmol) was added a solution of methyl 4-formylbenzoate (1.81 g, 11 mmol) and 2-methylindole (1.31 g, 10 mmol). The reaction was stirred 10 min at 0° C. and then quenched by adding the reaction solution to NaOH. Additional NaOH was added to get the pH to 8. The aqueous layer was extracted with EtOAc (1×100 mL) to obtain the crude compound. The crude was purified by silica gel chromatography (hexanes to 25% EtOAc/hexanes) to yield the desired ester (2.18 g, 78%). MS found: (M+Na)⁺=302.

(11b) To a suspension of (11a) (1.79 mmol, 500 mg) in MeOH (5 mL) was added LiOH (0.9 mL, 1.79 mmol, 2M solution). The reaction was stirred for 16 h and then quenched to pH 7 with HCl (1N). The reaction mixture was filtered to afford the desired acid (475 mg, 100%). MS found: (M+H)⁺=266.

(11c) Using analogous procedures to (1h)–(1i) the amine from reaction (2d) (42 mg, 0.21 mmol) and the acid from reaction (11b) (86 mg, 1.1 eq) were converted to the desired amide then hydroxamate (3 mg, 3% 2 steps). MS found: (M+H)⁺=448.

Example 12

(5R,7S,8R)-8-[(4-{[2-(difluoromethyl)-1H-benzimidazol-1-yl]methyl}benzoyl)amino]-N-hydroxy-1-oxaspiro[4.4]nonane-7-carboxamide (12a) Using analogous procedures to (7a)–(7b), 2-(difluoromethyl)-benzimidazole (2.41 g, 11 mmol) was converted to the desired acid (1.47 mg, 49% yield,2 steps). MS found: (M+H)⁺=303.

(12b) Using analogous procedures to (1h)–(1i) the amine from reaction (2d) (48 mg, 0.24 mmol) and the acid from reaction (11b) (81 mg, 1.1 eq) were converted to the desired amide then hydroxamate (35 mg, 28% 2 steps). MS found: (M+H)⁺=485.

Example 13

(5R,7S,8R)-8-({4-[(2-cyclopropyl-1H-benzimidazol-1-yl)methyl]benzoyl}amino)-N-hydroxy-1-oxaspiro[4.4]nonane-7-carboxamide (13a) 2-cyclopropanecarboxylic acid (4 g, 52 mmol) was treated with phenylenediamine bis-hydrochloride (1 eq) and polyphosphoric acid (52 mL) and heated to 160° C. for 6 h. The reaction was cooled to 0° C. and diluted with water, then basified with NaOH (50% aqueous) until pH>10. The solution was extracted with ethyl acetate, dried (MgSO₄), filtered and concentrated, purified by flash chromatography (100% ethyl acetate) giving 2-cyclopropylbenzimidazole (1.1 g, 13%). MS found: (M+H)⁺=159.

(13b) Using analogous procedures to (7a)–(7b), 2-cyclopropylbenzimidazole (0.47 g, 3.0 mmol) was converted to the desired acid (375 mg, 43% yield, 2 steps). MS found: (M+H)⁺=293.

(13c) Using analogous procedures to (1h)–(1i) the amine from reaction (2d) (52 mg, 0.26 mmol) and the acid from reaction (13b) (83 mg, 1.1 eq) were converted to the desired amide then hydroxamate (17 mg, 13% 2 steps). MS found: (M+H)⁺=475.

Example 14

(5R,7S,8R)-8-({4-[(2-cyclobutyl-1H-benzimidazol-1-yl)methyl]benzoyl}amino)-N-hydroxy-1-oxaspiro[4.4]nonane-7-carboxamide (14a) Using analogous procedures to (13a) 2-cyclobutanecarboxylic acid (5.2 g, 52 mmol) was converted to the desired benzimidazole (2.4 g, 27% yield).). MS found: (M+H)⁺=173.

(14b) Using analogous procedures to (7a)–(7b), 2-cyclobutylbenzimidazole (1.0 g, 5.8 mmol) was converted to the desired acid (640 mg, 36% yield, 2 steps). MS found: (M+H)⁺=307.

(14c) Using analogous procedures to (1h)–(1i) the amine from reaction (2d) (87 mg, 0.43 mmol) and the acid from reaction (14b) (135 mg, 1.0 eq) were converted to the desired amide then hydroxamate (50 mg, 23% yield, 2 steps). MS found: (M+H)⁺=490.

Example 15

(5R,7S,8R)-N-hydroxy-8-({4-[(2-isopropyl-1H-imidazol-1-yl)methyl]benzoyl}amino)-1-oxaspiro[4.4]nonane-7-carboxamide (15a) Using analogous procedures to (7a)–(7b), (1h)–(1i) 2-isopropylimidazole (1.1 g, 10 mmol) was converted to the desired hydroxamate acid (12 mg, 1% yield, 4 steps). MS found: $(M+H)^+$=427.

Example 16

(5R,7S,8R)-N-hydroxy-8-({4-[(2-methyl-1H-indol-1-yl)methyl]benzoyl}amino)-1-oxaspiro[4.4]nonane-7-carboxamide (16a) To a solution of 2-methylindole (7.60 mmol, 1.00 g) was added 18-crown-6 (60 mg, 0.06 mmol) and subsequently powdered KOH (416 mg, 7.60 mmol) and methyl 4-(bromomethyl)benzoate (1 eq). The reaction was heated to 100° C. for 2 h, and was added additional KOH (416 mg, 7.60 mmol). The reaction was stirred for another 1 h. The reaction was cooled and then quenched with 1N HCl and extracted with EtOAc (2×100 mL). The organic layers were collected, dried and concentrated in vacuo. The crude was flashed to yield the desired acid (798 mg, 40%). MS found: $(M+H)^+$=274.

(16b) Using analogous procedures to (1h)–(1i) the amine from reaction (2d) (39 mg, 0.2 mmol) and the acid from reaction (16a) (53 mg, 1 eq) were converted to the desired amide then hydroxamate (6 mg, 7%, 2 steps). MS found: $(M+H)^+$=448.

Example 17

(5R,7S,8R)-N-hydroxy-8-[(4-{[2-(1-methylcyclopropyl)-1H-benzimidazol-1-yl]methyl}benzoyl)amino]-1-oxaspiro[4.4]nonane-7-carboxamide (17a) Using procedures similar to (1h), phenylenediamine bis-hydrochloride (6.9 g, 38 mmol) and 1-methyl-cyclopropanecarboxylic acid (3.8 g, 1 eq) were converted to the desired amide (4.0 g, 55%). MS found: $(M+H)^+$=191.

(17b) The amide from reaction (17a), (1.9 g, 10 mmol) in acetic acid (30 mL) was heated at 60° C. for 3 h. The mixture was concentrated, dissolved in ethyl acetate (20 mL), washed with saturated aqueous $Na_2CO_3$, saturated aqueous $NaHCO_3$, water, brine (10 mL each), dried ($MgSO_4$), filtered and concentrated to give the desired benzimidazole (1.7 g, 98%). MS found: $(M+H)^+$=173.

(17c) Using procedures analogous to (7a)–(7b), the product from reaction (17b) (1 g, 5.8 mmol) was converted to the desired acid (1.25 g, 70%, 2 steps). MS found: $(M+H)^+$=307.

(17d) Using procedures analogous to (1h)–(1i), the product from reaction (17c) (56 mg, 0.18 mmol) and the amine from reaction (2d) (53 mg, 1 eq) were converted to the desired hydroxamic acid (33 mg, 32%, 2 Steps). MS found: $(M+H)^+$=489.

Example 18

(5R,7S,8R)-8-[(4-{[2-(fluoromethyl)-1H-benzimidazol-1-yl]methyl}benzoyl)amino]-N-hydroxy-1-oxaspiro[4.4]nonane-7-carboxamide (18a) Using procedures analogous to (17a)–(17c), fluoroacetic acid (2 g, 26 mmol) was converted to the desired acid (1.4 g, 12% yield, 3 steps). MS found: $(M+H)^+$=285.

(18b) Using procedures analogous to (1h)–(1i), the product from reaction (18a) (57 mg, 2 mmol) and the amine from reaction (2d) (40, 1 eq) were converted to the desired hydroxamic acid (34 mg, 29%, 2 Steps). MS found: $(M+H)^+$=467.

Example 19

(5R,7S,8R)-8-[(4-{[2-(1-fluoro-1-methylethyl)-1H-benzimidazol-1-yl]methyl}benzoyl)amino]-N-hydroxy-1-oxaspiro[4.4]nonane-7-carboxamide (19a) Ethyl-2-hydroxyisobutyrate (6 g, 45 mmol) in dichloromethane (60 mL) was treated with (diethylamino) sulfur trifluoride (DAST) (1.5 eq) at −78° C., then warmed to rt and stirred for 2 h. The mixture was quenched with saturated $NaHCO_3$ (aq) and extracted with ethyl acetate, washed with water, brine, dried ($MgSO_4$) filtered and concentrated to give the desired ester (2.5 g, 41%). MS found: $(M+CH_3CN+H)^+$=176.

(19b) The solution of the ester for reaction (19a) (2.00 g, 14.9 mmol) in methanol (100 mL) was treated with potassium hydroxide (3.34 g, 4.0 eq) at rt and stirred for 24 hrs. Then the mixture was adjusted pH to 2–3 with 1N HCl and concentrated in vacuo to remove the methanol. The aqueous residue was extracted with ethyl acetate (100 mL, 3 times). The combined organic layers was washed with water (20 mL), brine (20 mL), dried ($MgSO_4$) and concentrated in vacuo to provide the desired acid (1.50 g, 94.8%) and taken on without further purification.

(19c) Using procedures analogous to (17a)–(17c) the acid from reaction (19b) (400 mg, 3.8 mmol) was converted to the desired acid (160 mg, 14%, 3 steps). MS found: $(M+H)^+$=313.

(19d) Using procedures analogous to (1h)–(1i), the product from reaction (19c) (47 mg, 0.15 mmol) and the amine from reaction (2d) (30 mg, 1 eq) were converted to the desired hydroxamic acid (30 mg, 33%, 2 Steps). MS found: $(M+H)^+$=495.

Example 20

(5R,7S,8R)-N-hydroxy-8-{[4-(1H-indol-3-ylmethyl)benzoyl]amino}-1-oxaspiro[4.4]nonane-7-carboxamide (20a) Using procedures analogous to (11a)–(11b), (1h)–(1i) the amine from reaction (2d) (30 mg, 0.15 mmol) and indole (1 eq) were converted to the desired amide then hydroxamate (15 mg, 23%). MS found: $(M+H)^+$=435.

Example 21

5R,7S,8R)-8-[(4-{[2-(1,1-difluoroethyl)-1H-benzimidazol-1-yl]methyl}benzoyl)amino]-N-hydroxy-1-oxaspiro[4.4]nonane-7-carboxamide (21a) Using analogous procedure to (19a) ethyl pyruvate (5.00 g, 43.1 mmol) was converted the desired ester as crude material (3.00 g) which was directly converted to the next step.

(21b) Using analogous procedure to (19b)–(19c) the ester from reaction (21a) (3.00 g) was converted to the desired acid (480 mg, 10.2% 6 steps). MS found: $(M+H)^+$=317.

(21c) Using procedures analogous to (1h)–(1i), the product from reaction (21b) (77.5 mg, 0.250 mmol) and the amine from reaction (2d) (50 mg, 1.0 eq) were converted to the desired hydroxamic acid (30.0 mg, 24% 2 steps). MS found: $(M+H)^+$=499.

Example 22

(5R,7S,8R)-8-({4-[(2,3-dimethyl-1H-indol-1-yl)methyl]benzoyl}amino)-N-hydroxy-1-oxaspiro[4.4]nonane-7-carboxamide (22a) To a solution of 2,3-dimethyl indole (1.0 g, 6.89 mmol) in DMF (30 mL) was added 18-crown-6 (56 mg, 0.21 mmol), KOH (386 mg, 6.89 mmol) and methyl 4-(bromomethyl)benzoate (1.58 g, 6.89 mmol). The reaction after flash chromatography afforded the desired ester (720 mg, 36%). MS found: $(M−Me+H)^+$=279.

(22b) Using a procedure analogous to (7b), the product from (22a) (2.45 mmol, 720 mg) was reacted to afford the acid (347 mg, 48%). MS found: (M+H)$^+$=280.

(22c) Using analogous procedures to (1h)–(1i) the amine from reaction (2d) (54 mg, 0.27 mmol) and the acid from reaction (22b) (40 mg, 1.0 eq) were converted to the desired amide then hydroxamate (15 mg, 23% 2 steps). MS found: (M+H)$^+$=462.

Example 23

(5R,7S,8R)-8-({4-[(2-ethyl-1H-indol-3-yl)methyl] benzoyl}amino)-N-hydroxy-1-oxaspiro[4.4]nonane-7-carboxamide (23a) Using procedures analogous to (11a)–(11c), 2-ethylindole (synthesized using the method of: Smith, A. B., III; Visnick, M.; Haseltine, J. N.; Sprengeler, P. A. Tetrahedron (1986), 42(11), 2957–69) (1.0 g, 6.9 mmol) was converted to the desired hydroxamate (40 mg, 11% yield, 4 steps). MS found: (M+H)$^+$=462.

Example 24

(5R,7S,8R)-N-hydroxy-8-[(4-{[2-(trifluoromethyl)-1H-indol-1-yl]methyl}benzoyl)amino]-1-oxaspiro [4.4]nonane-7-carboxamide (24a) Using procedures analogous to (16a)–(16b), 2-trifluoromethylindole ((synthesized using the method of: Smith, A. B., III; Visnick, M.; Haseltine, J. N.; Sprengeler, P. A. Tetrahedron (1986), 42(11), 2957–69) (98 mg, 6.9 mmol) was converted to the desired hydroxamate (10 mg, 7% yield, 4 steps). MS found: (M+H)$^+$=501.

Example 33

(5R,7S,8R)-8-{[4-(1,1-dioxido-3,4-dihydro-2H-1-benzothiopyran-4-yl)benzoyl]amino}-N-hydroxy-1-oxaspiro[4.4]nonane-7-carboxamide (33a) Trifluoromethanesulfonic anhydride (2.2 mL, 13.4 mmol) was added dropwise to a stirring solution of thiochroman-4-one (2.0 g, 12.2 mmol), 2,6-di-t-butyl-4-methyl pyridine (2.63 g, 12.8 mmol) in dichloromethane (100 mL), under nitrogen atmosphere. The reaction was heated to reflux for 2 h, allowed to cool to room temperature and was concentrated in vacuo to give a semi-solid residue. This was treated with hexane and the solids were filtered off. The filtrate was concentrated to give 2H-1-benzothiopyran-4-yltrifluoromethyl sulfone (1.84 g, 51%) as a solid. MS found: (M+H)$^+$=297.

(33b) 2H-1-benzothiopyran-4-yl trifluoromethyl sulfone from reaction 33a (1.83 g, 6.17 mmol) and 4-(methoxy carbonylphenyl)boronic acid (1.11 g, 6.17 mmol) were dissolved in ethanol (15 mL) and toluene (30 mL) under nitrogen at room temperature. Then lithium chloride (0.52 g, 12.35 mmol) and 2.65 M potassium carbonate (4.66 mL, 12.35 mmol) were added. Nitrogen was bubbled through the reaction for 15 minutes tetrakis(triphenylphosphine)-palladium(0) (0.35 g, 0.31 mmol) was added. The reaction was heated to reflux for 2 h, allowed to cool then partitioned between ethyl acetate and water. The organic layer was washed with water, brine, dried over magnesium sulfate, and was concentrated. The product was purified by chromatography on silica gel eluting with ethyl acetate:hexane (15:85, v:v) to give methyl 4-(2H-1-benzothiopyran-4-yl)benzoate (1.75 g, 67%) as a solid.

(33c) Methyl 4-(2H-1-benzothiopyran-4-yl)benzoate from reaction 33b (0.77 g, 2.75 mmol) was dissolved in methanol (30 mL) cooled to 0° C. and Oxone® (6.76 g, 11.1 mmol) in water (7 mL) was added. The reaction was stirred for 1 h at 0° C. and then allowed to warm to room temperature and stir for another hour. The reaction was diluted with water, pH adjusted to pH=8 with 1 N sodium hydroxide. This was extracted with ethyl acetate. The combined organic layers were washed with water, brine, dried over magnesium sulfate and concentrated to give methyl 4-(1,1-dioxido-2H-1-benzothiopyran-4-yl)benzoate (0.784 g, 91%) as a solid.

(33d) Methyl 4-(1,1-dioxido-2H-1-benzothiopyran-4-yl) benzoate from reaction 33c (0.64 g, 2.13 mmol) was dissolved in methanol (30 mL), degassed with nitrogen, 5% Pd/C was added and the reaction was charged to 55 PSI hydrogen. The reaction was shaken for 6 h. The catalyst was removed over Celite and the filtrate was concentrated to give methyl 4-(1,1-dioxido-3,4-dihydro-2H-1-benzothiopyran-4-yl)benzoate (0.49 g, 73%) as a solid.

(33e) Lithium hydroxide hydrate (0.195 g, 4.65 mmol) dissolved in water (1 mL) was added to a solution of methyl 4-(1,1-dioxido-3,4-dihydro-2H-1-benzothiopyran-4-yl) benzoate from reaction 33d (0.49 gm, 1.55 mmol) in THF (5 mL) and methanol (1 mL) under nitrogen atmosphere at room temperature. The reaction was stirred over night, concentrated then partitioned between 1 N HCl and ethyl acetate. The organic layer was washed with water, brine, dried over magnesium sulfate and concentrated to give 4-(1,1-dioxido-3,4-dihydro-2H-1-benzothiopyran-4-yl) benzoic acid (0.46 g, 98%) as an solid. MS found: (M–H)$^+$=301.

(33f) 4-(1,1-dioxido-3,4-dihydro-2H-1-benzothiopyran-4-yl)benzoic acid from reaction 33e (0.05 g, 0.165 mmol), the amine from reaction (2d) (0.030 g, 0.15 mmol), BOP (0.1 g, 0.22 mmol) and DIEA (0.058 g, 0.45 mmol) were combined in DMF (2 mL), under a nitrogen atmosphere at room temperature. The reaction was stirred for 48 h, partitioned between ethyl acetate and water. The combined organic layers were washed with water, brine, dried over magnesium sulfate and concentrated to give methyl (5R,7S, 8R)-8-{[4-(1,1-dioxido-3,4-dihydro-2H-1-benzothiopyran-4-yl)benzoyl]amino}-1-oxaspiro[4.4]nonane-7-carboxylate (0.07 g, 90%) as a tan solid.

(33g) Methyl (5R,7S,8R)-8-{[4-(1,1-dioxido-3,4-dihydro-2H-1-benzothiopyran-4-yl)benzoyl]amino}-1-oxaspiro[4.4]nonane-7-carboxylate from reaction 33f (0.165 mmol) was dissolved in a solution of hydroxylamine hydrochloride, methanol and sodium methoxide, (2 mL) under nitrogen atmosphere at room temperature. The reaction was stirred for 1 h, made neutral with TFA, concentrated and purified by HPLC on a C-18 column eluting with an acetonitrile:water:TFA gradient, to give the title compound (0.03 g, 37%) as a white solid. MS found: (M+H)$^+$=485, (2M+H)$^+$=969.

Example 34

(5R,7S,8R)-8-{[4-(3,4-dihydro-2H-chromen-4-yl) benzoyl]amino}-N-hydroxy-1-oxaspiro[4.4]nonane-7-carboxamide (34a) Trifluoromethanesulfonic anhydride (1.2 mL, 7.4 mmol)was added drop wise to a stirring solution of chroman-4-one (1.0 g, 6.7 mmol), 2,6-di-t-butyl-4-methyl pyridine (1.59 g, 7.7 mmol) in dichloromethane (40 mL), under nitrogen atmosphere. The reaction was heated to reflux for 2 h, allowed to cool to room temperature and was concentrated in vacuo to give a semi solid residue. This was treated with hexane and the solids were filtered off. The filtrate was concentrated to give 4-[(trifluoromethyl)sulfonyl]-2H-chromene (1.78 g, 94%) as an orange oil.

(34b) 4-[(trifluoromethyl)sulfonyl]-2H-chromene from reaction 34a (1.78 g, 6.47 mmol) and 4-(methoxycarbonylphenyl) boronic acid (1.0 g, 5.6 mmol) were dissolved in ethanol (15 mL) and toluene (30 mL) under nitrogen at room temperature. Then lithium chloride (0.52 g, 12.35 mmol) and 2.65 M potassium carbonate (4.2 mL, 11.0 mmol) were added. Nitrogen was bubbled through the reaction for 15 minutes before the tetrakis(triphenylphosphine)palladium(0) (0.35 g, 0.31 mmol) was added. The reaction was heated to reflux for 3 h, allowed to cool then partitioned between ethyl acetate and water. The organic layer was washed with water, brine, dried over magnesium sulfate, and was concentrated. The product was purified by chromatography on silica gel eluting with ethyl ether:hexane (20:80, v:v) to give methyl 4-(2H-chromen-4-yl)benzoate (1.53 g, 99%) as a yellow solid.

(34c) Lithium hydroxide hydrate (0.80 g, 19.0 mmol) dissolved in water (20 mL) was added to a solution of methyl 4-(2H-chromen-4-yl)benzoate from reaction 34b (1.5 gm, 5.7 mmol) in THF (20 mL) and methanol (20 mL) under nitrogen atmosphere at room temperature. The reaction was heated to 50° C. for 2 h, allowed to cool, concentrated then partitioned between 1 N HCl and ethyl acetate. The organic layer was washed with water, brine, dried over magnesium sulfate and concentrated to give 4-(2H-chromen-4-yl)benzoic acid (1.29 g, 89%) as a tan solid. MS found: $(M-H)^+=251$.

(34d) Thionyl chloride (2 mL) was added to a suspension of 4-(2H-chromen-4-yl)benzoic acid from reaction 34c (0.415 g, 1.6 mmol) in dichloromethane (10 mL) at room temperature. The reaction was stirred for 4 h, concentrated in vacuo to give 4-(2H-chromen-4-yl)benzoyl chloride (0.445 g, 99%) as a yellow solid.

(34e) Water saturated sodium bicarbonate (10 mL) was added to a solution of 4-(2H-chromen-4-yl)benzoyl chloride from reaction 34d (0.15 g, 0.55 mmol) and the amine from reaction (2d) (0.120 g, 0.60 mmol) in benzene (10 mL). The reaction was stirred vigorously for 3 h, then partitioned between ethyl acetate and 1 N HCl. The combined organic layer was washed with water, brine, dried over magnesium sulfate and concentrated to give methyl (5R,7S,8R)-8-{[4-(2H-chromen-4-yl)benzoyl]amino}-1-oxaspiro[4.4]nonane-7-carboxylate (0.23 g, 96%) as a yellow oil. MS found: $(M+H)^+=434$.

(34f) Methyl (5R,7S,8R)-8-{[4-(2H-chromen-4-yl)benzoyl]amino}-1-oxaspiro[4.4]nonane-7-carboxylate from reaction 34e (0.12 g, 0.29 mmol) was dissolved in methanol (30 mL), degassed with nitrogen, 5% Pd/C was added and the reaction was charged to 55 psi hydrogen. The reaction was shaken for 6 h. The catalyst was removed over Celite and the filtrate was concentrated to give methyl (5R,7S,8R)-8-{[4-(3,4-dihydro-2H-chromen-4-yl)benzoyl]amino}-1-oxaspiro[4.4]nonane-7-carboxylate (0.10 g, 80%) as a clear oil.

(34g) Methyl (5R,7S,8R)-8-{[4-(3,4-dihydro-2H-chromen-4-yl)benzoyl]amino}-1-oxaspiro[4.4]nonane-7-carboxylate from reaction 34f (0.095 g, 0.22 mmol) was dissolved in a solution of hydroxylamine hydrochloride, methanol and sodium methoxide, (2 mL) under nitrogen atmosphere at room temperature. The reaction was stirred for 1 h, made neutral with TFA, concentrated and purified by HPLC on a C-18 column eluting with an acetonitrile:water:TFA gradient, to give the title compound (0.032 g, 34%) as a white solid. MS found: $(M+H)^+=435$.

Example 35

(5R,7S,8R)-8-{[4-(2H-chromen-4-yl)benzoyl]amino}-N-hydroxy-1-oxaspiro[4.4]nonane-7-carboxamide (35a) (5R,7S,8R)-8-{[4-(2H-chromen-4-yl)benzoyl]amino}-1-oxaspiro[4.4]nonane-7-carboxylate from reaction (34e) (0.10 g, 0.23 mmol) was dissolved in a solution of hydroxylamine hydrochloride, methanol and sodium methoxide, (2 mL) under nitrogen atmosphere at room temperature. The reaction was stirred for 1 h, made neutral with TFA, concentrated and purified by HPLC on a C-18 column eluting with an acetonitrile:water:TFA gradient, to give the title compound (0.032 g, 32%) as a white solid. MS found: $(M-H)^+=433$.

Example 41

N-{(5R,7R,8S)-8-[(hydroxyamino)carbonyl]-1-oxaspiro[4.4]non-7-yl}-2-[(2-isopropyl-1H-benzimidazol-1-yl)methyl]-1,3-thiazole-4-carboxamide (41a) 2-Isopropylbenzimidizole (5.0 g, 31.2 mmol) was added portionwise to a stirred suspension of sodium hydride (1.25 g, 60% in mineral oil, 31.2 mmol) in DMF. After 30 min at room temperature 2-chloroacetamide (4.37 g, 46.9 mmol) was added and the solution heated to 50° C. for 18 h. The reaction was quenched with saturated $NH_4Cl$ then concentrated to dryness. A mixture of water/chloroform (1/1, 100 mL) was added and mixture was stirred vigorously for 15 min. The resulting white solid 41a was collected and dried under vacuum (2.92 g, 43%). MS Found: $(M+H)^+=218$.

(41b) Lawesson's Reagent (5.23 g, 12.9 mmol) and 41a (2.81 g, 12.9 mmol) were refluxed in toluene for 2 h. The solution was cooled to room temperature and 1N NaOH (75 mL) was added to the mixture then stirred for 30 min. The basic solution was extracted with EtOAc (3x) then the combined organic fractions were washed with brine. After drying over $MgSO_4$ the solution was filtered and concentrated to dryness. The residue was purified by flash chromatography to give 41b as a white solid (1.74 g, 59%). MS Found: $(M+H)^+=234$.

(41c) Sodium methoxide (28.5 g, 0.525 mol) was added, portion wise to a cooled solution (0° C.) of methyl chloroacetate (54.4 g, 0.50 mol) and methyl formate (31.5 g, 0.525 mol) in toluene maintaining the temperature of the reaction below 5° C. The solution was allowed to stir at 0° C. for 4 h then warm to room temperature. Water (200 mL) was added and the organic layer was separated. The aqueous layer was washed with ether then neutralized with 1N HCl. The aqueous layer was extracted with ether (3x) then the combined organic fractions were dried over $MgSO_4$ and concentrated in vacuo to give 41c a pale yellow oil (30.06 g, 44%) that was carried forward without further purification.

(41d) A solution of 41b (1.74 g, 7.45 mmol) and 41c (5.08 g, 37.3 mmol) were refluxed in ethanol overnight. The mixture was concentrated to dryness and the residue partitioned between EtOAc and $NaHCO_3$. The aqueous layer was extracted with EtOAc (3x) and the combined organic fractions were washed in succession with water, $NaHCO_3$, and brine. After drying over $MgSO_4$, filtration, and concentration to dryness the residue was purified by flash chromatography to give 41d as a yellow oil (1.36 g, 58%). MS Found: $(M+H)^+=316$.

(41e) Lithium hydroxide monohydrate (0.30 g, 6.47 mmol) was dissolved in water (8 mL) then added to 41d (1.36 g, 4.31 mmol) in THF (16 mL). The solution was stirred overnight and water (80 mL) was added. The aqueous phase was washed with ether (2x) then neutralized by the addition of 1N HCl. The resulting solid was filtered and dried under vacuum to provide 41e as a light yellow solid (1.31 g, 100%). MS Found: $(M+H)^+=302$.

(41f) DIEA (0.252 g, 1.96 mmol) was added to the amine from reaction 2d (0.078 g, 0.39 mmol), 41e (0.153 g, 0.51 mmol) and BOP reagent (0.19 g, 0.43 mmol) in DMF at room temperature. After stirring overnight the solution was concentrated in vacuo, then diluted with EtOAc. The solution was washed with water, $NaHCO_3$, and brine then dried over $MgSO_4$. After filtration and removal of the solvent the residue was purified by flash chromatography to give 41f as a clear oil (0.081 g, 43%). MS Found: $(M+H)^+=483$.

(41g) Sodium methoxide (11.9 mL, 25% in methanol, 52.0 mmol) was added in a slow stream to hydroxylamine hydrochloride (2.40 g, 34.5 mmol) in methanol (9 mL) at 55° C. The mixture was stirred for 5 min then cooled to room temperature. The sodium chloride was filtered to give a 1.64 M solution of basic hydroxyl amine. An aliquot (2.05 mL, 3.36 mmol) was added in one portion to 41f (81 mg, 0.17 mmol) and stirred at room temperature for 20 min. The reaction was quenched with 1N HCl and solvent was removed in vacuo. The residue was purified by reverse phase HPLC (C-18, acetonitrile/water) to provide example 41 as a white powder (27 mg, 33%) after lyophilization. MS Found: $(M+H)^+=484$.

Example 42

(5R,7S,8R)-8-({4-[(3,5-dimethyl-1H-pyrazol-4-yl) methyl]benzoyl}amino)-N-hydroxy-1-oxaspiro[4.4] nonane-7-carboxamide (42a) Methyl 4-formylbenzoate (2.00 g, 12.2 mmol), acetyl acetone (1.16 g, 11.6 mmol), piperidine (48 μL, 0.48 mmol), and acetic acid (0.14 mL, 2.44 mmol) were combined in toluene (60 mL) and heated to reflux with a Dean Stark trap attached for water removal. The reaction was complete in 2.5 h, the Dean Stark trap was removed and the mixture allowed to cool to room temperature. Dilution with ethyl acetate (120 mL) was followed by washing with water, 10% citric acid, $NaHCO_3$ (2x), and brine. After drying over $MgSO_4$, the solution was filtered and evaporated, then the residue was purified by flash chromatography to provide 42a as a yellow oil (2.43 g, 85%). MS Found: $(M+H)^+=247$.

(42b) Methanol (60 mL) was added slowly to 42a (2.42 g, 9.83 mmol) and palladium on carbon (10%, 0.5 g) under a steady stream of nitrogen. A hydrogen balloon was attached via a three way stopcock and the atmosphere above the reaction was removed and replaced with hydrogen three times. After 1 h no starting material was detectable by TLC and the hydrogen was removed and replaced with nitrogen. The catalyst was filtered and the solvent removed by evaporation in vacuo. The residue was purified by flash chromatography to provide 42b (1.91 g, 78%) as a clear oil. MS Found: $(M+H)^+=249$.

(42c) Hydrazine hydrate (0.14 g, 2.76 mmol) and 42b (0.62 g, 2.51 mmol) were combined in methanol (15 mL) and heated to reflux for 1.5 h. The reaction was cooled to room temperature and the solvent removed in vacuo. The residue was purified by flash chromatography to provide 42c as a waxy solid (585 mg, 95%). MS Found: $(M+H)^+=245$.

(42d) Sodium hydroxide (0.33 g, 8.33 mmol) was dissolved in water (5 mL) then added to 42c (585 mg, 2.39 mmol) in methanol/THF (1/1, 10 mL). The solution was stirred overnight and solvent was removed in vacuo. The residue was taken up in water (20 mL) and the aqueous phase was washed with ether (2x) then neutralized by the addition of 1N HCl (8.3 mL). The resulting solid was filtered and dried under vacuum to provide the desired acid as a white solid (288 mg, 88%). MS Found: $(M+H)^+=231$.

(42e) N-Methylmorpholine (195 mg, 1.93 mmol) was added to the amine from reaction 2d (77 mg, 0.39 mmol), the acid from (42d) (89 mg, 0.39 mmol) and BOP reagent (188 mg, 0.430 mmol) in DMF at room temperature. After stirring overnight the solution was concentrated in vacuo, then diluted with EtAOc (25 mL). The solution was washed with water, $NaHCO_3$ (2x), and brine then dried over $MgSO_4$. After filtration and removal of the solvent the residue was purified by flash chromatography to give the desired ester as a clear oil (109 mg, 69%). MS Found: $(M+H)^+=483$.

(42f) Sodium methoxide (11.9 mL, 25% in methanol, 52.0 mmol) was added in a slow stream to hydroxylamine hydrochloride (2.40 g, 34.5 mmol) in methanol (9 mL) at 55° C. The mixture was stirred for 5 min then cooled to room temperature. The sodium chloride was filtered to give a 1.64 M solution of basic hydroxyl amine. An aliquot (3 mL, 4.92 mmol) was added in one portion to 42e (109 mg, 0.26 mmol) and stirred at room temperature for 30 min. The pH was adjusted to 6 with 1N HCl and the mixture was stirred vigorously for 20 min. The resulting solid was filtered then dried under vacuum to give the desired hydroxamate as a white solid (73 mg, 67%). MS Found: $(M+H)^+=413$.

Example 43

(5R,7S,8R)-N-hydroxy-8-({4-[(1,3,5-trimethyl-1H-pyrazol-4-yl)methyl]benzoyl}amino)-1-oxaspiro [4.4]nonane-7-carboxamide

(43) Example 43 was prepared in an analogous manner to example 42 substituting N-methyl hydrazine for hydrazine hydrate in step 42c. Example 43 was isolated as a white solid (79 mg, 80%). MS Found: $(M+H)^+=427$.

Example 51

(5R,7S,8R)-8-({4-[(1,1-dioxido-2,3-dihydro-4H-1,4-benzothiazin-4-yl)methyl]benzoyl}amino)-N-hydroxy-1-oxaspiro[4.4]nonane-7-carboxamide (51a) $K_2CO_3$ (4.4 g, 31.9 mmol) and 1,2-dibromoethane (0.69 mL, 8.0 mmol) were added to a solution of 2-aminothiophenol (1.0 g, 8.0 mmol) in 20 mL of acetone at room temperature. The reaction mixture was stirred overnight. The insoluble material was filtered off and the solvent was removed under reduced pressure. The residue was purified on silica gel column to provide 3,4-dihydro-2H-1,4-benzothiazine (0.8 g, 66%). MS $(ES^+)$: 152 (M+1).

(51b) $K_2CO_3$ (5.2 g, 37.7 mmol) and methyl 4-bromomethylbenzoate (2.8 g, 12.6 mmol) were added to a solution of (51a) (1.9 g, 12.6 mmol) in 20 mL of anhydrous DMF. The reaction mixture was heated to 80° C. overnight. After cooling down, the solid was filtered off and rinsed with DMF. The solvent was removed under reduced pressure and the residue was purified on silica gel column to provide methyl 4-(2,3-dihydro-4H-1,4-benzothiazin-4-ylmethyl) benzoate (3.02 g, 80%). MS $(ES^+)$: 300 (M+1).

(51c) A solution of oxone® (2.2 g, 3.54 mmol) in 20 mL of $H_2O$ was added slowly to a solution of (51b) (2.12 g, 7.1 mmol) in 20 mL of MeOH. Upon completion of the reaction, the solution was diluted with ethyl acetate, washed with saturated NaHCO$_3$ and dried over MgSO$_4$. After filtration and concentration, the residue was purified on silica gel column to provide methyl 4-[(1-oxido-2,3-dihydro-4H-1,4-benzothiazin-4-yl)methyl]benzoate (1.39 g, 65%). MS (AP$^+$): 316 (M+1).

(51d) A solution of KOH (1N, 7.5 mL) was added to a solution of (51c) (1.25 g, 3.8 mmol) in 40 mL of MeOH and 40 mL of H$_2$O. The reaction mixture was heated to 60° C. overnight. Upon completion, the aliquot was neutralized with HCl (1N, 7.5 mL). The solvent was removed and the residue was dissolved in MeOH. After filtration and concentration, 4-(2,3-dihydro-4H-1,4-benzothiazin-4-ylmethyl)benzoic acid was obtained in quantitative yield. MS (AP$^+$): 318 (M+1).

(51e) The amine from reaction (2d) (30 mg, 0.15 mmol), diisopropylethylamine (87 mg, 0.11 mL, 0.67 mmol), and CH$_2$Cl$_2$ (2.0 mL) were added to a flask charged with (51d) (42 mg, 0.13 mmol). The whole mixture was cooled to 0° C. and then added BOP (71 mg, 0.23 mmol) in one portion. The resulting solution was stirred overnight and TLC showed completion of the reaction. The solution was directly loaded on silica gel column and purified to provide the desired product (51e) (55 mg, 82%). MS (AP$^+$): 499 (M+1).

(51f) 1 mL of NH$_2$OH/NaOMe/MeOH (1.64 M) was added to a flask charged with the product from (51e) (55 mg, 0.11 mmol) at 0° C. The mixture was stirred for 20 min before it was quenched with 1 mL of aqueous HCl (1N). The resulting solution was then purified by reverse phase HPLC to provide the desired compound (51f) (50 mg, 90%). MS (ES$^+$): 522 (M+Na).

Example 52

(5R,7S,8R)-8-({4-[(2,2-dimethyl-1,1-dioxido-2,3-dihydro-4H-1,4-benzothiazin-4-yl)methyl]benzoyl}amino)-N-hydroxy-1-oxaspiro[4.4]nonane-7-carboxamide (52a) K$_2$CO$_3$ (5.6 g, 40.9 mmol) and ethyl 2-bromoisobutyrate (6.0 mL, 40.9 mmol) were added to a solution of 2-aminothiophenol (5.12 g, 40.9 mmol) in 50 mL of anhydrous DMF at 0° C. The mixture was stirred at 0° C. for 2 h and then heated to 100° C. for 10 h. After cooling down, the solid was filtered off and the solvent was stripped off. The resulting solid was washed with a mixture of dichloromethane and hexane (1:1) to provide the pure product (52a) (4.9 g, 62%). MS (AP$^+$): 194 (M+1).

(52b) To a solution of (52a) (2.0 g, 10.4 mmol) in 40 mL of anhydrous THF at −78° C. as added a solution of LAH in THF (1.0M, 10.4 mL). The reaction mixture was stirred overnight before it was quenched with ethyl acetate, MeOH and H$_2$O. The solution was extracted with ethyl acetate and the combined organic layer was dried over MgSO$_4$. After filtration and concentration, the residue was purified on silica gel column to provide (52b) (1.5 g, 80%). MS (AP$^+$): 180 (M+1).

(52c) To a solution of (52b) (4.0 g, 22.3 mmol) in 50 mL of anhydrous THF at 0° C. as added NaH (1.1 g, 60% dispersion in mineral oil, 26.8 mmol). The mixture was stirred for 30 min before a solution of methyl 4-bromomethylbenzoate in 20 mL of anhydrous THF was added. The reaction was stirred overnight and was quenched with H$_2$O. The solution was extracted with ethyl acetate and washed with H$_2$O and brine, and dried over MgSO$_4$. After filtration and concentration, the residue was purified on silica gel to provide (52c) (5.2 g, 71%). MS (ES$^+$): 328 (M+1).

(52d) Following a procedure similar to (51c), the product from (52c) (2.3 g, 7.0 mmol) was converted to the corresponding sulfone (52d) (1.4 g, 56%). MS (ES$^+$): 719 (2M+1).

(52e) Following a procedure similar to (51d), the product from (52d) (1.4 g, 3.9 mmol) was converted to the corresponding acid (52e) in quantitative yield. MS (ES$^+$): 346 (M+1).

(52f) Following a procedure similar to (51e), the product from (52e) (46 mg, 0.13 mmol) was coupled with the amine from reaction (2d) (30 mg, 0.15 mmol) to provide (52f) (64 mg, 90%). MS (ES$^+$): 527 (M+1).

(52g) Following a procedure similar to (51f), the product from (52f) (45 mg, 0.09 mmol) was converted to the corresponding hydroxamate (52g) (40 mg, 89%). MS (ES$^+$): 550 (M+Na).

Example 53

(5R,7S,8R)-N-hydroxy-8-({4-[(2-methyl-4-quinolinyl)methyl]benzoyl}amino)-1-oxaspiro[4.4]nonane-7-carboxamide (53a) 2-hydroxy-4-methylquinoline (17.4 g, 109 mmol) and phosphorus oxytribromide (47.1 g, 164 mmol) were added to a round-bottom flask. The mixture was heated to 130° C. for several hours. After cooling down to room temperature, the residue was partitioned between saturated Na$_2$CO$_3$ and ethyl acetate. The organic layer was separated and the aqueous layer was extracted with ethyl acetate (5×300 mL). The combined organic layer was washed with H$_2$O (2×400 mL) and brine (1×400 mL) and dried over MgSO$_4$. After filtration and concentration, the residue was purified on silica gel to provide 4-bromo-2-methylquinoline (53a) (8.8 g, 36%). MS (AP$^+$): 224 (M+1).

(53b) 4-Bromo-2-methylquinoline (53a) (1.0 g, 4.5 mmol) was dissolved in 10 mL of anhydrous THF and the resulting solution was cooled down to −78° C. A solution of n-BuLi (3.0 mL, 1.6M, 4.8 mmol) was added slowly and the resulting solution was maintained at −78° C. for 5 min. Meanwhile, in another flask methyl 4-formylbenzoate (0.9 g, 5.4 mmol) was dissolved in 20 mL of anhydrous THF and the resulting solution was cooled to −78° C. before the lithium reagent made above was cannulated. The whole mixture was stirred for 30 min before quenched with MeOH. The solution was then diluted with ethyl acetate and washed with H$_2$O and brine. After dried over MgSO$_4$, the organic solution was filtered and concentrated. The residue was purified on silica gel to provide methyl 4-[hydroxy(2-methyl-4-quinolinyl)methyl]benzoate (0.9 g, 65%). MS (AP$^+$): 308 (M+1).

(53c) The product from (53b) (105 mg, 0.34 mmol) was dissolved in 1 mL of dichloromethane. The solution was cooled to 0° C. and triethylamine (0.1 mL, 0.68 mmol) and MsCl (0.03 mL, 0.41 mmol) were added. The ice bath was removed and the reaction was monitored by TLC until the disappearance of starting material. The solution was diluted with ethyl acetate and washed with H$_2$O and brine. The organic layer was dried over MgSO$_4$, filtered, and concentrated. The residue was purified to provide methyl 4-{(2-methyl-4-quinolinyl)[(methylsulfonyl)oxy]methyl}benzoate in quantitative yield. MS (AP$^+$): 386 (M+1).

(53d) A solution of (53c) (120 mg, 0.31 mmol) in 3 mL of MeOH was added to a suspension of the Pd/C catalyst (60 mg, 10%) in 2 mL of MeOH. The reaction took place after the flask was purged with H$_2$. The reaction was monitored using TLC until disappearance of the starting material. After filtered, the solution was concentrated and the residue was purified on silica gel to provide methyl 4-[(2-methyl-4-quinolinyl)methyl]benzoate in quantitative yield. MS (AP$^+$): 292 (M+1).

(53e) A solution of aqueous NaOH (1N, 35 mL) was added to a solution of (53d) (5.0 g, 17.2 mmol) in 100 mL of MeOH. The reaction mixture was heated up to 60° C. until completion of the reaction, monitored by TLC. Upon the completion, one equivalent of aqueous HCl (1N, 35 mL) was added to neutralize the base. The solution was concentrated to dryness and the residue was redissolved in MeOH. After filtration, the methanolic solution was concentrated again to provide 4-[(2-methyl-4-quinolinyl)methyl]benzoic acid in quantitative yield. MS (ES$^+$): 278 (M+1).

(53f) The amine from reaction (2d) (29 mg, 0.14 mmol), diisopropylethylamine (74 mg, 0.1 mL, 0.6 mmol), dichloromethane (2.0 mL) and DMF (2.0 mL) were added to a flask charged with (53e) (40 mg, 0.14 mmol). The whole mixture was cooled to 0° C. and then BOP (76 mg, 0.17 mmol) was added in one portion. The resulting solution was stirred overnight and TLC showed completion of the reaction. The solution was directly loaded on silica gel column and flash chromatography provides the desired product (53f) (45 mg, 68%). MS (ES$^+$): 459 (M+1).

(53g) 1.0 mL of $NH_2OH$/NaOMe/MeOH at 0° C. as added to a flask charged with compound (53f) (40 mg, 0.09 mmol). The mixture was stirred for 20 min before it was quenched with 1.0 mL of aqueous HCl (1N). The resulting solution was purified by reverse phase HPLC to provide the desired compound(53g) as a TFA salt (53g) (15 mg, 30%). MS (ES$^+$): 460 (M+1).

Example 54

(5R,7S,8R)-N-hydroxy-8-[(4-{[2-(trifluoromethyl)-4-quinolinyl]methyl}benzoyl)amino]-1-oxaspiro[4.4]nonane-7-carboxamide (54a) Following a procedure similar to (53a), 4-hydroxy-2-trifluoromethylquinoline (9.89 g, 46 mmol) was converted to the corresponding bromide (12.5 g, 97%). MS (ES$^+$): 276 (M+1).

(54b) Following a procedure similar to (53b), the product from (54a) (1.0 g, 3.6 mmol) was converted to the corresponding product (54b) (0.38 g, 29%). MS (AP$^+$): 362 (M+1).

(54c) Following a procedure similar to (53c), the product from (54b) (360 mg, 1.0 mmol) was converted to the corresponding mesylate in quantitative yield. MS (AP$^+$): 440 (M+1).

(54d) Following a procedure similar to (53d), the product from (54c) (430 mg, 1.0 mmol) was reduced to the desired product (54d) in quantitative yield. MS (ES$^+$): 346 (M+1).

(54e) Following a procedure similar to (53e), the product from (54d) (340 mg, 1.0 mmol) was converted to the corresponding acid (54e) (320 mg, >95%). MS (AP$^+$): 332 (M+1).

(54f) Following a procedure similar to (53f), the product from (54e) (53 mg, 0.14 mmol) was coupled with the amine from reaction (2d) (30 mg, 0.17 mmol) to provide the desired product (54f) (43 mg, 57%). MS (AP$^+$): 513 (M+1).

(54g) Following a procedure similar to (53g), the product from (54f) (23 mg, 0.045 mmol) was converted to the corresponding hydroxamate as a TFA salt (13 mg, 46%). MS (ES$^+$): 514 (M+1).

Example 55

(5R,7S,8R)-8-({4-[(2-ethyl-4-quinolinyl)methyl]benzoyl}amino)-N-hydroxy-1-oxaspiro[4.4]nonane-7-carboxamide (55a) To a flask were charged aniline (18.6 g, 0.2 mol), methyl propionylacetate (26.0 g, 0.2 mol), p-TsOH (0.3 g) and 100 mL of benzene. The mixture was heated to reflux and water was thus removed via Dean-Stark apparatus. After cooled down, insoluble material was filtered and the filtrate was concentrated to provide crude material in quantitative yield. The crude material was pure enough for next step. The crude material thus obtained was dissolved in 150 mL of $Ph_2O$ and the solution was heated to 240° C. for 1 h. After cooled down, the solution was diluted with hexane and the precipitate (55a) (5.3 g, 15%) was collected. MS (ES$^+$): 174 (M+1).

(55b) Following a procedure similar to (53a), 4-hydroxy-2-ethylquinoline (55a) (5.0 g, 28.9 mmol) was converted to the corresponding bromide (3.6 g, 53%). MS (ES$^+$): 238 (M+1).

(55c) Following a procedure similar to (53b), the product from (55b) (3.0 g, 12.7 mmol) was converted to the desired product (55c) (2.82 g, 69%). MS (AP$^+$): 322 (M+1).

(55d) Following a procedure similar to (53c), the product from (55c) (3.0 g, 9.3 mmol) was converted to the corresponding mesylate (55d) in quantitative yield. MS (AP$^+$): 400 (M+1). (55e) Following a procedure similar to (53d), the product from (55d) (3.7 g, 9.3 mmol) was reduced to the desired product (55e) (2.65 g, 94%). MS (AP$^+$): 306 (M+1).

(55f) Following a procedure similar to (53e), the product from (55e) (2.6 g, 8.5 mmol) was converted to the corresponding acid (55f) (2.4 g, >95%). MS (ES$^+$): 292 (M+1).

(55g) Following a procedure similar to (53f), the product from (55f) (51 mg, 0.18 mmol) was coupled with the amine from reaction (2d) (35 mg, 0.18 mmol) to provide the desired product (55g) (80 mg, >95%). MS (ES$^+$): 473 (M+1).

(55h) Following a procedure similar to (53g), the product from (55g) (80 mg, 0.17 mmol) was converted to the corresponding hydroxamate as a TFA salt (15 mg, 16%). MS (ES$^+$): 474 (M+1).

Example 56

(5R,7S,8R)-N-hydroxy-8-({4-[(2-isopropyl-4-quinolinyl)methyl]benzoyl}amino)-1-oxaspiro[4.4]nonane-7-carboxamide (56a) Malonic acid (4.1 g, 40 mmol) was mixed with phosphorus oxytribromide (35g) in an open vessel at 60° C. Aniline (4.65 g) was carefully added in portion and the mixture was then heated at 130° C. for 3 h. The resulting tar-like material was cooled and carefully transfered into iced water. The solution was neutralized with 1N NaOH and the solid formed was collected. The solid was dissolved into dichloromethane and purified by chromatography to provide 2,4-dibromoquinoline (5.2 g, 44%). MS (ES$^+$): 288 (M+1).

(56b) Tetrakis(triphenylphosphine)palladium (1.1 g, 1.0 mmol) and 2-propenylmagnesium bromide solution (0.5M, 10 mmol, 20 mL) were added to a solution of (56a) (2.9 g, 10.1 mmol) in 20 mL of THF at 0° C. The reaction mixture was stirred at room temperature for 2 days and was quenched with MeOH. The solution was diluted with ethyl acetate and washed with $H_2O$ and brine, and dried over $MgSO_4$. After filtration and concentration, the residue was purified to provide 4-bromo-2-isopropenylquinoline (56b) (1.54 g, 61%). MS (ES$^+$): 249 (M+1).

(56c) A solution of n-BuLi (2.5 M, 7.5 mmol, 3 mL) was added to a solution of (56b) (1.55 g, 6.25 mmol) in 20 mL of anhydrous THF at −78° C. The resulting solution was cannulated to another flask charged with methyl 4-formylbenzoate (1.34 g, 8.1 mmol) in 20 mL of anhydrous THF at −78° C. The reaction mixture was stirred for 3 h at −78° C. before quenched with MeOH. The solution was then diluted with ethyl acetate and washed with H$_2$O and brine, and dried over MgSO$_4$. After filtration and concentration, the residue was purified on silica gel column to provide methyl 4-[hydroxy(2-isopropenyl-4-quinolinyl)methyl] benzoate (0.95 g, 46%). MS (AP$^+$): 333 (M+1).

(56d) The product from (56c) (950 mg, 2.85 mmol) was dissolved in 100 mL of dichloromethane. The solution was cooled to 0° C. and triethylamine (2.0 mL, 14.3 mmol) and MsCl (0.44 mL, 5.7 mmol) were added. The ice bath was removed and the reaction been monitored by TLC until the disappearance of starting material. The solution was diluted with ethyl acetate and washed with H$_2$O and brine. The organic layer was dried over MgSO$_4$, filtered, and concentrated. The residue was purified to provide (56d) (1.0 g, >95%). MS (ES$^+$): 412 (M+1).

(56e) A solution of the mesylate from (56d) (1.0 g, 2.43 mmol) in 10 mL of MeOH and 10 mL of EtOAc was added to a suspension of the Pd/C catalyst (250 mg, 10%) in 20 mL of MeOH. The reaction took place after the flask was purged with H$_2$. The reaction monitored by TLC until disappearance of the starting material. After filtered, the solution was concentrated and the residue was purified on silica gel to provide the desired product (56e) as a methanesulfuric acid salt (1.0 g, quantitative yield). MS (ES$^+$): 320 (M+1).

(56f) A solution of aqueous NaOH (1N, 5 mL) was added to a solution of (56e) (1.0 g, 2.4 mmol) in 10 mL of MeOH. The reaction mixture was heated up to 60° C. until completion of the reaction, monitored by TLC. Upon the completion, one equivalent of aqueous HCl (1N, 5 mL) was added to neutralize the base. The solution was concentrated to dryness and the residue was redissolved in MeOH. After filtration, the methanolic solution was concentrated again to provide the desired product (56f) (700 mg, >95%). MS (ES$^+$): 306 (M+1).

(56g) Following a procedure similar to (53f), the product from (56f) (80 mg, 0.26 mmol) was coupled with the amine from reaction (2d) (52 mg, 0.26 mmol) to provide the desired product (56g) (65 mg, 51%). MS (ES$^+$): 488 (M+1).

(56h) Following a procedure similar to (53g), the product from (56g) (60 mg, 0.12 mmol) was converted to the corresponding hydroxamate as a TFA salt (30 mg, 42%). MS (ES$^+$) 489 (M+1).

Example 57

(5R,7S,8R)-8-[(4-{[2-(dimethylamino)-4-quinolinyl]methyl}benzoyl)amino]-N-hydroxy-1-oxaspiro[4.4]nonane-7-carboxamide (57a) 2,4-dibromoquinoline (56a) (2.0 g, 7.0 mmol) was dissolved in 10 mL of 40% dimethylamine solution in H$_2$O. The reaction mixture was allowed to stir overnight. The solution was diluted to 40 mL with H$_2$O and it was extracted with EtOAc for three times. The combined organic layer was dried over MgSO$_4$. After concentration, the residue was purified on silica gel column to provide 4-bromo-2-dimethylaminoquinoline (57a) (0.69 g, 40%). MS (AP$^+$): 251 (M+1).

(57b) Following a procedure similar to (53b), the product from (57a) (0.67 g, 2.7 mmol) was converted to methyl 4-[hydroxy(2-dimethylamino-4-quinolinyl)methyl]benzoate (57b) (0.15 g, 17%). MS (AP$^+$): 337 (M+1).

(57c) Following a procedure similar to (53c), the product from (57b) (0.15 g, 0.46 mmol) was converted to the corresponding mesylate in quantitative yield. MS (AP$^+$): 415 (M+1).

(57d) Following a procedure similar to (53d), the product from (57c) (0.19 g, 0.46 mmol) was reduced to the desired product (57d) (106 mg, 57%). MS (AP$^+$): 321 (M+1).

(57e) Following a procedure similar to (53e), the product from (57d) (0.1 g, 0.26 mmol) was converted to the corresponding acid (57e) in quantitative yield. MS (ES$^+$): 307 (M+1).

(57f) Following a procedure similar to (53f), the product from (57e) (39 mg, 0.13 mmol) was coupled with the amine from reaction (2d) (31 mg, 0.15 mmol) to provide the desired product (57f) (31 mg, 50%). MS (ES$^+$): 488 (M+1).

(57g) Following a procedure similar to (53g), the product from (57f) (31 mg, 0.06 mmol) was converted to the corresponding hydroxamate as a TFA salt (25 mg, 70%). MS (ES$^+$) 489 (M+1).

Example 58

(5R,7S,8R)-8-({4-[(2-cyclopropyl-4-quinolinyl)methyl]benzoyl}amino)-N-hydroxy-1-oxaspiro[4.4]nonane-7-carboxamide (58a) To a flask were charged aniline (6.55 g, 70 mmol), methyl 3-cyclopropyl-3-oxo-propionate (10.0 g, 70 mmol), p-TsOH (0.3 g) and 100 mL of benzene. The mixture was heated to reflux and water was thus removed via Dean-Stark apparatus. After cooled down, insoluble material was filtered and the filtrate was concentrated. The resulting residue was purified on silica gel column to provide the desired enamine product (58a) (4.5 g, 30%). MS (AP$^+$): 218 (M+1).

(58b) The material from (58a) (4.5 g, 0.021 mol) was dissolved in 50 mL of Ph$_2$O and the solution was heated to 240° C. for 1 h. After cooled down, the solution was diluted with hexane and the precipitate (58b) (3.5 g, 90%) was collected. MS (AP$^+$): 186 (M+1).

(58c) To a solution of 4-hydroxy-2-cyclopropylquinoline (58b) (1.0 g, 5.4 mmol) in 50 mL of anhydrous THF at −78° C. was added LiHMDS (1.0 M, 5.4 mL, 5.4 mmol). The solution was stirred for 1 h, followed by addition of a solution of 2-[N,N-bis(trifluoromethylsulfonyl)amino]-5-chloropyridine (2.33 g, 5.9 mmol) in 10 mL of THF. The mixture was allowed to warm to room temperature overnight. The reaction was quenched with 100 mL of H$_2$O and THF was removed under reduced pressure. The aqueous layer was extracted with EtOAc (4×75 mL) and the combined organic layer was dried over MgSO$_4$. After concentration, the residue was purified on silica gel column to provide the corresponding triflate (58c) (1.21 g, 79%). MS (ES$^+$): 318 (M+1).

(58d) To a solution of (58c) (0.90 g, 3.1 mmol) in 15 mL of DMF were added LiCl (0.27 g, 6.3 mmol), Pd(PPh$_3$)$_4$ (0.36 g, 10 mol%, 0.31 mmol) and 4-(methoxycarbonyl) benzyl zinc bromide (0.5 M, 12.5 mL) (Shiota, T. et al. *J. Org. Chem.* 1999, 64, 453). The solution was stirred at room temperature overnight. DMF solvent was removed under reduced pressure and the residue was taken into 100 mL of H$_2$O. The aqueous phase was extracted by EtOAc (5×50 mL). The combined organic layer was washed with H$_2$O and saturated NaCl and dried over MgSO$_4$. After concentration, the residue was purified on silica gel column to give the desired product (58d) (0.45 g, 45%). MS (ES$^+$): 318 (M+1).

(58e) Following a procedure similar to (53e), the product from (58d) (0.57 g, 1.6 mmol) was converted to the corresponding acid (58e) (0.49 g, 84%). MS (ES$^+$): 304 (M+1).

(58f) Following a procedure similar to (53f), the product from (58e) (50 mg, 0.18 mmol) was coupled with the amine from reaction (2d) (36 mg, 0.18 mmol) to provide the desired product (58f) (72 mg, 90%). MS (ES$^+$): 485 (M+1).

(58g) Following a procedure similar to (53g), the product from (58f) (72 mg, 0.16 mmol) was converted to the corresponding hydroxamate as a TFA salt (64 mg, 66%). MS (ES$^+$): 486 (M+1).

Example 59

(5R,7S,8R)-8-{[4-(1,3-dihydrofuro[3,4-b]quinolin-9-ylmethyl)benzoyl]amino}-N-hydroxy-1-oxaspiro [4.4]nonane-7-carboxamide (59a) Following a procedure similar to (55a), methyl 4-oxotetrahydro-3-furancarboxylate (15.0 g, 0.1 mol) was condensed with aniline to provide the desired product (59a) (10.5 g, 56%). MS (ES$^+$): 188 (M+1).

(59b) Following a procedure similar to (58c), compound (59a) (1.0 g, 5.3 mmol) was converted to the corresponding triflate (59b) (850 mg, 50%). MS (ES$^+$): 320 (M+1).

(59c) Following a procedure similar to (58d), compound (59b) (850 mg, 2.66 mmol) was coupled with 4-(methoxycarbonyl)benzyl zinc bromide to provide the desired product (59c) (290 mg, 34%). MS (ES$^+$): 320 (M+1).

(59d) Following a procedure similar to (53e), the product from (59c) (0.29 g, 0.91 mmol) was converted to the corresponding acid (59d) (0.25 g, 86%). MS (ES$^{31}$): 304 (M−1).

(59e) Following a procedure similar to (53f), the product from (59d) (40 mg, 0.13 mmol) was coupled with the amine from reaction (2d) (26 mg, 0.13 mmol) to provide the desired product (59e) (60 mg, 94%). MS (ES$^+$): 487 (M+1).

(59f) Following a procedure similar to (53g), the product from (59e) (60 mg, 0.12 mmol) was converted to the corresponding hydroxamate as a TFA salt (32 mg, 44%). MS (ES$^+$): 488 (M+1).

Example 60

(5R,7S,8R)-8-({4-[(2,3-dimethyl-4-quinolinyl) methyl]benzoyl}amino)-N-hydroxy-1-oxaspiro[4.4] nonane-7-carboxamide (60a) Ethyl 2-methylacetoacetate (28.8 g, 200 mmol) and catalytic p-toluenesulfuric acid were added to a solution of aniline (18.6 g, 200 mmol) in 200 mL of benzene. The mixture was heated to reflux and water generated in the reaction was collected. Upon the collection of theoretical amount of water, the solution was cooled and insoluble material was filtered off. After concentration of the organic solution, the crude material (60a) (39.0 g, 89%) was used for the next reaction. MS (ES$^+$): 220 (M+1).

(60b) In a flask with distillation head and thermometer to monitor internal temperature was added 120 mL of phenylether. In an additional funnel was charged a solution of (60a) (10.0 g, 45.6 mmol) in 20 mL of phenylether. The flask was preheated to 240° C. and the (60a) solution was added at such a rate that the inner temperature was maintained between 240–245° C. After completion of the addition, the internal temperature of the flask was maintained at 245° C. for 25 min while distilling off ethanol. After cooling down the flask, the solid was filtered off and washed with hexane. The solid thus obtained is 2,3-dimethyl-4-hydroxyquinoline (7.5 g, 95%). MS (ES$^+$): 174 (M+1).

(60c) Following a procedure similar to (53a), the product from (60b) (7.5 g, 43 mmol) was converted to 4-bromo-2,3-dimethylquinoline (6.87 g, 67%). MS (ES$^+$): 236 (M+1).

(60d) Following a similar procedure of (53b), 4-bromo-2,3-dimethylquinoline (3.4 g, 14.6 mmol) was converted to methyl 4-[hydroxy(2,3-dimethyl-4-quinolinyl)methyl] benzoate (0.61 g, 13%). MS (ES$^+$): 322 (M+1).

(60e) Following a similar procedure of (53c), the product from (60d) (0.61 g, 1.9 mmol) was converted to methyl 4-{(2,3-dimethyl-4-quinolinyl)[(methylsulfonyl)oxy] methyl}benzoate (0.66 g, 87%). MS (ES$^+$): 400 (M+1).

(60f) Following a similar procedure of (53d), the product from (60e) was converted to methyl 4-[(2,3-dimethyl-4-quinolinyl)methyl]benzoate in quantitative yield. MS (AP$^+$): 306 (M+1).

(60g) Following a similar procedure of (53e), the product from (60f) was converted to 4-[(2,3-dimethyl-4-quinolinyl) methyl]benzoic acid in quantitative yield. MS (AP$^+$): 292 (M+1).

(60h) Following a similar procedure of (53f), the acid from (60g) (47 mg, 0.14 mmol) was coupled with the amine from reaction (2d) (35 mg, 0.17 mmol) to provide the desired product (53 mg, 77%). MS (AP$^+$): 473 (M+1).

(60i) Following the procedure similar to (53g), the product from (60h) (50 mg, 0.11 mmol) was converted to the corresponding hydroxamate as a TFA salt (60i) (51 mg, 79%). MS (ES$^+$): 474 (M+1).

Example 61

(5R,7S,8R)-N-hydroxy-8-[(4-{[2-methyl-8-(trifluoromethyl)-4-quinolinyl]methyl}benzoyl) amino]-1-oxaspiro[4.4]nonane-7-carboxamide (61a) Following a procedure similar to (55a), 2-trifluoromethylaniline (16.1 g, 0.1 mol) was condensed with methyl acetoacetate to provide the desired product (61a) (12.0 g, 53%). MS (ES$^+$): 228 (M+1).

(61b) Following a procedure similar to (58c), compound (61a) (1.0 g, 4.5 mmol) was converted to the corresponding triflate (61b) (1.49 g, 92%). MS (ES$^+$): 360 (M+1).

(61c) Following a procedure similar to (58d), compound (61b) (1.49 g, 4.15 mmol) was coupled with 4-(methoxycarbonyl)benzyl zinc bromide to provide the desired product (61c) (1.25 g, 83%). MS (ES$^+$): 360 (M+1).

(61d) Following a procedure similar to (53e), the product from (61c) (0.95 g, 2.65 mmol) was converted to the corresponding acid (61d) (0.90 g, >95%). MS (ES$^+$): 346 (M+1).

(61e) Following a procedure similar to (53f), the product from (61d) (40 mg, 0.11 mmol) was coupled with the amine from reaction (2d) (23 mg, 0.12 mmol) to provide the desired product (61e) (50 mg, 82%). MS (ES$^+$): 527 (M+1).

(61f)) Following a procedure similar to (53g), the product from (61e) (50 mg, 0.09 mmol) was converted to the corresponding hydroxamate as a TFA salt (64 mg, 95%). MS (ES$^+$): 528 (M+1).

Example 62

(5R,7S,8R)-8-({4-[(3-ethyl-2-methyl-4-quinolinyl) methyl]benzoyl}amino)-N-hydroxy-1-oxaspiro[4.4] nonane-7-carboxamide (62a) Following a procedure similar to (60a), ethyl 2-ethylacetoacetate (31.6 g, 0.2 mol) was condensed with aniline to provide the desired enamine (62a) in quantitative yield. MS (AP+): 235 (M+1).

(62b) Following a procedure similar to (60b), compound (62a) (10 g, 43 mmol) was converted to the corresponding product (62b) (7.6 g, 95%). MS (AP+): 188 (M+1).

(62c) Following a procedure similar to (53a), compound (62b) (7.5 g, 40 mmol) was converted to the corresponding bromide (6.4 g, 63%). MS (AP+): 252 (M+1).

(62d) Following a procedure similar to (53b), compound (62c) (6.3 g, 25.2 mmol) was converted to the corresponding product (5.4 g, 64%). MS (AP+): 377 (M+CH$_3$CN+1).

(62e) Following a procedure similar to (53c), compound (62d) (5.4 g, 16.1 mmol) was converted to the corresponding product (6.60 g, >95%). MS (AP+): 414 (M+1).

(62f) Following a procedure similar to (53d), compound (62e) (6.6 g, 16.0 mmol) was reduced to the corresponding product (5.1 g, >95%). MS (AP+): 350 (M+CH$_3$CN+1).

(62g) Following a procedure similar to (53e), compound (62f) (5.0 g, 15.7 mmol) was converted to the corresponding acid (3.4 g, 72%). MS (AP+): 306 (M+1).

(62h) Following a procedure similar to (53f), compound (62f) (50 mg, 0.16 mmol) was coupled with the amine from reaction (2d) (33 mg, 0.16 mmol) to provide the desired product (62h) (70 mg, 87%). MS (ES+): 487 (M+1).

(62i) Following a procedure similar to (53g), the product from (62h) (65 mg, 0.13 mmol) was converted to the corresponding hydroxamate as a TFA salt (40 mg, 60%). MS (ES+): 488 (M+1).

Example 63

(5R,7S,8R)-8-({4-[(2,6-dimethyl-4-quinolinyl) methyl]benzoyl}amino)-N-hydroxy-1-oxaspiro[4.4] nonane-7-carboxamide (63a) Following a procedure similar to (55a), 4-methylaniline (21.4 g, 0.2 mol) was condensed with methyl acetoacetate to provide the desired product (63a) (22.0 g, 62%). MS (AP+): 174 (M+1).

(63b) Following a procedure similar to (53a), compound (63a) (22 g, 127 mmol) was converted to the corresponding bromide (15.1 g, 50%). MS (AP+): 236 (M+1).

(63c) Following a procedure similar to (53b), compound (63b) (10.0 g, 42.3 mmol) was converted to the corresponding product (8.4 g, 62%). MS (AP+): 363 (M+CH$_3$CN+1).

(63d) Following a procedure similar to (53c), compound (63c) (8.4 g, 26.4 mmol) was converted to the corresponding mesylate in quantitative yield. MS (AP+): 400 (M+1).

(63e) Following a procedure similar to (53d), compound (63d) (10.4 g, 26.0 mmol) was reduced to the corresponding product in quantitative yield. MS (AP+): 306 (M+1).

(63f) Following a procedure similar to (53e), compound (63e) (8.0 g, 26.0 mmol) was converted to the corresponding acid (7.0 g, >95%). MS (ES+): 292 (M+1).

(63g) Following a procedure similar to (53f), compound (63f) (50 mg, 0.17 mmol) was coupled with the amine from reaction (2d) (35 mg, 0.17 mmol) to provide the desired product (63g) (60 mg, 74%). MS (ES+): 473 (M+1).

(63h) Following a procedure similar to (53g), the product from (63g) (60 mg, 0.13 mmol) was converted to the corresponding hydroxamate as a TFA salt (30 mg, 40%). MS (ES+) 474 (M+1).

Example 64

(5R,7S,8R)-8-({4-[(6-chloro-2-methyl-4-quinolinyl) methyl]benzoyl}amino)-N-hydroxy-1-oxaspiro[4.4] nonane-7-carboxamide (64a) Following a procedure similar to (55a), 4-chloroaniline (25.5 g, 0.2 mol) was condensed with methyl acetoacetate to provide the desired product (64a) (17.6 g, 45%). MS (AP+) 194 (M+1).

(64b) Following a procedure similar to (58c), compound (64a) (1.0 g, 5.16 mmol) was converted to the corresponding triflate (64b) (0.72 g, 43%). MS (AP+): 326 (M+1).

(64c)) Following a procedure similar to (58d), compound (64b) (0.7 g, 2.15 mmol) was coupled with 4-(methoxycarbonyl)benzyl zinc bromide to provide the desired product (64c) (0.49 g, 70%). MS (AP+): 326 (M+1).

(64d) Following a procedure similar to (53e), the product from (64c) (0.49 g, 1.5 mmol) was converted to the corresponding acid (64d) in quantitative yield. MS (AP+): 312 (M+1).

(64e) Following a procedure similar to (53f), the product from (64d) (50 mg, 0.16 mmol) was coupled with the amine from reaction (2d) (32 mg, 0.16 mmol) to provide the desired product (64e) in quantitative yield. MS (ES+): 493 (M+1).

(64f)) Following a procedure similar to (53g), the product from (64e) (70 mg, 0.14 mmol) was converted to the corresponding hydroxamate as a TFA salt (40 mg, 47%). MS (ES+): 494 (M+1).

Example 65

(5R,7S,8R)-8-({4-[(6-fluoro-2-methyl-4-quinolinyl) methyl]benzoyl}amino)-N-hydroxy-1-oxaspiro[4.4] nonane-7-carboxamide (65a) Following a procedure similar to (55a), 4-fluoroaniline (11.1 g, 0.1 mol) was condensed with methyl acetoacetate to provide the desired product (65a) (10.5 g, 59%). MS (ES+): 178 (M+1).

(65b) Following a procedure similar to (58c), compound (65a) (2.0 g, 11.3 mmol) was converted to the corresponding triflate (65b) (1.93 g, 55%). MS (ES+): 310 (M+1).

(65c)) Following a procedure similar to (58d), compound (65b) (0.38 g, 1.2 mmol) was coupled with 4-(methoxycarbonyl)benzyl zinc bromide to provide the desired product (65c) (0.13 g, 34%). MS (AP+): 310 (M+1).

(65d) Following a procedure similar to (53e), the product from (65c) (0.13 g, 0.4 mmol) was converted to the corresponding acid (65d) (82 mg, 66%). MS (AP+): 296 (M+1).

(65e) Following a procedure similar to (53f), the product from (65d) (40 mg, 0.13 mmol) was coupled with the amine from reaction (2d) (29 mg, 0.15 mmol) to provide the desired product (65e) (57 mg, 90%). MS (AP+): 477 (M+1).

(65f) Following a procedure similar to (53g), the product from (65e) (54 mg, 0.11 mmol) was converted to the corresponding hydroxamate as a TFA salt (54 mg, 83%). MS (ES+): 478 (M+1).

Example 66

(5R,7S,8R)-8-({4-[(7-chloro-2-methyl-4-quinolinyl) methyl]benzoyl}amino)-N-hydroxy-1-oxaspiro[4.4] nonane-7-carboxamide (66a) Following a procedure similar to (55a), 3-chloroaniline (12.7 g, 0.1 mol) was condensed with methyl acetoacetate to provide the desired product (66a) (7.7 g, 79%). MS (AP+): 194 (M+1).

(66b) Following a procedure similar to (58c), compound (66a) (2.0 g, 10.3 mmol) was converted to the corresponding triflate (66b) (1.56 g, 46%). MS (AP+): 326 (M+1).

(66c) Following a procedure similar to (58d), compound (66b) (1.5 g, 4.6 mmol) was coupled with 4-(methoxycarbonyl)benzyl zinc bromide to provide the desired product (66c) (0.47 g, 31%). MS (ES⁺): 326 (M+1).

(66d) Following a procedure similar to (53e), the product from (66c) (0.47 g, 1.4 mmol) was converted to the corresponding acid (65d) (375 mg, 84%). MS (ES⁺): 353 (M+CH₃CN+1).

(66e) Following a procedure similar to (53f), the product from (66d) (50 mg, 0.16 mmol) was coupled with the amine from reaction (2d) (36 mg, 0.18 mmol) to provide the desired product (66e) (74 mg, 93%). MS (ES⁺): 493 (M+1).

(66f)) Following a procedure similar to (53g), the product from (66e) (70 mg, 0.14 mmol) was converted to the corresponding hydroxamate as a TFA salt (50 mg, 59%). MS (ES⁺): 494 (M+1).

Example 67

(5R,7S,8R)-8-({4-[(2,6-dimethyl-4-pyridinyl)methyl]benzoyl}amino)-N-hydroxy-1-oxaspiro[4.4]nonane-7-carboxamide (67a) Following a procedure similar to (53a), 1H-pyridin-4-one (6.0 g, 48.7 mmol) was converted to the corresponding bromide (7.2 g, 79%). MS (ES⁺): 186 (M+1).

(67b) Following a procedure similar to (53b), the product from (67a) (1.0 g, 5.4 mmol) was converted to the corresponding product (67b) (0.37 g, 25%). MS (ES⁺): 272 (M+1).

(67c) Following a procedure similar to (53c), the product from (67b) (366 mg, 1.35 mmol) was converted to the corresponding mesylate (67c) in quantitative yield. MS (AP⁺): 391 (M+CH₃CN+1).

(67d) Following a procedure similar to (53d), the product from (67c) (470 mg, 1.35 mmol) was reduced to the desired product (67d) in quantitative yield. MS (ES⁺): 256 (M+1).

(67e) Following a procedure similar to (53e), the product from (67d) (460 mg, 1.34 mmol) was converted to the corresponding acid (67e) in quantitative yield. MS (AP⁺): 242 (M+1).

(67f) Following a procedure similar to (53f), the product from (67e) (67 mg, 0.24 mmol) was coupled with the amine from reaction (2d) (58 mg, 0.29 mmol) to provide the desired product (67f) (45 mg, 44%). MS (AP⁺): 423 (M+1).

(67g) Following a procedure similar to (53g), the product from (67f) (45 mg, 0.11 mmol) was converted to the corresponding hydroxamate as a TFA salt (45 mg, 76%). MS (ES⁺): 424 (M+1).

Table 1 below provides representative Examples, the synthesis of which is described above, of the compounds of the present invention.

TABLE 1

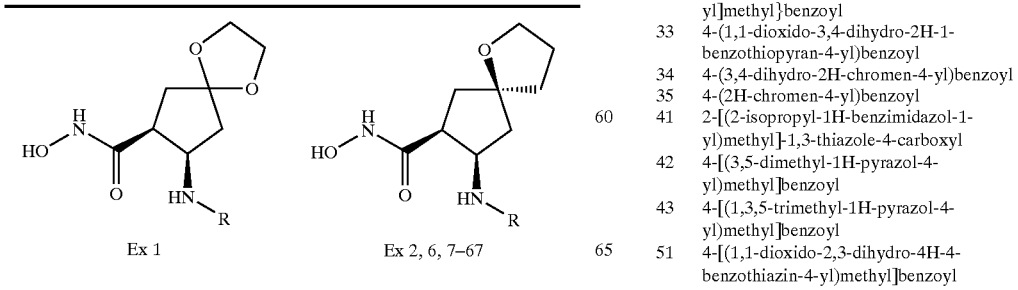

Ex 1     Ex 2, 6, 7–67

TABLE 1-continued

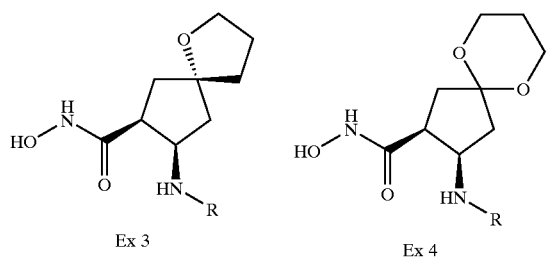

Ex 3     Ex 4

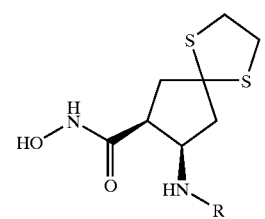

Ex 5

| Ex | R | MS [M + H] or [M + Na] |
|----|---|---|
| 1  | 4-(2-methyl-4-quinolinylmethoxy)benzoyl | 478 |
| 2  | 4-(2-methyl-4-quinolinylmethoxy)benzoyl | 476 |
| 3  | 4-(2-methyl-4-quinolinylmethoxy)benzoyl | 476 |
| 4  | 4-(2-methyl-4-quinolinylmethoxy)benzoyl | 492 |
| 5  | 4-(2-methyl-4-quinolinylmethoxy)benzoyl | 510 |
| 6  | 4-(2-butynyloxy)benzoyl | 393 |
| 7  | 4-[(2-methyl-1H-benzimidazol-1-yl)methyl]benzoyl | 449 |
| 8  | 4-[(2-isopropyl-1H-benzimidazol-1-yl)methyl]benzoyl | 477 |
| 9  | 4-{[2-(trifluoromethyl)-1H-benzimidazol-1-yl]methyl}benzoyl | 503 |
| 10 | 4-[(2-tert-butyl-1H-benzimidazol-1-yl)methyl]benzoyl | 492 |
| 11 | 4-[(2-methyl-1H-indol-3-yl)methyl]benzoyl | 448 |
| 12 | 4-{[2-(difluoromethyl)-1H-benzimidazol-1-yl]methyl}benzoyl | 485 |
| 13 | 4-[(2-cyclopropyl-1H-benzimidazol-1-yl)methyl]benzoyl | 475 |
| 14 | 4-[(2-cyclobutyl-1H-benzimidazol-1-yl)methyl]benzoyl | 490 |
| 15 | 4-[(2-isopropyl-1H-imidazol-1-yl)methyl]benzoyl | 427 |
| 16 | 4-[(2-methyl-1H-indol-1-yl)methyl]benzoyl | 448 |
| 17 | 4-{[2-(1-methylcyclopropyl)-1H-benzimidazol-1-yl]methyl}benzoyl | 489 |
| 18 | 4-{[2-(fluoromethyl)-1H-benzimidazol-1-yl]methyl}benzoyl | 467 |
| 19 | 4-{[2-(1-fluoro-1-methylethyl)-1H-benzimidazol-1-yl]methyl}benzoyl | 495 |
| 20 | 4-(1H-indol-3-ylmethyl)benzoyl | 435 |
| 21 | 4-{[2-(1,1-difluoroethyl)-1H-benzimidazol-1-yl]methyl}benzoyl | 499 |
| 22 | 4-[(2,3-dimethyl-1H-indol-1-yl)methyl]benzoyl | 462 |
| 23 | 4-[(2-ethyl-1H-indol-3-yl)methyl]benzoyl | 462 |
| 24 | 4-{[2-(trifluoromethyl)-1H-indol-1-yl]methyl}benzoyl | 501 |
| 33 | 4-(1,1-dioxido-3,4-dihydro-2H-1-benzothiopyran-4-yl)benzoyl | 485 |
| 34 | 4-(3,4-dihydro-2H-chromen-4-yl)benzoyl | 435 |
| 35 | 4-(2H-chromen-4-yl)benzoyl | 433 |
| 41 | 2-[(2-isopropyl-1H-benzimidazol-1-yl)methyl]-1,3-thiazole-4-carboxyl | 484 |
| 42 | 4-[(3,5-dimethyl-1H-pyrazol-4-yl)methyl]benzoyl | 413 |
| 43 | 4-[(1,3,5-trimethyl-1H-pyrazol-4-yl)methyl]benzoyl | 427 |
| 51 | 4-[(1,1-dioxido-2,3-dihydro-4H-4-benzothiazin-4-yl)methyl]benzoyl | 522 |

TABLE 1-continued

| 52 | 4-[(2,2-dimethyl-1,1-dioxido-2,3-dihydro-4H-1,4-benzothiazin-4-yl)methyl]benzoyl | 550 |
| 53 | 4-[(2-methyl-4-quinolinyl)methyl]benzoyl | 460 |
| 54 | 4-{[2-(trifluoromethyl)-4-quinolinyl]methyl}benzoyl | 514 |
| 55 | 4-[(2-ethyl-4-quinolinyl)methyl]benzoyl | 474 |
| 56 | 4-[(2-isopropyl-4-quinolinyl)methyl]benzoyl | 489 |
| 57 | 4-{[2-(dimethylamino)-4-quinolinyl]methyl}benzoyl | 489 |
| 58 | 4-[(2-cyclopropyl-4-quinolinyl)methyl]benzoyl | 486 |
| 59 | 4-(1,3-dihydrofuro[3,4-b]quinolin-9-ylmethyl)benzoyl | 488 |
| 60 | 4-[(2,3-dimethyl-4-quinolinyl)methyl]benzoyl | 474 |
| 61 | 4-{[2-methyl-8-(trifluoromethyl)-4-quinolinyl]methyl}benzoyl | 528 |
| 62 | 4-[(3-ethyl-2-methyl-4-quinolinyl)methyl]benzoyl | 488 |
| 63 | 4-[(2,6-dimethyl-4-quinolinyl)methyl]benzoyl | 474 |
| 64 | 4-[(6-chloro-2-methyl-4-quinolinyl)methyl]benzoyl | 494 |
| 65 | 4-[(6-fluoro-2-methyl-4-quinolinyl)methyl]benzoyl | 478 |
| 66 | 4-[(7-chloro-2-methyl-4-quinolinyl)methyl]benzoyl | 494 |
| 67 | 4-[(2,6-dimethyl-4-pyridinyl)methyl]benzoyl | 424 |

The following tables contain representative examples of the present invention. Each entry in each table is intended to be paired with each formula at the start of the table. For example, example 1 is intended to be paired with each of formulae A–J.

TABLE 2

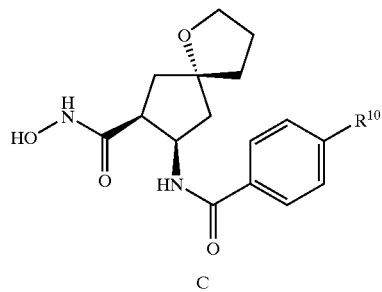

A

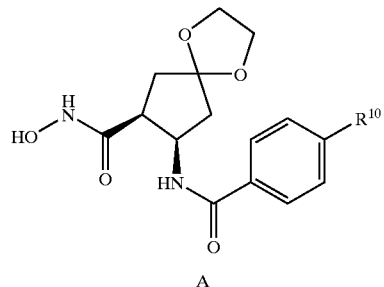

B

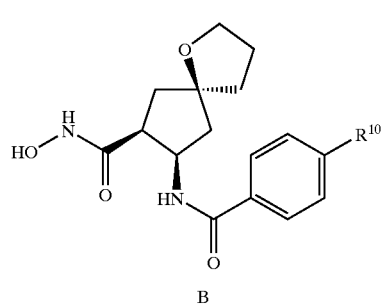

C

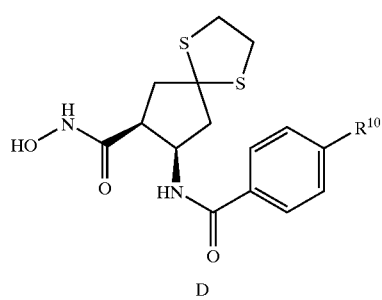

D

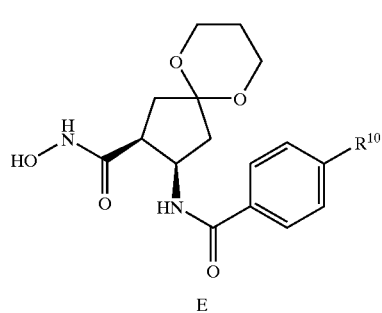

E

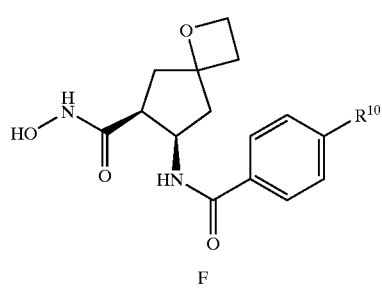

F

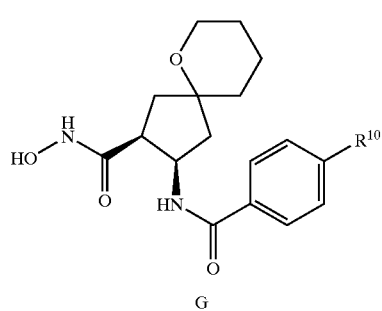

G

TABLE 2-continued
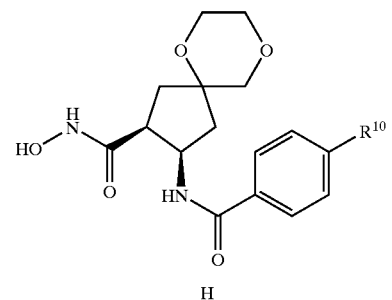
H
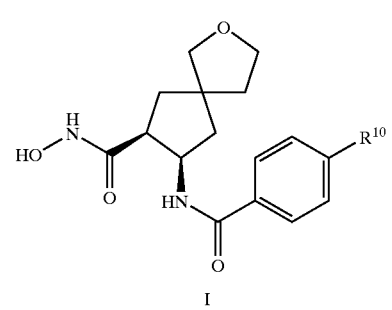
I
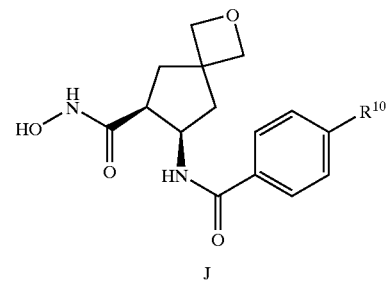
J
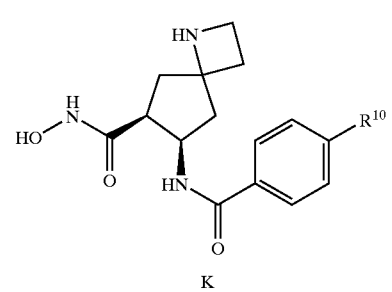
K
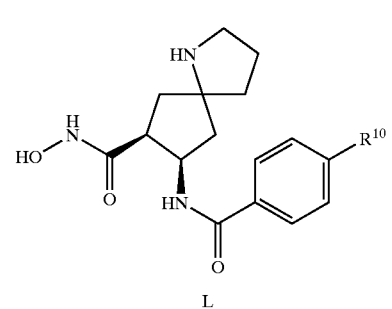
L
TABLE 2-continued
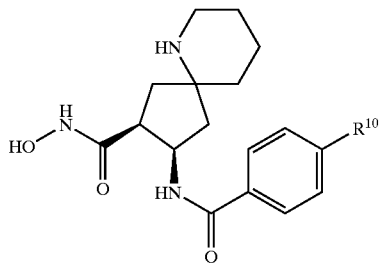
M
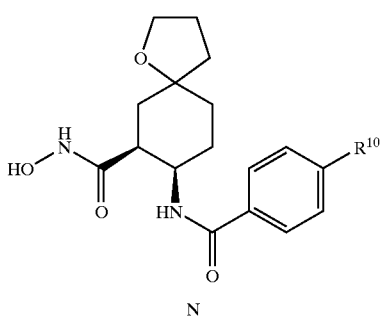
N
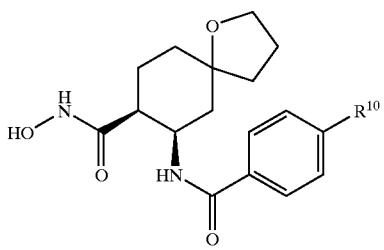
O
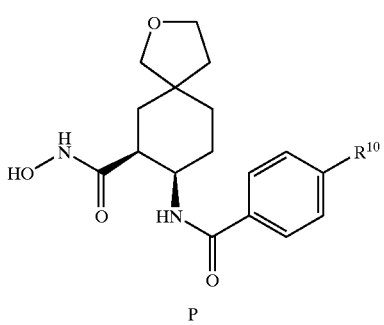
P
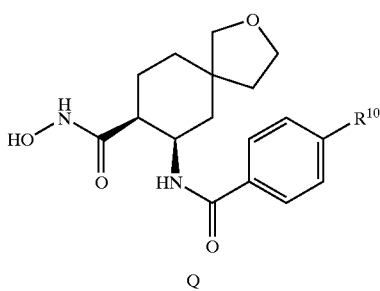
Q TABLE 2-continued

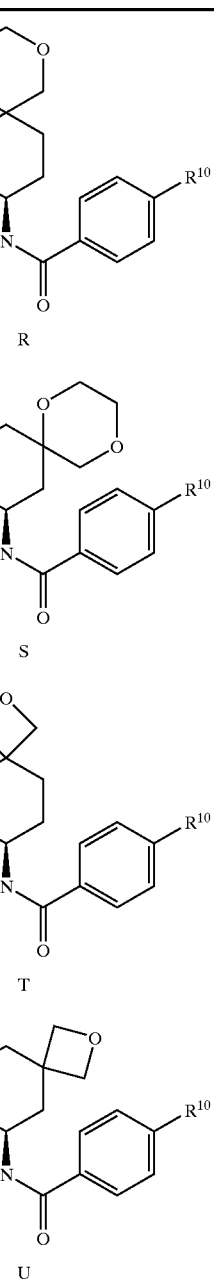

R

S

T

U

| Ex # | R$^{10}$ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)methoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl |
| 93 | 2-butynyloxy |
| 94 | 4-hydroxy-2-butynyloxy |
| 95 | 4-pyridyl |

TABLE 2-continued

| | |
|---|---|
| 96 | 4-pyridoxy |
| 97 | (2-methyl-4-quinolinyl)methylamino |
| 98 | 3-phenyl-4,5-dihydro-5-isoxazolyl |
| 99 | 3-(4-pyridinyl)-4,5-dihydro-5-isoxazolyl |
| 100 | 5-(4-pyridinyl)-4,5-dihydro-3-isoxazolyl |
| 101 | (2-methyl-1H-benzimidazol-1-yl)methyl |
| 102 | (2-isopropyl-1H-benzimidazol-1-yl)methyl |
| 103 | [2-(trifluoromethyl)-1H-benzimidazol-1-yl]methyl |
| 104 | (2-tert-butyl-1H-benzimidazol-1-yl)methyl |
| 105 | (2-methyl-1H-indol-3-yl)methyl |
| 106 | [2-(difluoromethyl)-1H-benzimidazol-1-yl]methyl |
| 107 | (2-cyclopropyl-1H-benzimidazol-1-yl)methyl |
| 108 | (2-cyclobutyl-1H-benzimidazol-1-yl)methyl |
| 109 | (2-isopropyl-1H-imidazol-1-yl)methyl |
| 110 | (2-methyl-1H-indol-1-yl)methyl |
| 111 | [2-(1-methylcyclopropyl)-1H-benzimidazol-1-yl]methyl |
| 112 | [2-(fluoromethyl)-1H-benzimidazol-1-yl]methyl |
| 113 | [2-(1-fluoro-1-methylethyl)-1H-benzimidazol-1-yl]methyl |
| 114 | 1H-indol-3-ylmethyl |
| 115 | [2-(1,1-difluoroethyl)-1H-benzimidazol-1-yl]methyl |
| 116 | (2,3-dimethyl-1H-indol-1-yl)methyl |
| 117 | (2-ethyl-1H-indol-3-yl)methyl |
| 118 | 2-(trifluoromethyl)-1H-indol-1-yl]methyl |
| 119 | 3,4-dihydro-2H-chromen-4-yl |
| 120 | 1,1-dioxido-3,4-dihydro-2H-1-benzothiopyran-4-yl |
| 121 | 2H-chromen-4-yl |
| 122 | (3,5-dimethyl-1H-pyrazol-4-yl)methyl |
| 123 | (1,3,5-trimethyl-1H-pyrazol-4-yl)methyl |
| 124 | (1,1-dioxido-2,3-dihydro-4H-1,4-benzothiazin-4-yl)methyl |
| 125 | (2,2-dimethyl-1,1-dioxido-2,3-dihydro-4H-1,4-benzothiazin-4-yl)methyl |
| 126 | (2-methyl-4-quinolinyl)methyl |
| 127 | [2-(trifluoromethyl)-4-quinolinyl]methyl |
| 128 | (2-ethyl-4-quinolinyl)methyl |
| 129 | (2-isopropyl-4-quinolinyl)methyl |
| 130 | [2-(dimethylamino)-4-quinolinyl]methyl |
| 131 | (2-cyclopropyl-4-quinolinyl)methyl |
| 132 | 1,3-dihydrofuro[3,4-b]quinolin-9-ylmethyl |
| 133 | (2,3-dimethyl-4-quinolinyl)methyl |
| 134 | [2-methyl-8-(trifluoromethyl)-4-quinolinyl]methyl |
| 135 | 3-ethyl-2-methyl-4-quinolinylmethyl |
| 136 | (2,6-dimethyl-4-quinolinyl)methyl |
| 137 | 6-chloro-2-methyl-4-quinolinylmethyl |
| 138 | 6-fluoro-2-methyl-4-quinolinylmethyl |
| 139 | 7-chloro-2-methyl-4-quinolinylmethyl |
| 140 | 2,6-dimethyl-4-pyridinylmethyl |
| 141 | 2-methyl-pyrazolo[1,5-a]pyridin-3-ylmethyl |
| 142 | 2-ethyl-pyrazolo[1,5-a]pyridin-3-ylmethyl |
| 143 | 2-cyclopropyl-pyrazolo[1,5-a]pyridin-3-ylmethyl |
| 144 | 2-isopropyl-pyrazolo[1,5-a]pyridin-3-ylmethyl |
| 145 | 2-t-butyl-pyrazolo[1,5-a]pyridin-3-ylmethyl |
| 146 | 2-trifluoromethyl-pyrazolo[1,5-a]pyridin-3-ylmethyl |
| 147 | 2-difluoromethyl-pyrazolo[1,5-a]pyridin-3-ylmethyl |
| 148 | 2-fluoromethyl-pyrazolo[1,5-a]pyridin-3-ylmethyl |
| 149 | 2-methyl-imidazo[1,2-a]pyridin-3-ylmethyl |
| 150 | 2-ethyl-imidazo[1,2-a]pyridin-3-ylmethyl |
| 151 | 2-isopropyl-imidazo[1,2-a]pyridin-3-ylmethyl |
| 152 | 2-cyclopropyl-imidazo[1,2-a]pyridin-3-ylmethyl |
| 153 | 2-t-butyl-imidazo[1,2-a]pyridin-3-ylmethyl |
| 154 | 2-trifluoromethyl-imidazo[1,2-a]pyridin-3-ylmethyl |
| 155 | 2-trifluoromethyl-imidazo[1,2-a]pyridin-3-ylmethyl |
| 156 | 2-fluoromethyl-imidazo[1,2-a]pyridin-3-ylmethyl |
| 157 | 2-methyl-1H-imidazo[4,5-b]pyridin-1-ylmethyl |
| 158 | 2-ethyl-1H-imidazo[4,5-b]pyridin-1-ylmethyl |
| 159 | 2-isopropyl-1H-imidazo[4,5-b]pyridin-1-ylmethyl |
| 160 | 2-cyclopropyl-1H-imidazo[4,5-b]pyridin-1-ylmethyl |
| 161 | 2-t-butyl-1H-imidazo[4,5-b]pyridin-1-ylmethyl |
| 162 | 2-trifluoromethyl-1H-imidazo[4,5-b]pyridin-1-ylmethyl |

TABLE 2-continued

| | |
|---|---|
| 163 | 2-difuoromethyl-1H-imidazo[4,5-b]pyridin-1-ylmethyl |
| 164 | 2-fluoromethyl-1H-imidazo[4,5-b]pyridin-1-ylmethyl |

TABLE 3

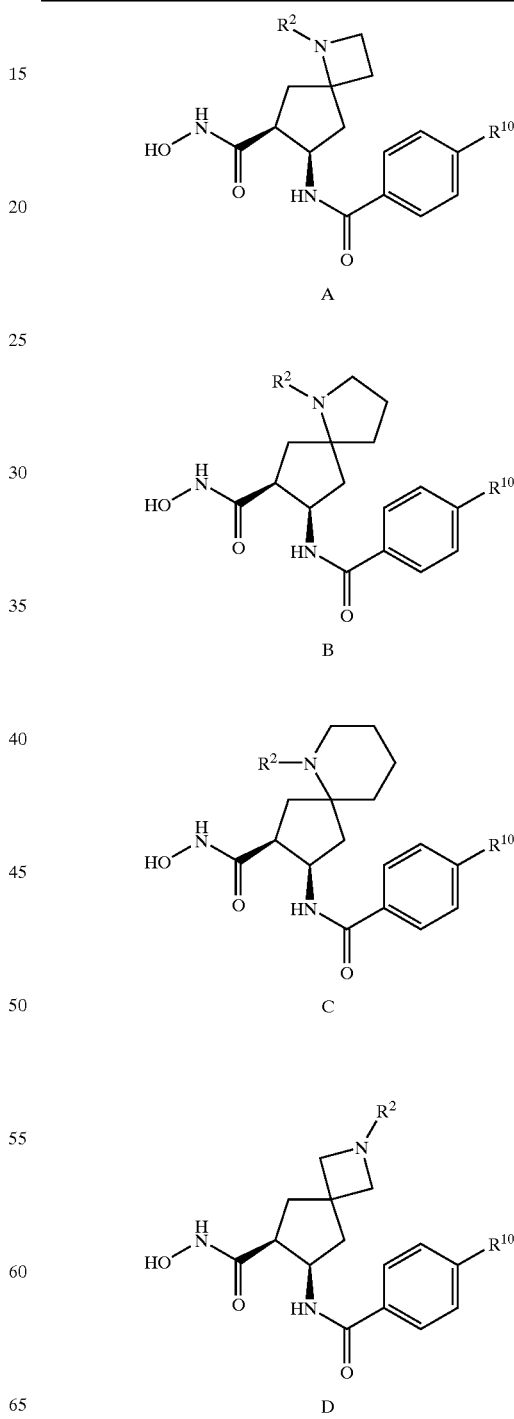

TABLE 3-continued
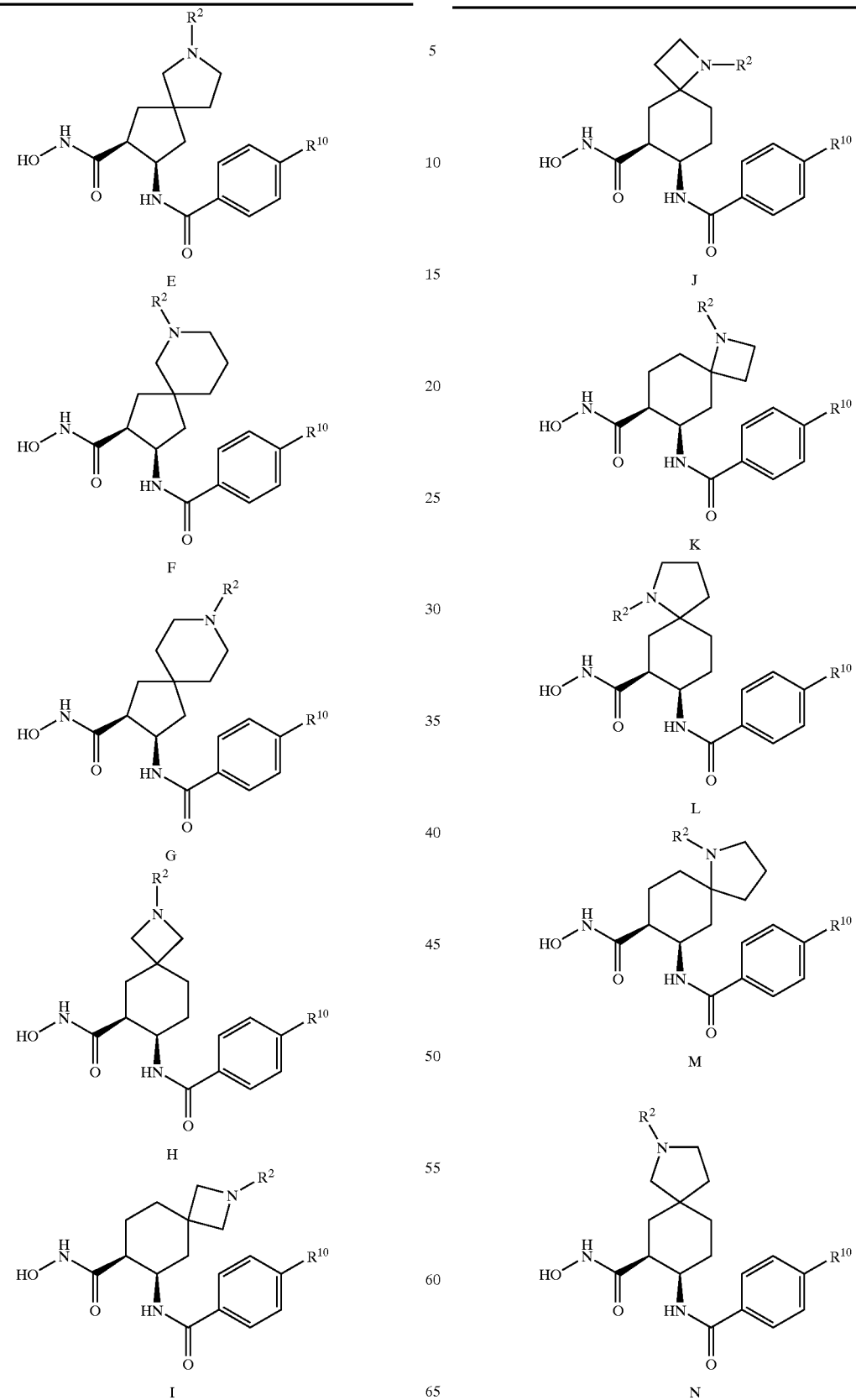

TABLE 3-continued

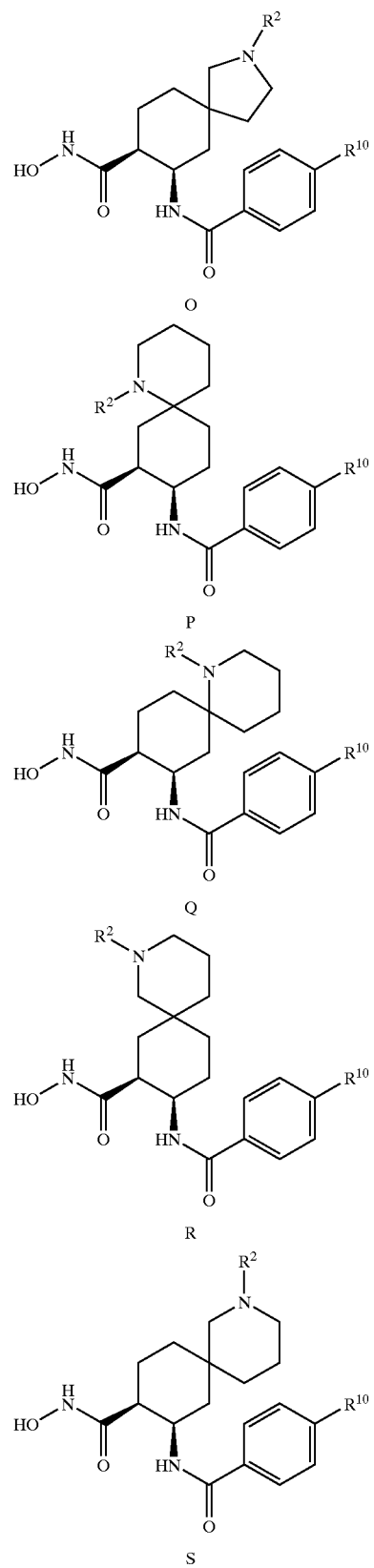

O

P

Q

R

S

TABLE 3-continued

T

U

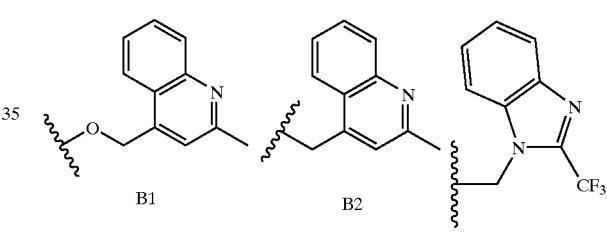

B1   B2   B3

| Ex # | R² | R¹⁰ |
|---|---|---|
| 1 | H | B1 |
| 2 | methyl | B1 |
| 3 | ethyl | B1 |
| 4 | 1-methylethyl | B1 |
| 5 | cyclobutyl | B1 |
| 6 | n-butyl | B1 |
| 7 | 2,2-dimethylpropyl | B1 |
| 8 | cyclopropylmethyl | B1 |
| 9 | 2-methoxyethyl | B1 |
| 10 | 2-hydroxyethyl | B1 |
| 11 | 2-aminoethyl | B1 |
| 12 | 2-dimethylaminoethyl | B1 |
| 13 | 2-(4-morpholinyl)ethyl | B1 |
| 14 | 2-(1-piperidinyl)ethyl | B1 |
| 15 | 2-(1-piperidinyl)ethyl | B1 |
| 16 | phenyl | B1 |
| 17 | benzyl | B1 |
| 18 | 3-picolyl | B1 |
| 19 | formyl | B1 |
| 20 | acetyl | B1 |
| 21 | pivaloyl | B1 |
| 22 | benzoyl | B1 |
| 23 | nicotinoyl | B1 |
| 24 | methanesulfonyl | B1 |
| 25 | benzenesulfonyl | B1 |
| 26 | t-butylsulfonyl | B1 |
| 27 | methoxycarbonyl | B1 |
| 28 | t-butoxycarbonyl | B1 |
| 29 | isopropyloxycarbonyl | B1 |

TABLE 3-continued

| | | |
|---|---|---|
| 30 | Dimethylcarbamyl | B1 |
| 31 | 4-morpholinecarbonyl | B1 |
| 32 | 2-thiophenecarbonyl | B1 |
| 33 | 2-fluoroethyl | B1 |
| 34 | 2,2-difluoroethyl | B1 |
| 35 | 2-(dimethylamino)-2-oxoethyl | B1 |
| 36 | 2-oxo-2-(4-morphorlinyl)ethyl | B1 |
| 37 | tert-butyl | B1 |
| 38 | 1,1-dimethylpropyl | B1 |
| 39 | 2-propenyl | B1 |
| 40 | 1-methyl-2-propenyl | B1 |
| 41 | 1,1-dimethyl-2-propenyl | B1 |
| 42 | 2-propynyl | B1 |
| 43 | 1-methyl-2-propynyl | B1 |
| 44 | 1,1-dimethyl-2-propynyl | B1 |
| 45 | (2-pyrrolidinyl)methyl | B1 |
| 46 | H | B2 |
| 47 | methyl | B2 |
| 48 | ethyl | B2 |
| 49 | 1-methylethyl | B2 |
| 50 | cyclobutyl | B2 |
| 51 | n-butyl | B2 |
| 52 | 2,2-dimethylpropyl | B2 |
| 53 | cyclopropylmethyl | B2 |
| 54 | 2-methoxyethyl | B2 |
| 55 | 2-hydroxyethyl | B2 |
| 56 | 2-aminoethyl | B2 |
| 57 | 2-dimethylaminoethyl | B2 |
| 58 | 2-(4-morpholinyl)ethyl | B2 |
| 59 | 2-(1-piperidinyl)ethyl | B2 |
| 60 | 2-(1-piperizinyl)ethyl | B2 |
| 61 | phenyl | B2 |
| 62 | benzyl | B2 |
| 63 | 3-picolyl | B2 |
| 64 | formyl | B2 |
| 65 | acetyl | B2 |
| 66 | pivaloyl | B2 |
| 67 | benzoyl | B2 |
| 68 | nicotinoyl | B2 |
| 69 | methanesulfonyl | B2 |
| 70 | benzenesulfonyl | B2 |
| 71 | t-butylsulfonyl | B2 |
| 72 | methoxycarbonyl | B2 |
| 73 | t-butoxycarbonyl | B2 |
| 74 | isopropyloxycarbonyl | B2 |
| 75 | Dimethylcarbamyl | B2 |
| 76 | 4-morpholinecarbonyl | B2 |
| 77 | 2-thiophenecarbonyl | B2 |
| 78 | 2-fluoroethyl | B2 |
| 79 | 2,2-difluoroethyl | B2 |
| 80 | 2-(dimethylamino)-2-oxoethyl | B2 |
| 81 | 2-oxo-2-(4-morphorlinyl)ethyl | B2 |
| 82 | tert-butyl | B2 |
| 83 | 1,1-dimethylpropyl | B2 |
| 84 | 2-propenyl | B2 |
| 85 | 1-methyl-2-propenyl | B2 |
| 86 | 1,1-dimethyl-2-propenyl | B2 |
| 87 | 2-propynyl | B2 |
| 88 | 1-methyl-2-propynyl | B2 |
| 89 | 1,1-dimethyl-2-propynyl | B2 |
| 90 | (2-pyrrolidinyl)methyl | B2 |
| 91 | H | B3 |
| 92 | methyl | B3 |
| 93 | ethyl | B3 |
| 94 | 1-methylethyl | B3 |
| 95 | cyclobutyl | B3 |
| 96 | n-butyl | B3 |
| 97 | 2,2-dimethylpropyl | B3 |
| 98 | cyclopropylmethyl | B3 |
| 99 | 2-methoxyethyl | B3 |
| 100 | 2-hydroxyethyl | B3 |
| 101 | 2-aminoethyl | B3 |
| 102 | 2-dimethylaminoethyl | B3 |
| 103 | 2-(4-morpholinyl)ethyl | B3 |
| 104 | 2-(1-piperidinyl)ethyl | B3 |
| 105 | 2-(1-piperizinyl)ethyl | B3 |
| 106 | phenyl | B3 |
| 107 | benzyl | B3 |
| 108 | 3-picolyl | B3 |

TABLE 3-continued

| | | |
|---|---|---|
| 109 | formyl | B3 |
| 110 | acetyl | B3 |
| 111 | pivaloyl | B3 |
| 112 | benzoyl | B3 |
| 113 | nicotinoyl | B3 |
| 114 | methanesulfonyl | B3 |
| 115 | benzenesulfonyl | B3 |
| 116 | t-butylsulfonyl | B3 |
| 117 | methoxycarbonyl | B3 |
| 118 | t-butoxycarbonyl | B3 |
| 119 | isopropyloxycarbonyl | B3 |
| 120 | Dimethylcarbamyl | B3 |
| 121 | 4-morpholinecarbonyl | B3 |
| 122 | 2-thiophenecarbonyl | B3 |
| 123 | 2-fluoroethyl | B3 |
| 124 | 2,2-difluoroethyl | B3 |
| 125 | 2-(dimethylamino)-2-oxoethyl | B3 |
| 126 | 2-oxo-2-(4-morphorlinyl)ethyl | B3 |
| 127 | tert-butyl | B3 |
| 128 | 1,1-dimethylpropyl | B3 |
| 129 | 2-propenyl | B3 |
| 130 | 1-methyl-2-propenyl | B3 |
| 131 | 1,1-dimethyl-2-propenyl | B3 |
| 132 | 2-propynyl | B3 |
| 133 | 1-methyl-2-propynyl | B3 |
| 134 | 1,1-dimethyl-2-propynyl | B3 |
| 135 | (2-pyrrolidinyl)methyl | B3 |

UTILITY

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone that occurs in osteoporosis patients.

Compounds that inhibit the production or action of TACE and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholism, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma stands for the Sigma-Aldrich Corp. of St. Louis, Mo.

A compound is considered to be active if it has an $IC_{50}$ or $K_i$ value of less than about 10 $\mu$M for the inhibition of a desired MP. Preferred compounds of the present invention have $K_i$'s or $IC_{50}$'s of $\leq 1$ $\mu$M. More preferred compounds of the present invention have $K_i$'s or $IC_{50}$'s of $\leq 0.1$ $\mu$M. Even more preferred compounds of the present invention have $K_i$'s or $IC_{50}$'s of $\leq 0.01$ $\mu$M. Still more preferred compounds of the present invention have $K_i$'s or $IC_{50}$'s of $\leq 0.001$ $\mu$M.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-$\alpha$) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. Trans. Ortho. Res. Soc. 1995, 20, 341). Therefore, in order to accumulate BNC aggrecanase in culture media, cartilage is first depleted of endogenous aggrecan by stimulation with 500 ng/ml human recombinant IL-$\beta$ for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C. E. et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 $\mu$M for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 $\mu$l of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at $2 \times 10^6$ cells/ml in 96 well polystyrene plates. Cells were preincubated 10 minutes with compound, then stimulated with 1 μg/ml LPS (Lipopolysaccharide, Salmonella typhimurium) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 μl of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 μl of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction in Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 μM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibiton, the $IC_{50}$ values were converted to Ki values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$s's of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension

|  | Wt. % |
| --- | --- |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

Resuspendable Powder

|  | Wt. % |
| --- | --- |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

|  | Wt. % |
| --- | --- |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Semi-Solid Paste

|  | Wt. % |
| --- | --- |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste

|  | Wt. % |
| --- | --- |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine.

Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

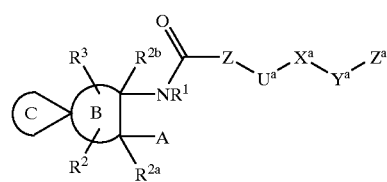

or a stereoisomer or pharmaceutically acceptable salt form thereof, wherein;

A is selected from —$COR^5$, —$CO_2H$, $CH_2CO_2H$, —$CO_2R^6$, —CONHOH, —$CONHOR^5$, —$CONHOR^6$, —$N(OH)COR^5$, —N(OH)CHO, —SH, —$CH_2SH$, —S(O)(=NH)$R^a$, —$SN_2H_2R^a$, —$PO(OH)_2$, and —PO(OH)$NHR^a$;

ring B is a 5 membered non-aromatic carbocycle;

ring C forms a spiro ring on Ring B and is a 5 membered heterocycle consisting of: carbon atoms, 0–1 carbonyl group, 0–1 double bond, and 1 ring heteroatoms selected from O, N, $NR^2$, and $S(O)_p$ and substituted with 0–6 $R^e$;

Z is phenyl substituted with 0–4 $R^b$;

$U^a$ is absent or is O;

$X^a$ is absent or is $C_{1-3}$ alkylene;

$Y^a$ is absent;

$Z^a$ is selected from pyridinyl substituted with 0–3 $R^c$ and quinolinyl substituted with 0–5 $R^c$;

$R^1$ is selected from H, $C_{1-4}$ alkyl, phenyl, and benzyl;

$R^2$ is selected from Q, Cl, F, ($C_{1-10}$ alkylene substituted with 0–3 $R^{b1}$)—Q, ($C_{2-10}$ alkenylene substituted with 0–3 $R^{b1}$)—Q, ($C_{2-10}$ alkynylene substituted with 0–3 $R^{b1}$)—Q, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_{r1}C(O)O$—$C_{2-5}$ alkenylene, $(CR^aR^{a1})_{r1}C(O)O$—$C_{2-5}$ alkynylene, $(CR^aR^{a1})_{r1}OC(O)(CR^aR^{a1})_r$—Q, $(CR^aR^{a1})_{r1}C(O)NR^aR^{a1}$, $(CR^aR^{a1})_{r1}C(O)NR^a(CR^aR^{a1})_r$—Q, $(CR^aR^{a1})_{r1}NR^aC(O)(CR^aR^{a1})_r$—Q, $(CR^aR^{a1})_{r1}OC(O)O(CR^aR^{a1})_r$—Q, $(CR^aR^{a1})_{r1}OC(O)NR^a(CR^aR^{a1})_r$—

Q, $(CR^aR^{a1})_{r1}NR^aC(O)O(CR^aR^{a1})_r$—Q, $(CR^aR^{a1})_{r1}NR^aC(O)NR^a(CR^aR^{a1})_r$—Q, $(CR^aR^{a1})_{r1}S(O)_p(CR^aR^{a1})_r$—Q, $(CR^aR^{a1})_{r1}SO_2NR^a(CR^aR^{a1})_r$—Q, $(CR^aR^{a1})_{r1}NR^aSO_2(CR^aR^{a1})_r$—Q, and $(CR^aR^{a1})_{r1}NR^aSO_2NR^a(CR^aR^{a1})_r$—Q;

$R^{2a}$ is selected from H, $C_{1-6}$ alkyl, $OR^a$, $NR^aR^{a1}$, and $S(O)_pR^a$;

$R^{2b}$ is H or $C_{1-6}$ alkyl;

Q is selected from H and a $C_{3-13}$ carbocycle substituted with 0–5 $R^d$;

$R^3$ is selected from $Q^1$, Cl, F, $C_{1-6}$ alkylene-$Q^1$, $C_{2-6}$ alkenylene-$Q^1$, $C_{2-6}$ alkynylene-$Q^1$, $(CR^aR^{a1})_{r1}O(CR^aR^{a1})_r$—$Q^1$, $(CR^aR^{a1})_{r1}NR^a(CR^aR^{a1})_r$—$Q^1$, $(CR^aR^{a1})_{r1}NR^aC(O)(CR^aR^{a1})_r$—$Q^1$, $(CR^aR^{a1})_{r1}C(O)NR^a(CR^aR^{a1})_r$—$Q^1$, $(CR^aR^{a1})_{r1}C(O)(CR^aR^{a1})_r$—$Q^1$, $(CR^aR^{a1})_{r1}C(O)O(CR^aR^{a1})_r$—$Q^1$, $(CR^aR^{a1}{}_2)_{r1}S(O)_p(CR^aR^{a1})_r$—$Q^1$, and $(CR^aR^{a1})_{r1}SO_2NR^a(CR^aR^{a1})_r$—$Q^1$;

$Q^1$ is selected from H and phenyl substituted with 0–3 $R^d$;

$R^a$, at each occurrence, is independently selected from H, $C_{1-4}$ alkyl, phenyl and benzyl;

$R^{a1}$, at each occurrence, is independently selected from H and $C_{1-4}$ alkyl;

$R^{a2}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, and $CF_2CF_3$;

$R^{b1}$, at each occurrence, is independently selected from $OR^a$, Cl, F, Br, I, =O, —CN, $NO_2$, and $NR^aR^{a1}$;

$R^c$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $CH_2F$, $CHF_2$, $CF_2CH_3$, $C(CH_3)_2F$, $OCF_3$, and $C_{3-10}$ carbocycle substituted with 0–3 $R^{c1}$;

$R^{c1}$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $CH_2F$, and $CHF_2$;

$R^d$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, and $C_{3-10}$ carbocycle;

$R^e$, at each occurrence, is independently selected from $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $NR^aS(O)_2R^{a2}$, $S(O)_pR^{a2}$, $CF_3$, $CF_2CF_3$, $C_{3-10}$ carbocycle substituted with 0–2 $R^{c1}$, and $(CR^aR^{a1})_{r1}$-$C_{3-10}$ carbocycle substituted with 0–2 $R^{c1}$;

$R^5$, at each occurrence, is selected from $C_{1-10}$ alkyl substituted with 0–2 $R^b$ and $C_{1-8}$ alkyl substituted with 0–2 $R^f$;

$R^f$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, $C_{1-10}$ alkyl-$NR^7R^{7a}$, —$CH(R^8)OC(=O)R^9$, and —$CH(R^8)OC(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^g$, $C_{3-8}$ cycloalkyl substituted with 1–2 $R^g$, and phenyl substituted with 0–2 $R^b$;

$R^g$, at each occurrence, is selected from $C_{1-4}$ alkyl, $C_{3-8}$ cycloalkyl, $C_{1-5}$ alkoxy, and phenyl substituted with 0–2 $R^b$;

p, at each occurrence, is selected from 0, 1, and 2;

r, at each occurrence, is selected from 0, 1, 2, 3, and 4; and r1, at each occurrence, is selected from 0, 1, 2, 3, and 4.

2. A compound according to claim 1, wherein the compound is of formula II:

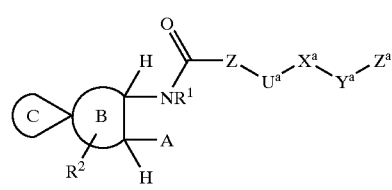

II or a stereoisomer or pharmaceutically acceptable salt form thereof, wherein;

A is selected from —$CO_2H$, $CH_2CO_2H$, —$CONHOH$, —$CONHOR^5$, —$CONHOR^6$, —$N(OH)COR^5$, —$N(OH)CHO$, —SH, and —$CH_2SH$;

Z is phenyl substituted with 0–3 $R^b$;

$R^2$ is selected from Q, $C_{1-6}$ alkylene-Q, $C_{2-6}$ alkenylene-Q, $C_{2-6}$ alkynylene-Q, $(CR^aR^{a1})_{r1}O(CR^aR^{a1})_r$—Q, $(CR^aR^{a1})_{r1}NR^a(CR^aR^{a1})_r$—Q, $(CR^aR^{a1})_{r1}C(O)(CR^aR^{a1})_r$—Q, $(CR^aR^{a1})_{r1}C(O)O(CR^aR^{a1})_r$—Q, $(CR^aR^{a1})_{r1}C(O)NR^aR^{a1}$, $(CR^aR^{a1})_rC(O)NR^a(CR^aR^{a1})_r$—Q, $(CR^aR^{a1})_{r1}S(O)_p(CR^aR^{a1})_r$—Q, and $(CR^aR^{a1})_{r1}SO_2NR^a(CR^aR^{a1})_r$—Q;

Q is selected from H and a $C_{3-6}$ carbocycle substituted with 0–5 $R^d$;

$R^b$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, and $CF_3$;

$R^c$, at each occurrence, is independently selected from $C_{1-6}$ alkyl, $OR^a$, Cl, F, Br, =O, —CN, $NR^aR^{a1}$, $C(O)R^a$, $C(O)OR^a$, $C(O)NR^aR^{a1}$, $S(O)_2NR^aR^{a1}$, $S(O)_pR^{a2}$, $CF_3$, $CH_2F$, $CHF_2$, $CF_2CH_3$, $C(CH_3)_2F$, $OCF_3$, and $C_{3-6}$ carbocycle substituted with 0–2 $R^{c1}$;

$R^{c1}$, at each occurrence, is independently selected from $C_{1-6}$ alkyl, $OR^a$, Cl, F, Br, I, =O, —CN, $NO_2$, $NR^aR^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)OR$^a$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, CF$_2$CF$_3$, CH$_2$F, and CHF$_2$;

R$^d$, at each occurrence, is independently selected from C$_{1-6}$ alkyl, OR$^a$, Cl, F, Br, =O, —CN, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, CF$_3$, and C$_{3-6}$ carbocycle;

R$^7$ is selected from H and C$_{1-6}$ alkyl, C$_{2-6}$ alkenyl, C$_{3-6}$ cycloalkyl-C$_{1-3}$ alkyl-, and phenyl-C$_{1-6}$ alkyl-;

R$^{7a}$ is selected from H and C$_{1-6}$ alkyl, C$_{2-6}$ alkenyl, C$_{3-6}$ cycloalkyl-C$_{1-3}$ alkyl-, and phenyl-C$_{1-6}$ alkyl-;

R$^9$ is selected from H, C$_{1-6}$ alkyl substituted with 1–2 R$^g$, C$_{3-6}$ cycloalkyl substituted with 1–2 R$^g$, and phenyl substituted with 0–2 R$^b$; and R$^g$, at each occurrence, is selected from C$_{1-4}$ alkyl, C$_{3-6}$ cycloalkyl, C$_{1-5}$ alkoxy, and phenyl substituted with 0–2 R$^b$.

3. A compound according to claim 2, wherein the compound is of formula IIIa or IIIb:

IIIa

IIIb or a stereoisomer or pharmaceutically acceptable salt form thereof, wherein;

A is selected from —CO$_2$H, CH$_2$CO$_2$H, —CONHOH, —CONHOR$^5$, —N(OH)CHO, and —N(OH)COR$^5$;

Z$^a$ is selected from pyridinyl substituted with 0–3 R$^c$ and quinolinyl substituted with 0–3 R$^c$;

R$^2$ is selected from Q, C$_{1-6}$ alkylene-Q, C$_{2-6}$ alkenylene-Q, C$_{2-6}$ alkynylene-Q, (CR$^a$R$^{a1}$)$_{r1}$C(O)(CR$^a$R$^{a1}$)$_r$—Q, (CR$^a$R$^{a1}$)$_{r1}$C(O)O(CR$^a$R$^{a1}$)$_r$—Q, (CR$^a$R$^{a2}$)$_{r1}$C(O)NR$^a$R$^{a1}$, (CR$^a$R$^{a2}$)$_{r1}$C(O)NR$^a$(CR$^a$R$^{a1}$)$_r$—Q, and (CR$^a$R$^{a1}$)$_{r1}$S(O)$_p$(CR$^a$R$^{a1}$)$_r$—Q;

Q is selected from H and a C$_{3-6}$ carbocycle substituted with 0–3 R$^d$

R$^b$, at each occurrence, is independently selected from C$_{1-4}$ alkyl, OR$^a$, Cl, F, =O, NR$^a$R$^{a1}$, C(O)R$^a$, C(O)OR$^a$, C(O)NR$^a$R$^{a1}$, S(O)$_2$NR$^a$R$^{a1}$, S(O)$_p$R$^{a2}$, and CF$_3$;

R$^c$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$, CH$_2$F, CHF$_2$, CF$_2$CH$_3$, C(CH$_3$)$_2$F, cyclopropyl, 1-methylcyclopropyl, and cyclobutyl;

R$^d$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, CF$_3$, and phenyl;

R$^5$, at each occurrence, is selected from C$_{1-4}$ alkyl substituted with 0–2 R$^b$, and C$_{1-4}$ alkyl substituted with 0–2 R$^f$;

s and s$^1$ combine to total 2; and s$^2$ and s$^3$ combine to total 3.

4. A compound according to claim 3, wherein the compound is of formula IVa or IVb:

IVa

IVb or a stereoisomer or pharmaceutically acceptable salt form thereof, wherein;

X$^a$ is absent or is CH$_2$ or CH$_2$CH$_2$;

R$^1$ is selected from H, CH$_3$, and CH$_2$CH$_3$;

R$^2$ is selected from Q, C$_{1-6}$ alkylene-Q, C$_{2-6}$ alkynylene-Q, C(O)(CR$^a$R$^{a1}$)$_r$-Q, C(O)O(CR$^a$R$^{a1}$)$_r$-Q, C(O)NR$^a$(CR$^a$R$^{a1}$)$_r$-Q, and S(O)$_p$(CR$^a$R$^{a1}$)$_r$-Q;

Q is selected from H, cyclopropyl substituted with 0–1 R$^d$, cyclobutyl substituted with 0–1 R$^d$, cyclopentyl substituted with 0–1 R$^d$, cyclohexyl substituted with 0–1 R$^d$, and phenyl substituted with 0–2 R$^d$;

R$^a$, at each occurrence, is independently selected from H, CH$_3$, and CH$_2$CH$_3$;

R$^{a1}$, at each occurrence, is independently selected from H, CH$_3$, and CH$_2$CH$_3$;

R$^{a2}$, at each occurrence, is independently selected from H, CH$_3$, and CH$_2$CH$_3$;

s and s$^1$ combine to total 2; and s$^2$ and s$^3$ combine to total 3.

5. A compound according to claim 4, wherein the compound is of formula IVa or IVb, wherein;

Q is selected from H, cyclopropyl substituted with 0–1 R$^d$, cyclobutyl substituted with 0–1 R$^d$, cyclopentyl substituted with 0–1 R$^d$, cyclohexyl substituted with 0–1 R$^d$, and phenyl substituted with 0–2 R$^d$; and R$^c$, at each occurrence, is independently selected from C$_{1-6}$ alkyl, OR$^a$, Cl, F, Br, =O, NR$^a$R$^{a1}$, C(O)R$^a$, C(O)NR$^a$R$^{a1}$, S(O)$_2$NR$^a$R$^{a1}$, S(O)$_p$R$^{a2}$, and CF$_3$.

6. A compound according to claim 4, wherein the compound is of formula IVa or IVb, wherein;

Z is phenyl;

Z$^a$ is a 4-pyridyl substituted with 0–3 R$^c$, and 4-quinolinyl substituted with 0–3 R$^c$;

R$^1$ is H; and

R$^c$, at each occurrence, is independently selected from methyl, ethyl, propyl, isopropyl, butyl, t-butyl, CF$_3$, CHF$_2$, CH$_2$F, CF$_2$CH$_3$, C(CH$_3$)$_2$F, NH$_2$, NH(CH$_3$), N(CH$_3$)$_2$, cyclopropyl, 1-methylcyclopropyl, and cyclobutyl.

7. A compound according to claim 1, wherein the compound is selected from the group:

(5R,7S,8R)-N-hydroxy-8-({4-[(2-methyl-4-quinolinyl)methoxy]benzoyl}amino)-1-oxaspiro[4.4]nonane-7-carboxamide;

(5S,7S,8R)-N-hydroxy-8-({4-[(2-methyl-4-quinolinyl)methoxy]benzoyl}amino)-1-oxaspiro[4.4]nonane-7-carboxamide;

(5R,7S,8R)-N-hydroxy-8-({4-[(2-methyl-4-quinolinyl)methyl]benzoyl}amino)-1-oxaspiro[4.4]nonane-7-carboxamide;

(5R,7S,8R)-N-hydroxy-8-[(4-{[2-(trifluoromethyl)-4quinolinyl]methyl}benzoyl)amino]-1-oxaspiro[4.4]nonane-7-carboxamide;

(5R,7S,8R)-8-({4-[(2-ethyl-4quinolinyl)methyl]benzoyl}amino)-N-hydroxy-1-oxaspiro[4.4]nonane-7-carboxamide;

(5R,7S,8R)-N-hydroxy-8-({4-[(2-isopropyl-4quinolinyl)methyl]benzoyl}amino)-1-oxaspiro[4.4]nonane-7-carboxamide (5R,7S,8R)-8-[(4-{[2-(dimethylamino)-4quinolinyl]methyl}benzoyl)amino]-N-hydroxy-1-oxaspiro[4.4]nonane-7-carboxamide;

(5R,7S,8R)-8-({4-[(2-cyclopropyl-4quinolinyl)methyl]benzoyl}amino)-N-hydroxy-1-oxaspiro[4.4]nonane-7-carboxamide;

(5R,7S,8R)-8-({4-[(2,3-dimethyl-4-quinolinyl)methyl]benzoyl}amino)-N-hydroxy-1-oxaspiro[4.4]nonane-7-carboxamide;

(5R,7S,8R)-N-hydroxy-8-[(4-{[2-methyl-8-(trifluoromethyl)-4-quinolinyl]methyl}benzoyl)amino]-1-oxaspiro[4.4]nonane-7-carboxamide;

(5R,7S,8R)-8-({4-[(3-ethyl-2-methyl-4-quinolinyl)methyl]benzoyl}amino)-N-hydroxy-1-oxaspiro[4.4]nonane-7-carboxamide;

(5R,7S,8R)-8-({4-[(2,6-dimethyl-4-quinolinyl)methyl]benzoyl}amino)-N-hydroxy-1-oxaspiro[4.4]nonane-7-carboxamide;

(5R,7S,8R)-8-({4-[(6-chloro-2-methyl-4-quinolinyl)methyl]benzoyl}amino)-N-hydroxy-1-oxaspiro[4.4]nonane-7-carboxamide;

(5R,7S,8R)-8-({4-[(6-fluoro-2-methyl-4-quinolinyl)methyl]benzoyl}amino)-N-hydroxy-1-oxaspiro[4.4]nonane-7-carboxamide;

(5R,7S,8R)-8-({4-[(7-chloro-2-methyl-4-quinolinyl)methyl]benzoyl}amino)-N-hydroxy-1-oxaspiro[4.4]nonane-7-carboxamide; and (5R,7S,8R)-8-({4-[(2,6-dimethyl-4-pyridinyl)methyl]benzoyl}amino)-N-hydroxy-1-oxaspiro[4.4]nonane-7-carboxamide;

or a pharmaceutically acceptable salt form thereof.

8. A pharmaceutical composition, comprising: a pharmaceutically acceptable carrier and a therapeutically effective amount of a compound according to claim 1 or a pharmaceutically acceptable salt form thereof.

9. A method of treating an inflammatory disorder, comprising: administering to a patient in need thereof a therapeutically effective amount of a compound according to claim 1 or a pharmaceutically acceptable salt form thereof.

10. A method of treating a disease or condition by administering a compound according to claim 1 or pharmaceutically acceptable salt form thereof, wherein the disease or condition is selected from Crohn's disease, psoriasis, psoriatic arthritis, rheumatoid arthritis, and spondylitis.

11. A pharmaceutical composition, comprising: a pharmaceutically acceptable carrier and a therapeutically effective amount of a compound according to claim 2 or a pharmaceutically acceptable salt form thereof.

12. A method of treating an inflammatory disorder, comprising: administering to a patient in need thereof a therapeutically effective amount of a compound according to claim 2 or a pharmaceutically acceptable salt form thereof.

13. A method of treating a disease or condition by administering a compound according to claim 2 or a pharmaceutically acceptable salt form thereof, wherein the disease or condition is selected from Crohn's disease, psoriasis, psoriatic arthritis, rheumatoid arthritis, and spondylitis.

14. A pharmaceutical composition, comprising: a pharmaceutically acceptable carrier and a therapeutically effective amount of a compound according to claim 3 or a pharmaceutically acceptable salt form thereof.

15. A method of treating an inflammatory disorder, comprising: administering to a patient in need thereof a therapeutically effective amount of a compound according to claim 3 or a pharmaceutically acceptable salt form thereof.

16. A method of treating a disease or condition by administering a compound according to claim 3 or a pharmaceutically acceptable salt form thereof, wherein the disease or condition is selected from Crohn's disease, psoriasis, psoriatic arthritis, and spondylitis.

17. A pharmaceutical composition, comprising: a pharmaceutically acceptable carrier and a therapeutically effective amount of a compound according to claim 4 or a pharmaceutically acceptable salt form thereof.

18. A method of treating an inflammatory disorder, comprising: administering to a patient in need thereof a therapeutically effective amount of a compound according to claim 4 or a pharmaceutically acceptable salt form thereof.

19. A method of treating a disease or condition by administering a compound according to claim 4 or a pharmaceutically acceptable salt form thereof, wherein the disease or condition is selected from Crohn's disease, psoriasis, psoriatic arthritis, and spondylitis.

20. A pharmaceutical composition, comprising: a pharmaceutically acceptable carrier and a therapeutically effective amount of a compound according to claim 5 or a pharmaceutically acceptable salt form thereof.

21. A method of treating an inflammatory disorder, comprising: administering to a patient in need thereof a therapeutically effective amount of a compound according to claim 5 or a pharmaceutically acceptable salt form thereof.

22. A method of treating a disease or condition by administering a compound according to claim 5 or a pharmaceutically acceptable salt form thereof, wherein the disease or condition is selected from Crohn's disease, psoriasis, psoriatic arthritis, and spondylitis.

23. A pharmaceutical composition, comprising: a pharmaceutically acceptable carrier and a therapeutically effective amount of a compound according to claim 6 or a pharmaceutically acceptable salt form thereof.

24. A method of treating an inflammatory disorder, comprising: administering to a patient in need thereof a therapeutically effective amount of a compound according to claim 6 or a pharmaceutically acceptable salt form thereof.

25. A method of treating a disease or condition by administering a compound according to claim 6 or a pharmaceutically acceptable salt form thereof, wherein the disease or condition is selected from Crohn's disease, psoriasis, psoriatic arthritis, and spondylitis.

26. A pharmaceutical composition, comprising: a pharmaceutically acceptable carrier and a therapeutically effective amount of a compound according to claim 7 or a pharmaceutically acceptable salt form thereof.

27. A method of treating an inflammatory disorder, comprising: administering to a patient in need thereof a therapeutically effective amount of a compound according to claim 7 or a pharmaceutically acceptable salt form thereof.

28. A method of treating a disease or condition by administering a compound according to claim 7 or a pharmaceutically acceptable salt form thereof, wherein the disease or condition is selected from Crohn's disease, psoriasis, psoriatic arthritis, and spondylitis.

* * * * *